United States Patent
Yu et al.

(10) Patent No.: US 10,829,787 B2
(45) Date of Patent: *Nov. 10, 2020

(54) RIBONUCLEOPROTEIN TRANSFECTION AGENTS

(71) Applicant: LIFE TECHNOLOGIES CORPORATION, Carlsbad, CA (US)

(72) Inventors: Xin Yu, San Marcos, CA (US); Xiquan Liang, Escondido, CA (US); Xavier de Mollerat du Jeu, Encinitas, CA (US); Robert Jason Potter, San Marcos, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/294,586

(22) Filed: Oct. 14, 2016

(65) Prior Publication Data

US 2017/0107539 A1 Apr. 20, 2017

Related U.S. Application Data

(60) Provisional application No. 62/241,559, filed on Oct. 14, 2015.

(51) Int. Cl.
| | | |
|---|---|---|
| C12N 15/90 | (2006.01) | |
| C12N 9/22 | (2006.01) | |
| C12N 15/88 | (2006.01) | |
| A61K 48/00 | (2006.01) | |

(52) U.S. Cl.
CPC ............ *C12N 15/90* (2013.01); *A61K 48/005* (2013.01); *A61K 48/0033* (2013.01); *C12N 9/22* (2013.01); *C12N 15/88* (2013.01); *C12Y 301/00* (2013.01); *C12N 2830/30* (2013.01)

(58) Field of Classification Search
None
See application file for complete search history.

(56) References Cited

U.S. PATENT DOCUMENTS

| | | | |
|---|---|---|---|
| 5,736,392 A | 4/1998 | Hawley-Nelson et al. | |
| 5,795,587 A | 8/1998 | Gao et al. | |
| 6,008,202 A | 12/1999 | Huang et al. | |
| 6,051,429 A * | 4/2000 | Hawley-Nelson | ... A61K 9/1272 435/235.1 |
| 6,376,248 B1 | 4/2002 | Hawley-Nelson et al. | |
| 7,145,039 B2 | 12/2006 | Chu et al. | |
| 7,166,745 B1 | 1/2007 | Chu et al. | |
| 7,173,154 B2 | 2/2007 | Chu et al. | |
| 7,323,594 B2 | 1/2008 | Chu et al. | |
| 7,335,509 B2 | 2/2008 | Huang et al. | |
| 7,361,640 B2 | 4/2008 | Huang et al. | |
| 7,470,817 B2 | 12/2008 | Chu et al. | |
| 7,479,573 B2 | 1/2009 | Chu et al. | |
| 7,601,872 B2 | 10/2009 | Chu et al. | |
| 7,655,468 B2 | 2/2010 | Durham et al. | |
| 7,915,450 B2 | 3/2011 | Chu et al. | |
| 7,993,672 B2 | 8/2011 | Huang et al. | |
| 8,058,068 B2 | 11/2011 | Hawley-Nelson et al. | |
| 8,158,827 B2 | 4/2012 | Chu et al. | |
| 8,771,728 B2 | 7/2014 | Huang et al. | |
| 8,785,200 B2 | 7/2014 | Chu et al. | |
| 9,006,487 B2 | 4/2015 | Anderson et al. | |
| 9,358,300 B2 | 6/2016 | Chu et al. | |
| 9,526,784 B2 | 12/2016 | Liu et al. | |
| 2003/0069173 A1 | 4/2003 | Hawley-Nelson et al. | |
| 2003/0144230 A1* | 7/2003 | Hawley-Nelson | ... A61K 9/1272 514/44 R |
| 2005/0164971 A1 | 7/2005 | Chu et al. | |
| 2006/0229246 A1 | 10/2006 | Hawley-Nelson et al. | |
| 2014/0065596 A1 | 5/2014 | Kim et al. | |
| 2015/0050699 A1 | 2/2015 | Siksnys et al. | |
| 2015/0071903 A1 | 3/2015 | Liu et al. | |
| 2015/0071906 A1 | 3/2015 | Liu et al. | |
| 2015/0118216 A1 | 4/2015 | Liu et al. | |
| 2016/0045600 A1* | 2/2016 | De Mollerat Du Jeu | ............. A61K 31/7105 514/44 R |
| 2016/0090603 A1* | 3/2016 | Carnes | ............... C12N 15/8206 800/278 |
| 2016/0139124 A1* | 5/2016 | Newman | .......... G01N 33/56977 435/7.25 |
| 2016/0200779 A1 | 7/2016 | Liu et al. | |

FOREIGN PATENT DOCUMENTS

| | | |
|---|---|---|
| CA | 2350882 | 2/2011 |
| EP | 1829856 | 9/2007 |
| EP | 1129064 | 1/2008 |
| EP | 2206787 | 7/2010 |

(Continued)

OTHER PUBLICATIONS

Anonymous, "Lipofectamine(TM) 2000 Transfection Reagent", *Application Notes*, 2005, 8 Pages.

Anonymous, "Manuals and protocols: Lipofectamine™ Crisprmax™ Transfection Reagent", Thermo Fisher Scientific Inc., retrieved from the Internet: URL:https://tools.thermofisher.com/content/sfs/manuals/lipofectamine_crisprmax_man.pdf, Sep. 28, 2015, 4 pages.

Eltoukhy, et al., "Nucleic acid-mediated intracellular protein delivery by lipid-like nanoparticles", *Biomaterials*, vol. 35, May 13, 2014, 6454-6461.

Liang, et al., "Rapid and highly efficient mammalian cell engineering via Cas9 protein transfection", *Journal of Biotechnology*, vol. 208, May 21, 2015, 44-53.

(Continued)

*Primary Examiner* — Antonio Galisteo Gonzalez
(74) *Attorney, Agent, or Firm* — Life Technologies Corporation; Karen R. Zachow

(57) ABSTRACT

Provided herein are compositions and methods useful, inter alia, for the delivery of ribonucleoprotein complexes (e.g., Cas9/guide RNA complexes) into cells. The compositions and methods provided herein are particularly useful for the delivery of ribonucleoprotein complexes into pluripotent cells and lymphatic cells.

15 Claims, 40 Drawing Sheets

Specification includes a Sequence Listing.

(56) References Cited

FOREIGN PATENT DOCUMENTS

| EP | 2298728 | 3/2011 |
|---|---|---|
| JP | 4265699 | 5/2009 |
| JP | 4338106 | 10/2009 |
| WO | WO 96/40961 | 12/1996 |
| WO | WO 98/40502 | 9/1998 |
| WO | WO 00/027795 | 5/2000 |
| WO | WO-2015/035136 | 3/2015 |
| WO | WO-2016/070129 | 5/2016 |

OTHER PUBLICATIONS

PCT/US2016/057224, "International Search Report dated", Jan. 20, 2017, 5 pages.

Sahay, et al., "Efficiency of siRNA delivery by lipid nanoparticles is limited by endocytic recycling", *Nature Biotechnology*, Advance Online Publication, Jun. 23, 2013, 1-9.

Yu, Xin et al., "Improved delivery of Cas9 protein/gRNA complexes using lipofectamine Crisprmax", *Biotechnology Letters*, vol. 38, No. 6, Jun. 2016, 919-929.

Zuris, et al., "Cationic lipid-mediated delivery of proteins enables efficient protein-based genome editing in vitro and in vivo", *Nature Biotechnology*, vol. 33, No. 1, Jan. 2015, 73-80.

\* cited by examiner

SEQUENCE LISTING

<160> NUMBER OF SEQ ID NOS: 64

<210> SEQ ID NO 1
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Cys Gly Tyr Gly Gly Gly Gly Gly Pro Lys Lys Lys Arg Lys Val
1               5                   10                  15

Gly Gly Gly Leu Phe Glu Ala Ile Ala Glu Phe Ile Glu Gly Gly Trp
            20                  25                  30

Glu Gly Leu Ile Glu Gly
        35

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

```
Cys Gly Tyr Gly Pro Lys Lys Arg Lys Val Gly Gly Gly Arg
1               5                  10                  15

Gly Asp Ser Pro Cys Gly
                20

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Gly Tyr Gly Pro Lys Lys Arg Lys Val Gly Gly Lys Phe Thr
1               5                  10                  15

Ile Val Phe

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Cys Gly Tyr Gly Pro Lys Lys Lys Arg Lys Val Gly
1               5                  10

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Gly Tyr Gly Pro Lys Lys Lys Arg Lys Val Gly Gly
1               5                  10                  15

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Arg Gly Asp Met Phe Gly Gly
1               5

<210> SEQ ID NO 7
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Val Lys Arg Lys Lys Lys Pro Gly Tyr Gly Gly Gly Val
1               5                  10                  15
```

Lys Arg Lys Lys Lys Pro Gly Tyr Gly Gly
            20              25

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Tyr Gly Pro Lys Lys Arg Lys Val Gly
1               5                   10

<210> SEQ ID NO 9
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Tyr Gly Pro Lys Lys Arg Lys Val Gly Gly Gly Gly Tyr
1               5                   10                  15

Gly Pro Lys Lys Lys Arg Lys Val Gly Gly
            20              25

<210> SEQ ID NO 10
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Tyr Gly Pro Lys Lys Arg Lys Val Gly Gly Gly Gly Tyr
1               5                   10                  15

Gly Pro Lys Lys Lys Arg Lys Val Gly Gly
            20              25

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Lys Phe Thr Ile Val Phe Asp Asp Asp Asp Asp
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Lys Phe Thr Ile Val Phe Asp Asp Asp Asp Asp Gly
1               5                   10

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Leu Phe Glu Ala Ile Ala Glu Phe Ile Glu Gly Gly Trp Glu Gly
1               5                   10                  15

Leu Ile Glu Gly
            20

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Leu Phe Glu Ala Ile Ala Glu Phe Ile Glu Gly Gly Trp Glu Gly
1               5                   10                  15

Leu Ile Glu Gly Cys Lys Phe Thr Ile Val Phe
            20                  25

<210> SEQ ID NO 15
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Leu Phe Glu Ala Ile Ala Glu Phe Ile Glu Gly Gly Trp Glu Gly
1               5                   10                  15

Leu Ile Glu Gly Gly Gly Tyr Gly Gly Gly Gly Gly Pro Lys Lys
            20                  25                  30

Lys Arg Lys Val Gly Gly
        35

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Leu Phe Glu Ala Ile Ala Ile Glu Phe Ile Glu Gly Gly Trp Glu
1               5                   10                  15

Gly Leu Ile Glu Gly
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Leu Phe Gly Ala Ile Ala Gly Phe Ile Glu Asn Gly Trp Glu Gly
1               5                   10                  15

Met Ile Asp Gly
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Leu Phe Lys Ala Ile Ala Lys Phe Ile Lys Gly Gly Trp Lys Gly
1               5                   10                  15

Leu Ile Lys Gly
            20

<210> SEQ ID NO 19
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Arg Gly Asp Ser Pro Cys Gly Gly Lys Lys Lys Lys Lys Lys
1               5                   10                  15

Lys Lys Lys Lys Lys Lys Lys Lys Lys
            20                  25

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Tyr Gly Pro Lys Lys Lys Arg Lys Val Gly Gly
1               5                   10

<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Tyr Gly Pro Lys Lys Lys Arg Lys Val Gly Gly Gly Gly Arg
1               5                   10                  15

Gly Asp Met Phe Gly Gly
            20

<210> SEQ ID NO 22
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 22

Lys Phe Thr Ile Val Phe
1               5

<210> SEQ ID NO 23
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Phe Thr Ile Val Phe Gly Gly Gly Leu Phe Glu Ala Ile Ala Glu
1               5                   10                  15

Phe Ile Glu Gly Gly Trp Glu Gly Leu Ile Glu Gly
            20                  25

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Phe Thr Thr Ile Val Phe Cys Gly Tyr Gly Pro Lys Lys Lys Arg
1               5                   10                  15

Lys Val Gly Gly
            20

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Lys Lys Lys Lys Lys Lys Lys Lys Lys Lys Lys Lys Lys Lys Lys
1               5                   10                  15

<210> SEQ ID NO 26
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Lys Lys Lys Lys Lys Lys Lys Lys Lys Lys Lys Lys Lys Lys Lys Lys
1               5                   10                  15

Cys Gly Tyr Gly Pro Lys Lys Arg Lys Val Gly Gly Gly Arg
            20                  25                  30

Gly Asp Ser Pro
            35

<210> SEQ ID NO 27
```

```
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Lys Lys Lys Lys Lys Lys Lys Lys Lys Lys Lys Lys Lys Lys Lys Lys
1               5                   10                  15

Gly Gly Cys Gly Tyr Gly Gly Gly Gly Gly Pro Lys Lys Lys Arg
            20                  25                  30

Lys Val Gly Gly Gly Leu Phe Glu Ala Ile Ala Glu Phe Ile Glu Gly
                35                  40                  45

Gly Trp Glu Gly Leu Ile Glu Gly
    50                  55

<210> SEQ ID NO 28
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Lys Lys Lys Lys Lys Lys Lys Lys Lys Lys Lys Lys Lys Lys Lys Lys
1               5                   10                  15

Gly Gly Cys Gly Tyr Gly Gly Gly Pro Lys Lys Lys Arg Lys Val Gly
            20                  25                  30

Gly Lys Phe Thr Ile Val Phe
        35

<210> SEQ ID NO 29
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Lys Lys Lys Lys Lys Lys Lys Lys Lys Lys Lys Lys Lys Lys Lys Lys
1               5                   10                  15

Gly Gly Cys Gly Tyr Gly Pro Lys Lys Lys Arg Lys Val Gly Gly
            20                  25                  30

<210> SEQ ID NO 30
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Lys Lys Lys Lys Lys Lys Lys Lys Lys Lys Lys Lys Lys Lys Lys
1               5                   10                  15

Gly Gly Arg Gly Asp Ser Pro Cys Gly
            20                  25

<210> SEQ ID NO 31
<211> LENGTH: 29
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 31

Lys Lys Lys Lys Lys Lys Lys Lys Lys Lys Lys Lys Lys Lys Lys Lys
1               5                   10                  15
Gly Lys Phe Thr Ile Val Phe Asp Asp Asp Asp Asp
            20                  25

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Lys Lys Lys Lys Lys Lys Lys Lys Lys Lys Lys Lys Lys Lys Lys Lys
1               5                   10                  15
Gly Lys Phe Thr Ile Val Phe Asp Asp Asp Asp Asp Gly
            20                  25                  30

<210> SEQ ID NO 33
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Lys Lys Lys Lys Lys Lys Lys Lys Lys Lys Lys Lys Lys Lys Lys Lys
1               5                   10                  15
Gly Leu Phe Glu Ala Ile Ala Glu Phe Ile Glu Gly Gly Trp Glu Gly
            20                  25                  30
Leu Ile Glu Gly Cys Lys Phe Thr Ile Val Phe
        35                  40

<210> SEQ ID NO 34
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Lys Lys Lys Lys Lys Lys Lys Lys Lys Lys Lys Lys Lys Lys Lys Lys
1               5                   10                  15
Gly Leu Phe Glu Ala Ile Ala Glu Phe Ile Glu Gly Gly Trp Glu Gly
            20                  25                  30
Leu Ile Glu Gly Gly Gly Tyr Gly Gly Gly Gly Gly Pro Lys Lys
        35                  40                  45
Lys Arg Lys Val Gly Gly
    50

<210> SEQ ID NO 35
<211> LENGTH: 44
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 35

Lys Lys Lys Lys Lys Lys Lys Lys Lys Lys Lys Lys Lys Lys Lys Lys
1               5                   10                  15

Lys Phe Thr Ile Val Phe Gly Gly Gly Leu Phe Glu Ala Ile Ala Glu
            20                  25                  30

Phe Ile Glu Gly Gly Trp Glu Gly Leu Ile Glu Gly
            35                  40

<210> SEQ ID NO 36
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Lys Lys Lys Lys Lys Lys Lys Lys Lys Lys Lys Lys Lys Lys Lys Lys
1               5                   10                  15

Lys Phe Thr Thr Ile Val Phe Cys Gly Tyr Gly Pro Lys Lys Lys Arg
            20                  25                  30

Lys Val Gly Gly
        35

<210> SEQ ID NO 37
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Lys Lys Lys Lys Lys Lys Lys Lys Lys Lys Lys Lys Lys Lys Lys Lys
1               5                   10                  15

Ser Ser Asp Asp Glu Ala Thr Ala Asp Ser Gln His Ser Thr Pro Pro
            20                  25                  30

Lys Lys Lys Arg Lys Val Gly Gly
        35                  40

<210> SEQ ID NO 38
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Ser Tyr Tyr His His His His His His Asp Tyr Asp Ile Pro Thr
1               5                   10                  15

Thr Glu Asn Leu Tyr Phe Gln Gly Ser Gly Leu Phe Glu Ala Ile Ala
            20                  25                  30

Glu Phe Ile Glu Gly Gly Trp Glu Gly Leu Ile Glu Gly
            35                  40                  45

<210> SEQ ID NO 39
<211> LENGTH: 37
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 39

Met Ser Tyr Tyr His His His His His His Asp Tyr Asp Ile Pro Thr
1               5                   10                  15

Thr Glu Asn Leu Tyr Phe Gln Gly Ser Gly Tyr Gly Pro Lys Lys Lys
            20                  25                  30

Arg Lys Val Gly Gly
        35

<210> SEQ ID NO 40
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Ser Tyr Tyr His His His His His His Asp Tyr Asp Ile Pro Thr
1               5                   10                  15

Thr Glu Asn Leu Tyr Phe Gln Gly Ser Lys Phe Thr Ile Val Phe
            20                  25                  30

<210> SEQ ID NO 41
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Ser Tyr Tyr His His His His His His Asp Tyr Asp Ile Pro Thr
1               5                   10                  15

Thr Glu Asn Leu Tyr Phe Gln Gly Ser Arg Gly Asp Ser Pro Cys
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Ser Tyr Tyr His His His His His His Gly Leu Phe Glu Ala Ile
1               5                   10                  15

Ala Glu Phe Ile Glu Gly Gly Trp Glu Gly Leu Ile Glu Gly
            20                  25                  30

<210> SEQ ID NO 43
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Met Ser Tyr Tyr His His His His His His Gly Tyr Gly Pro Lys Lys
1               5                   10                  15
```

Lys Arg Lys Val Gly Gly
            20

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Met Ser Tyr Tyr His His His His His His Lys Phe Thr Ile Val Phe
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Met Ser Tyr Tyr His His His His His His Arg Gly Asp Ser Pro Cys
1               5                   10                  15

<210> SEQ ID NO 46
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Ser Asp Asp Glu Ala Thr Ala Asp Ser Gln His Ser Thr Pro Pro
1               5                   10                  15

Lys Lys Lys Arg Lys Val Gly Gly
            20

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Lys Lys Lys Arg Lys Val
1               5

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcatttctca gtcctaaaca ggg                                         23

<210> SEQ ID NO 49
<211> LENGTH: 18

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acatcagcag ctgttctg                                                   18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ggctgaaagg agagaact                                                   18

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gaatatgtga gtgtggatgg                                                 20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggatccatcg cagcctttct                                                 20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
actacctggt tcgggtggtt                                                 20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggcgctcaag agtccacagg                                                 20

<210> SEQ ID NO 55
<211> LENGTH: 23
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 55
agcatcctct acagcttgct cac                                             23

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggtactgatg ttcagactcc agc                                             23

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
agatgggcgg gagtcttctg gg                                              22

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gggctgagcg gctgcggggc g                                               21

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctgtagtaag gatctcaagc aggag                                           25

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ccagggcacg ggcagcttgc cgg                                             23

<210> SEQ ID NO 61
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 61
atggtgagca agggcgagga gctg                                            24

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gtcctccttg aagtcgatgc cc                                              22

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ctcgtgacca ccttcaccta cgg                                             23

<210> SEQ ID NO 64
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcaccta cggcgtgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctgggcac      420 aagctggagt acaactacaa cagccacaag gtctatatca ccgccgacaa gcagaagaac     480
ggcatcaagg tgaacttcaa gacccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

RIBONUCLEOPROTEIN TRANSFECTION AGENTS

CROSS-REFERENCE

This application claims the right of priority under 35 U.S.C. § 119(e) to U.S. Provisional Appl. No. 62/241,559, filed Oct. 14, 2015, which is commonly owned this with application and which is hereby expressly incorporated by reference in its entirety as though fully set forth herein.

SEQUENCE LISTING

This application hereby incorporates by reference the material of the electronic Sequence Listing filed concurrently herewith. The material in the electronic Sequence Listing is submitted electronically in ASCII format and is hereby incorporated by reference in its entirety. Said ASCII copy, created on Oct. 14, 2016, is named LT01100_SL.txt and is 22,543 bytes in size.

BACKGROUND OF THE INVENTION

Recent advances in CRISPR technology have enabled researchers to engineer cells and circuits efficiently in vivo. However, the potential off-target effects of Cas9 nuclease remain a major concern for therapeutic applications. Recently, the delivery of purified Cas9 protein and gRNA complexes (Cas9 RNPs) has gained increasing attention due to high editing efficiency and reduced off-target effects. Although Cas9 RNPs can be delivered into mammalian cells via electroporation, lipid-mediated transfection, which is the preferred delivery method due to ease of use, low cost, and adaptation to high throughput systems has been inefficient in delivering Cas9 RNPs. Especially pluripotent stem cells and cells of lymphatic origin have been resistant to transfection with CAS9 RNPs using lipid-mediated methodologies. Therefore, there is a need in the art for transfection compositions and methods enabling delivery of nucleic acids, proteins and/or ribonucleoproteins into these cells. The invention provided herein addresses these and other shortcomings in the art.

BRIEF SUMMARY OF THE INVENTION

In a first aspect, there is provided a composition including a ribonucleoprotein complex, a lipid aggregate-forming cationic lipid and an enhancer element.

In another aspect, there is provided a method of forming a cell transfection composition. The method includes the steps: (i) contacting a ribonucleic acid, an endonuclease and an enhancer element, thereby forming a ribonucleoprotein-enhancer element complex; and (ii) contacting the lipid aggregate-forming cationic lipid with the ribonucleoprotein-enhancer element complex, thereby forming a cell transfection composition.

In another aspect, there is provided a method of forming a cell transfection composition. The method includes the steps: (i) contacting a lipid aggregate-forming cationic lipid with a cell culture medium in a first reaction vessel, thereby forming a lipid aggregate-forming cationic lipid medium; (ii) contacting a ribonucleic acid, an endonuclease and an enhancer element in a second reaction vessel, thereby forming a ribonucleoprotein-enhancer element complex; and (iii) contacting the lipid aggregate-forming cationic lipid medium with the ribonucleoprotein-enhancer element complex in the second reaction vessel, thereby forming a cell transfection composition.

In another aspect, there is provided a method of forming a cell transfection composition. The method includes the steps: (i) contacting a ribonucleic acid, an endonuclease and an enhancer element in a first reaction vessel, thereby forming a ribonucleoprotein-enhancer element complex; (ii) contacting a lipid aggregate-forming cationic lipid with a cell culture medium in a second reaction vessel, thereby forming a lipid aggregate-forming cationic lipid medium; and (iii) contacting the ribonucleoprotein-enhancer element complex with the lipid aggregate-forming cationic lipid medium in the second reaction vessel, thereby forming a cell transfection composition.

In another aspect, there is provided an in vitro cell culture including a eukaryotic cell, a ribonucleoprotein complex, a lipid aggregate-forming cationic lipid and an enhancer element.

In another aspect, there is provided a method of transfecting a ribonucleoprotein complex into a cell. The method includes contacting a cell with the composition provided herein including embodiments thereof.

BRIEF DESCRIPTION OF THE DRAWINGS

FIG. 3A-3C: Stability of Cas9 RNP complexes in A549, HEK283 and Hela cells, respectively. FIG. 3D-3F: Stability of CRISPRMAX™ in OPTI-MEM® in A549, HEK283 and Hela cells, respectively. FIG. 3G-3I: Stability of Cas9RNP and CRISPRMAX™ complexes in A549, HEK283 and Hela cells, respectively.

(FIG. 5A) Prior to transfection (0 hr) and at 48 hrs post transfection (48 hr), the morphologies of A549, Hela, and human epidermal keratinocytes (HEKa) were examined by an INCUCYTE™ instrument. (FIG. 5B) Histogram depicting genome modification efficiencies determined at 48 hrs post transfection. (FIG. 5C) Cell viabilities were measured by trypan blue before (0 hr) and after 48 hrs post transfection. Histogram bin legend: 0-hr (diagonal stripes), 48-hr (solid).

FIG. 6E: Histogram depicting relative percentage under conditions indicated in legend. FIG. 6F: Histogram depicting percentage of GFP+ cells. Histogram legend (left to right): Neg, Cas9/D, Cas9 RNP, Cas9 RNP/D.

DETAILED DESCRIPTION OF THE INVENTION

Definitions

Figure 1A:
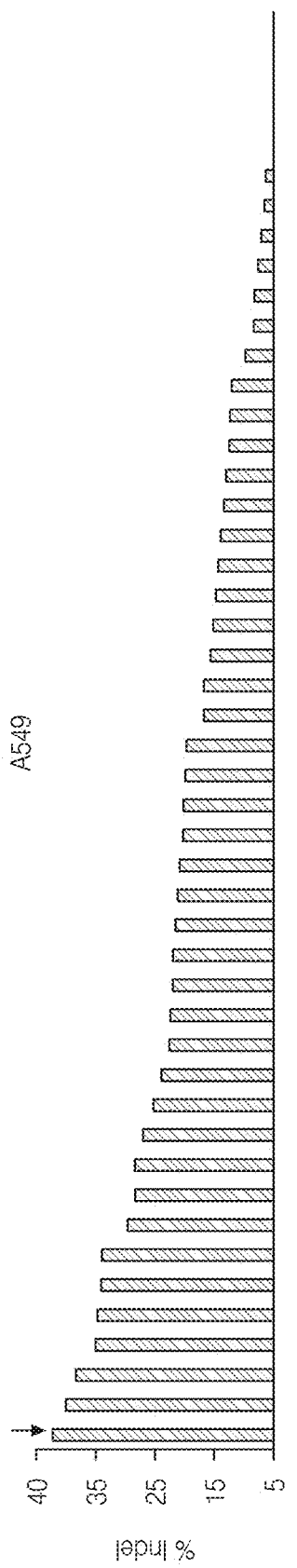
FIGS. 1A-1D. Identification of LIPOFECTAMINE® CRISPRMAX™. A systematic DOE (design of experiment) approach was used to screen more than 60 transfection reagents using six different cell lines in 96 well formats. See Methods section. Genome cleavage efficiency was used as output. Here only 48 reagents (x-axis bins) were shown in four different cell lines (A549, HEK293, Hela and HepG2). Transfection reagent 47 (arrow) indicates LIPOFECTAMINE® CRISPRMAX™. Legend of cell types: panels top to bottom: A549, HEK293, Hela, HepG2. % Indel: "percent insertions and deletions."
Figure 1B:
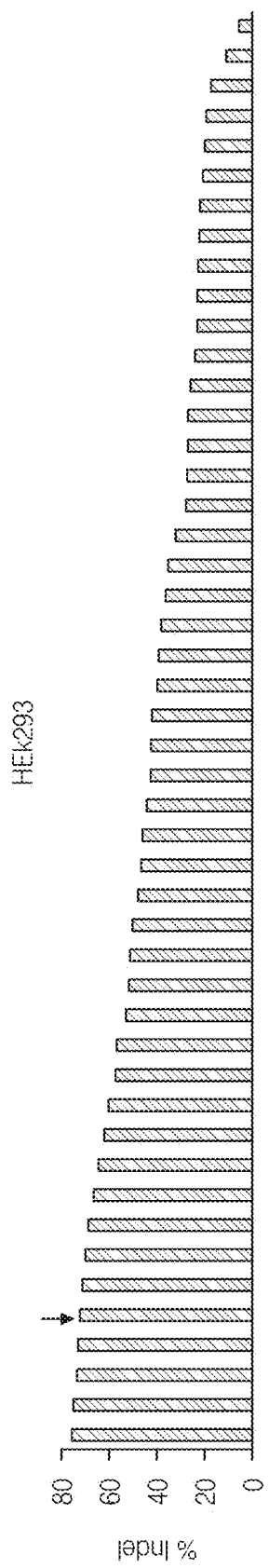
Figure 1C:
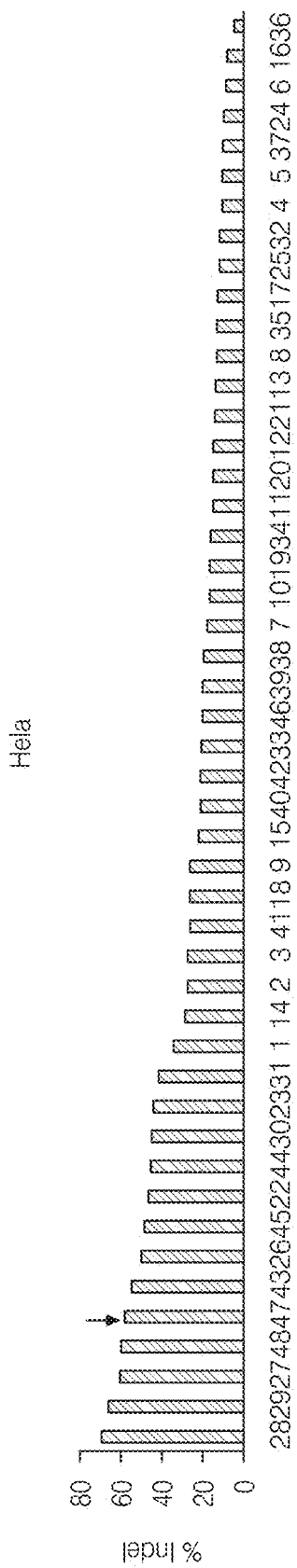
Figure 1D:
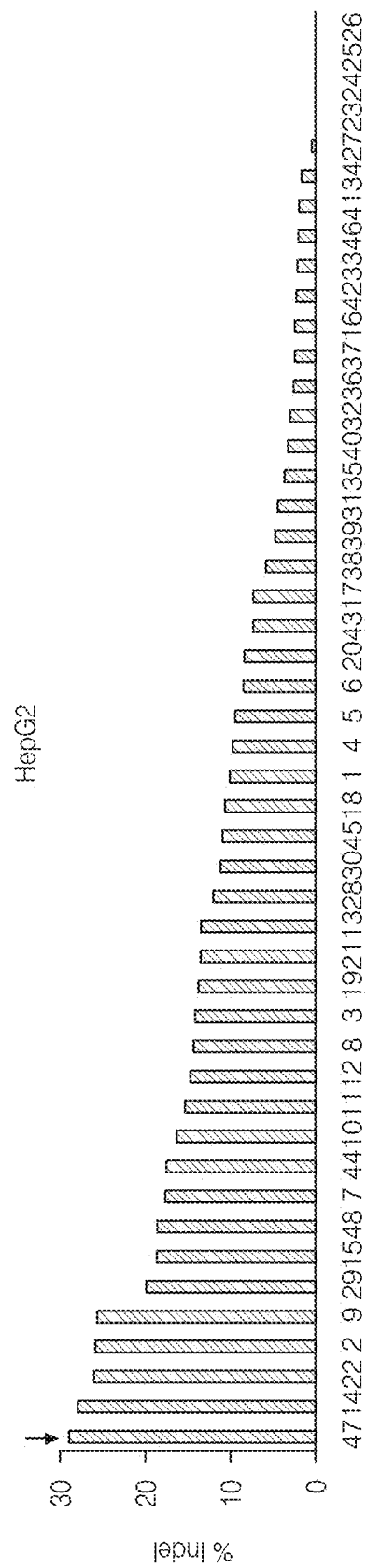

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $-CH_2O-$ is equivalent to $-OCH_2-$.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker ($-O-$).

The term "alkylene," by itself or as part of another substituent, means, unless otherwise stated, a divalent radical derived from an alkyl, as exemplified, but not limited by, $-CH_2CH_2CH_2CH_2-$. Typically, an alkyl (or alkylene) group will have from 1 to 24 carbon atoms, with those groups having 10 or fewer carbon atoms being preferred. A "lower alkyl" or "lower alkylene" is a $C_1$-$C_8$ alkyl or alkylene group.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Heteroalkyl is an uncyclized chain. Examples include, but are not limited to: $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2-$, $-S(O)-CH_3$, $-CH_2-CH_2-S(O)_2-CH_3$, $-CH=CH-O-CH_3$, $-Si(CH_3)_3$, $-CH_2-CH=N-OCH_3$, $-CH=CH-N(CH_3)-CH_3$, $-O-CH_3$, $-O-CH_2-CH_3$, and $-CN$. Up to two heteroatoms may be consecutive, such as, for example, $-CH_2-NH-OCH_3$.

Similarly, the term "heteroalkylene," by itself or as part of another substituent, means, unless otherwise stated, a divalent radical derived from heteroalkyl, as exemplified, but not limited by, $-CH_2-CH_2-S-CH_2-CH_2-$ and $-CH_2-S-CH_2-CH_2-NH-CH_2-$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $-C(O)_2R'-$ represents both $-C(O)_2R'-$ and $-R'C(O)_2-$. As described above, heteroalkyl groups, as used herein, include those groups that are attached to the remainder of the molecule through a heteroatom, such as $-C(O)R'$, $-C(O)NR'$, $-NR'R''$, $-OR'$, $-SR'$, and/or $-SO_2R'$. Where "heteroalkyl" is recited, followed by recitations of specific heteroalkyl groups, such as $-NR'R''$ or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "alkylsulfonyl," as used herein, means a moiety having the formula —S($O_2$)—R', where R' is an alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound disclosed herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR''', —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound disclosed herein includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In embodiments, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:
 (A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocloalkyl, unsubstituted aryl, unsubstituted heteroaryl, and
 (B) alkyl, heteroalkyl, cycloalkyl, heterocycloalkyl, aryl, and heteroaryl, substituted with at least one substituent selected from:
  (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
   (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
   (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth herein.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism. An "inhibitory nucleic acid" is a nucleic acid (e.g. DNA, RNA, polymer of nucleotide analogs) that is capable of binding to a target nucleic acid (e.g. an mRNA translatable into a protein) and reducing transcription of the target nucleic acid (e.g. mRNA from DNA) or reducing the translation of the target nucleic acid (e.g.mRNA) or altering transcript splicing (e.g. single stranded morpholino oligo).

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the phosphorothioate nucleic acid or phosphorothioate polymer backbone includes a detectable label, as disclosed herein and generally known in the art.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854).

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "purified" denotes that a nucleic acid or protein gives rise to essentially one band in an electrophoretic gel. In some embodiments, the nucleic acid or protein is at least 50% pure, optionally at least 65% pure, optionally at least 75% pure, optionally at least 85% pure, optionally at least 95% pure, and optionally at least 99% pure.

The term "isolated" may also refer to a cell or sample cells. An isolated cell or sample cells are a single cell type that is substantially free of many of the components which normally accompany the cells when they are in their native state or when they are initially removed from their native state. In certain embodiments, an isolated cell sample retains those components from its natural state that are required to maintain the cell in a desired state. In some embodiments, an isolated (e.g. purified, separated) cell or isolated cells, are cells that are substantially the only cell type in a sample. A purified cell sample may contain at least 60%, 70%, 75%, 80%, 85%, 90%, 95%, 96%, 97%, 98%, 99%, or 100% of one type of cell. An isolated cell sample may be obtained through the use of a cell marker or a combination of cell markers, either of which is unique to one cell type in an unpurified cell sample. In some embodiments, the cells are isolated through the use of a cell sorter. In some embodiments, antibodies against cell proteins are used to isolate cells.

As used herein, the term "conjugate" refers to the association between atoms or molecules. The association can be direct or indirect. For example, a conjugate between a first moiety (e.g., polyamine moiety) and a second moiety (peptide moiety) provided herein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first moiety (e.g., polyamine moiety) is non-covalently attached to the second moiety (peptide moiety) through a non-covalent chemical reaction between a component of the first moiety (e.g., polyamine moiety) and a component of the second moiety (peptide moiety). In other embodiments, the first moiety (e.g., polyamine moiety)

includes one or more reactive moieties, e.g., a covalent reactive moiety, as described herein (e.g., alkyne, azide, maleimide or thiol reactive moiety). In other embodiments, the first moiety (e.g., polyamine moiety) includes a linker with one or more reactive moieties, e.g., a covalent reactive moiety, as described herein (e.g., alkyne, azide, maleimide or thiol reactive moiety). In other embodiments, the second moiety (peptide moiety) includes one or more reactive moieties, e.g., a covalent reactive moiety, as described herein (e.g., alkyne, azide, maleimide or thiol reactive moiety). In other embodiments, the second moiety (peptide moiety) includes a linker with one or more reactive moieties, e.g., a covalent reactive moiety, as described herein (e.g., alkyne, azide, maleimide or thiol reactive moiety).

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. The terms apply to macrocyclic peptides, peptides that have been modified with non-peptide functionality, peptidomimetics, polyamides, and macrolactams. A "fusion protein" refers to a chimeric protein encoding two or more separate protein sequences that are recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V);

6) Phenylalanine (F), Tyrosine (Y), Tryptophan (W); 7) Serine (S), Threonine (T); and 8) Cysteine (C), Methionine (M).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

An example of an algorithm that is suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

Yet another indication that two nucleic acid sequences are substantially identical is that the same primers can be used to amplify the sequence.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. In embodiments contacting includes, for example, allowing a ribonucleic acid as described herein to interact with a an endonuclease and an enhancer element.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells.

A "stem cell" is a cell characterized by the ability of self-renewal through mitotic cell division and the potential to differentiate into a tissue or an organ. Among mammalian stem cells, embryonic and somatic stem cells can be distinguished. Embryonic stem cells reside in the blastocyst and give rise to embryonic tissues, whereas somatic stem cells reside in adult tissues for the purpose of tissue regeneration and repair.

The term "pluripotent" or "pluripotency" refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism. A standard art-accepted test, such as the ability to form a teratoma in 8-12 week old SCID mice, can be used to establish the pluripotency of a cell population. However, identification of various pluripotent stem cell characteristics can also be used to identify pluripotent cells.

"Pluripotent stem cell characteristics" refer to characteristics of a cell that distinguish pluripotent stem cells from other cells. Expression or non-expression of certain combinations of molecular markers are examples of characteristics of pluripotent stem cells. More specifically, human pluripotent stem cells may express at least some, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Lin28, Rex1, and Nanog. Cell morphologies associated with pluripotent stem cells are also pluripotent stem cell characteristics.

The terms "induced pluripotent stem cell," "iPS" and the like refer to a pluripotent stem cell artificially derived from a non-pluripotent cell. A "non-pluripotent cell" can be a cell of lesser potency to self-renew and differentiate than a pluripotent stem cell. Cells of lesser potency can be, but are not limited to adult stem cells, tissue specific progenitor cells, primary or secondary cells.

"Self renewal" refers to the ability of a cell to divide and generate at least one daughter cell with the self-renewing characteristics of the parent cell. The second daughter cell may commit to a particular differentiation pathway. For example, a self-renewing hematopoietic stem cell can divide and form one daughter stem cell and another daughter cell committed to differentiation in the myeloid or lymphoid pathway. A committed progenitor cell has typically lost the self-renewal capacity, and upon cell division produces two daughter cells that display a more differentiated (i.e., restricted) phenotype. Non-self renewing cells refers to cells that undergo cell division to produce daughter cells, neither of which have the differentiation potential of the parent cell type, but instead generates differentiated daughter cells.

An adult stem cell is an undifferentiated cell found in an individual after embryonic development. Adult stem cells multiply by cell division to replenish dying cells and regenerate damaged tissue. An adult stem cell has the ability to divide and create another cell like itself or to create a more differentiated cell. Even though adult stem cells are associated with the expression of pluripotency markers such as Rex1, Nanog, Oct4 or Sox2, they do not have the ability of pluripotent stem cells to differentiate into the cell types of all three germ layers. Adult stem cells have a limited ability to self renew and generate progeny of distinct cell types. Adult stem cells can include hematopoietic stem cell, a cord blood stem cell, a mesenchymal stem cell, an epithelial stem cell, a skin stem cell or a neural stem cell. A tissue specific progenitor refers to a cell devoid of self-renewal potential that is committed to differentiate into a specific organ or tissue. A primary cell includes any cell of an adult or fetal organism apart from egg cells, sperm cells and stem cells. Examples of useful primary cells include, but are not limited to, skin cells, bone cells, blood cells, cells of internal organs and cells of connective tissue. A secondary cell is derived from a primary cell and has been immortalized for long-lived in vitro cell culture.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell (Sambrook et al., 1989, Molecular Cloning: A Laboratory Manual, 18.1-18.88).

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The term "plasmid" refers to a nucleic acid molecule that encodes for genes and/or regulatory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids.

The term "episomal" refers to the extra-chromosomal state of a plasmid in a cell. Episomal plasmids are nucleic acid molecules that are not part of the chromosomal DNA and replicate independently thereof.

The term "exogenous" refers to a molecule or substance (e.g., nucleic acid or protein) that originates from outside a given cell or organism. Conversely, the term "endogenous" refers to a molecule or substance that is native to, or originates within, a given cell or organism.

A "vector" is a nucleic acid that is capable of transporting another nucleic acid into a cell. A vector is capable of directing expression of a protein or proteins encoded by one or more genes carried by the vector when it is present in the appropriate environment.

A "cell culture" is an in vitro population of cells residing outside of an organism. The cell culture can be established from primary cells isolated from a cell bank or animal, or secondary cells that are derived from one of these sources and immortalized for long-term in vitro cultures.

The terms "transfection", "transduction", "transfecting" or "transducing" can be used interchangeably and are defined as a process of introducing a nucleic acid molecule and/or a protein to a cell. Nucleic acids may be introduced to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In some aspects, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) Gene Therapy 8:1-4 and Prochiantz (2007) Nat. Methods 4:119-20.

As used herein, the terms "specific binding" or "specifically binds" refer to two molecules forming a complex (e.g., a ribonucleoprotein and an enhancer element) that is relatively stable under physiologic conditions.

Methods for determining whether a ligand (e.g., antibody) binds to a protein (antigen) and/or the affinity for a ligand to a protein are known in the art. For example, the binding of a ligand to a protein can be detected and/or quantified using a variety of techniques such as, but not limited to, Western blot, dot blot, surface plasmon resonance method (e.g., BIAcore system; Pharmacia Biosensor AB, Uppsala, Sweden and Piscataway, N.J.), isothermal titration calorimetry (ITC), or enzyme-linked immunosorbent assays (ELISA).

Immunoassays which can be used to analyze immunospecific binding and cross-reactivity of the ligand include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, and fluorescent immunoassays. Such assays are routine and well known in the art.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "VH" refer to the variable region of an immunoglobulin heavy chain, including an Fv, scFv, dsFv or Fab; while the terms "variable light chain," "$V_L$" or "VL" refer to the variable region of an immunoglobulin light chain, including of an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., FUNDAMENTAL IMMUNOLOGY (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) Nature 348:552). The term "antibody" also includes bivalent or bispecific molecules, diabodies, triabodies, and tetrabodies. Bivalent and bispecific molecules are described in, e.g., Kostelny et al. (1992) *J. Immunol.* 148:1547, Pack and Pluckthun (1992) *Biochemistry* 31:1579, Hollinger et al. (1993), *PNAS. USA* 90:6444, Gruber et al. (1994) *J. Immunol.* 152:5368, Zhu et al. (1997) *Protein Sci.* 6:781, Hu et al. (1996) *Cancer Res.* 56:3055, Adams et al. (1993) *Cancer Res.* 53:4026, and McCartney, et al. (1995) *Protein Eng.* 8:301.

For specific proteins described herein (e.g., Cas9), the named protein includes any of the protein's naturally occurring forms, or variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference or functional fragment or homolog thereof.

Thus, a "CRISPR associated protein 9," "Cas9" or "Cas9 protein" as referred to herein includes any of the recombinant or naturally-occurring forms of the Cas9 endonuclease or variants or homologs thereof that maintain Cas9 endonuclease enzyme activity (e.g. within at least 50%, 80%, 90%, 95%, 96%, 97%, 98%, 99% or 100% activity compared to Cas9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cas9 protein. In embodiments, the Cas9 protein is substantially identical to the protein identified by the UniProt reference number Q99ZW2 or a variant or homolog having substantial identity thereto. Cas9 refers to the protein also known in the art as "nickase". In embodiments, Cas9 binds a CRISPR (clustered regularly interspaced short palindromic repeats) nucleic acid sequence. In embodiments, the CRISPR nucleic acid sequence is a prokaryotic nucleic acid sequence.

As used herein, the term "lipid" refers to lipid molecules that can include fats, waxes, steroids, cholesterol, fat-soluble vitamins, monoglycerides, diglycerides, phospholipids, sphingolipids, glycolipids, cationic or anionic lipids, derivatized lipids, and the like, as described in detail below.

Suitable phospholipids include but are not limited to phosphatidylcholine (PC), phosphatidic acid (PA), phosphatidylethanolamine (PE), phosphatidylglycerol (PG), phosphatidylserine (PS), and phosphatidylinositol (PI), dimyristoyl phosphatidyl choline (DMPC), distearoyl phosphatidyl choline (DSPC), dioleoyl phosphatidyl choline (DOPC), dipalmitoyl phosphatidyl choline (DPPC), dimyristoyl phosphatidyl glycerol (DMPG), distearoyl phosphatidyl glycerol (DSPG), dioleoyl phosphatidyl glycerol (DOPG), dipalmitoyl phosphatidyl glycerol (DPPG), dimyristoyl phosphatidyl serine (DMPS), distearoyl phosphatidyl serine (DSPS), dioleoyl phosphatidyl serine (DOPS), dipalmitoyl phosphatidyl serine (DPPS), dioleoyl phosphatidyl ethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), di stearoylphosphatidyl-ethanolamine (DSPE), 16-O-monomethyl PE, 16-O-dimethyl PE, 18-1-trans PE, 1-stearoyl-2-oleoyl-phosphatidyethanolamine (SOPE), 1,2-dielaidoyl-sn-glycero-3-phophoethanolamine (transDOPE), and cardiolipin. In some embodiments, the phospholipid is DOPE. In other embodiments, the phospholipid is DSPC. Lipid extracts, such as egg PC, heart extract, brain extract, liver extract, and soy PC, are also useful in the present invention. In some embodiments, soy PC can include Hydro Soy PC (HSPC). In certain embodiments, the lipids can include derivatized lipids, such as PEGylated lipids. Derivatized lipids can include, for example, DSPE-PEG2000, cholesterol-PEG2000, DSPE-polyglycerol, or other derivatives generally known in the art.

Cationic lipids contain positively charged functional groups under physiological conditions. Cationic lipids include, but are not limited to, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N-[1-(2,3,-ditetradecyloxy)propyl]-N,N-dimethyl-N-hydroxyethylammonium bromide (DMRIE), N-[1-((2,3,dioleyloxy)propyl]-N,N-dimethyl-N-hydroxyethylammonium bromide (DORIE), 3β-[N—(N',N'-dimethylaminoethane) carbamoyl]cholesterol (DC-Chol), dimethyldioctadecylammonium (DDAB) and N,N-dimethyl-2,3-dioleyloxy)propylamine (DODMA).

Lipids can form micelles, monolayers, and bilayer membranes. The lipids can self-assemble into liposomes or lipid aggregates.

The term "lipid aggregate-forming cationic lipid" and the like refer, in the usual and customary sense, to a net positively charged lipid which can facilitate the formation of lipid aggregates. The term "lipid aggregate" refers to a lipid structure including a plurality of lipids or type of lipids, forming a higher order structure (e.g., secondary, tertiary or quaternary structure). Non-limiting examples of lipid aggregates include liposomes, unilamellar vesicles, multilamellar vesicles, micelles, amorphous aggregates, and the like. The lipid aggregates of the present invention can contain any suitable lipid, including cationic lipids, zwitterionic lipids, neutral lipids, or anionic lipids. In embodiments, the lipid aggregate includes a cationic lipid or a cationic lipid type. In embodiments, the lipid aggregate includes a cationic lipid or a cationic lipid type in combination with a non-cationic (e.g., neutral) lipid or a non-cationic lipid type. In embodiments, the lipid aggregate has a net positive charge. In embodiments, the lipid aggregate includes a cationic lipid and a neutral lipid. In embodiments, the lipid aggregate-forming cationic lipid is a cationic lipid as described in U.S. Pat. No. 8,785,200 which is hereby incorporated by reference and for all purposes.

In embodiments, the lipid aggregate includes a single lipid. In embodiments, the lipid aggregate includes a plurality of different lipids. Where the lipid aggregate includes a plurality of different lipids the lipid aggregate may include a lipid blend. A "lipid blend" as provided herein is a mixture of a plurality of lipid types. In embodiments, the lipid blend includes a first lipid type, a second lipid type or a third lipid type. The first, second and third lipid type may be independently different (e.g., cationic lipid and non-cationic lipid). Therefore, a person having ordinary skill in the art will immediately recognize that the terms "lipid" and "lipid type(s)" have the same meaning and can be used interchangeably.

As used herein, the term "liposome" encompasses any compartment enclosed by a lipid bilayer. The term liposome includes unilamellar vesicles which are comprised of a single lipid bilayer and generally have a diameter in the range of about 20 to about 400 nm. Liposomes can also be multilamellar having a diameter in the range of approximately 1 μm to approximately 10 μm. Multilamellar liposomes may consist of several (anywhere from two to hundreds) unilamellar vesicles forming one inside the other in diminishing size, creating a multilamellar structure of concentric phospholipid spheres separated by layers of water. Alternatively, multilamellar liposomes may consist of many smaller non concentric spheres of lipid inside a large liposome. In embodiments, liposomes include multilamellar vesicles (MLV), large unilamellar vesicles (LUV), and small unilamellar vesicles (SUV). The liposomes of the present invention can contain any suitable lipid, including cationic lipids, zwitterionic lipids, neutral lipids, or anionic lipids.

The term "nuclear localization signal sequence" or "NLS" as provided herein refer to a polypeptide sequence or a plurality of polypeptide sequences that identify a peptide or protein to which the NLS is attached for import into the cell nucleus by nuclear transport. A NLS may include one or more short sequences of positively charged amino acid residues (e.g., lysines or arginines) exposed on the protein surface. In embodiments, the NLS includes the sequence PKKKRKV (SEQ ID NO:47). In embodiments, the NLS has the sequence PKKKRKV (SEQ ID NO:47).

Compositions

Provided herein are, inter alia, compositions and methods to deliver ribonucleoprotein complexes (e.g., Cas9/gRNA) into a cell at high efficiencies. The compositions and methods provided herein are surprisingly effective in delivering ribonucleoprotein complexes into pluripotent stem cells and lymphoid cells. The compositions provided herein include a ribonucleoprotein complex, a lipid aggregate-forming cationic lipid and an enhancer element.

A "ribonucleoprotein complex," or "ribonucleoprotein particle" as provided herein refers to a complex or particle including a nucleoprotein and a ribonucleic acid. A "nucleoprotein" as provided herein refers to a protein capable of binding a nucleic acid (e.g., RNA, DNA). Where the nucleoprotein binds a ribonucleic acid it is referred to as "ribonucleoprotein." The interaction between the ribonucleoprotein and the ribonucleic acid may be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, the ribonucleoprotein includes an RNA-binding motif non-covalently bound to the ribonucleic acid. For example, positively charged aromatic amino acid residues (e.g., lysine residues) in the RNA-binding motif may form electrostatic interactions with the negative nucleic acid phosphate backbones of the RNA, thereby forming a ribonucleoprotein complex. Non-limiting examples of ribonucleoproteins include ribosomes, telomerase, RNAseP, hnRNP, CRISPR associated protein 9 (Cas9) and small nuclear RNPs (snRNPs). The ribonucleoprotein may be an enzyme. In embodiments, the ribonucleoprotein is an endonuclease. Thus, in embodiments, the ribonucleoprotein complex includes an endonuclease and a ribonucleic acid. In embodiments, the endonuclease is a CRISPR associated protein 9.

In embodiments, the CRISPR associated protein 9 is bound to a ribonucleic acid thereby forming a ribonucleoprotein complex. In embodiments, the ribonucleic acid is a guide RNA. Thus, in embodiments, the endonuclease is Cas9 and the ribonucleic acid is a guide RNA. A "guide RNA" or "gRNA" as provided herein refers to a ribonucleotide sequence capable of binding a nucleoprotein, thereby forming ribonucleoprotein complex. In embodiments, the guide RNA includes one or more RNA molecules. In embodiments, the gRNA includes a nucleotide sequence complementary to a target site. The complementary nucleotide sequence may mediate binding of the ribonucleoprotein complex to said target site thereby providing the sequence specificity of the ribonucleoprotein complex. Thus, in embodiments, the guide RNA is complementary to a target nucleic acid. In embodiments, the guide RNA binds a target nucleic acid sequence. In embodiments, the guide RNA is complementary to a CRISPR nucleic acid sequence. In embodiments, the complement of the guide RNA has a sequence identity of about 50%, 55%, 60%, 65%, 70%, 75%, 80%, 85%, 90%, 95%, 96%, 97%, 98% or 99% to a target nucleic acid. A target nucleic acid sequence as provided herein is a nucleic acid sequence expressed by a cell. In embodiments, the target nucleic acid sequence is an exogenous nucleic acid sequence. In embodiments, the target nucleic acid sequence is an endogenous nucleic acid sequence. In embodiments, the target nucleic acid sequence forms part of a cellular gene. Thus, in embodiments, the guide RNA is complementary to a cellular gene or fragment thereof. In embodiments, the guide RNA is about 50%, 55%, 60%, 65%, 70%, 75%, 80%, 85%, 90%, 95%, 96%, 97%, 98% or 99% to the target nucleic acid sequence. In embodiments, the guide RNA is about 50%, 55%, 60%, 65%, 70%, 75%, 80%, 85%, 90%, 95%, 96%, 97%, 98% or 99% complementary to the sequence of a cellular gene. In embodiments, the guide RNA binds a cellular gene sequence.

In embodiments, the guide RNA is a single-stranded ribonucleic acid. In embodiments, the guide RNA is about 10, 20, 30, 40, 50, 60, 70, 80, 90, 100 or more nucleic acid residues in length. In embodiments, the guide RNA is from about 10 to about 30 nucleic acid residues in length. In embodiments, the guide RNA is about 20 nucleic acid residues in length. In embodiments, the length of the guide RNA acid can be at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleic acid residues or sugar residues in length. In embodiments, the guide RNA is from 5 to 50, 10 to 50, 15 to 50, 20 to 50, 25 to 50, 30 to 50, 35 to 50, 40 to 50, 45 to 50, 5 to 75, 10 to 75, 15 to 75, 20 to 75, 25 to 75, 30 to 75, 35 to 75, 40 to 75, 45 to 75, 50 to 75, 55 to 75, 60 to 75, 65 to 75, 70 to 75, 5 to 100, 10 to 100, 15 to 100, 20 to 100, 25 to 100, 30 to 100, 35 to 100, 40 to 100, 45 to 100, 50 to 100, 55 to 100, 60 to 100, 65 to 100, 70 to 100, 75 to 100, 80 to 100, 85 to 100, 90 to 100, 95 to 100, or more residues in length. In embodiments, the guide RNA is from 10 to 15, 10 to 20, 10 to 30, 10 to 40, or 10 to 50 residues in length.

The compositions provided herein include a lipid aggregate-forming cationic lipid as described herein. In embodiments, the lipid aggregate-forming cationic lipid has the structure of formula:

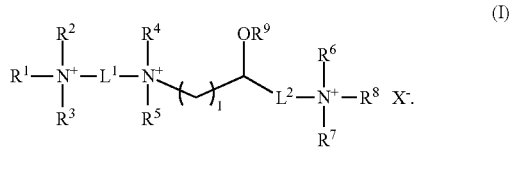

(I)

With respect to Formula (I), $R^1$, $R^2$, $R^3$, $R^4$, $R^5$, $R^6$, $R^7$, $R^8$ and $R^9$ are independently hydrogen, halogen, —$CY_3$, —CN, —C(O)OH, —$CH_2$C(O)OH, —C(O)$NH_2$, —OH, —SH, —$SO_2$Cl, —$SO_3$H, —$SO_4$H, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $L^1$ and $L^2$ are independently —C(O)—, —C(O)O—, —OC(O)—, —C(O)NH—, —NH—, —NHC(O)—, —O—, —S—, —S(O)—, —S(O)$_2$NH—, —NHS(O)$_2$—, substituted or unsubstituted alkylene or substituted or unsubstituted heteroalkylene. 1 is an integer from 1-8. $X^-$ is an anion; and Y is —F, —Cl, —Br, or —I.

In embodiments, $R^1$ is hydrogen or substituted or unsubstituted heteroalkyl. In embodiments, $R^1$ is substituted or unsubstituted heteroalkyl. In embodiments, $R^1$ is substituted heteroalkyl. In embodiments, $R^1$ is unsubstituted 2-8 membered heteroalkyl. In embodiments, $R^1$ is unsubstituted 2-6 membered heteroalkyl. In embodiments, le is unsubstituted 4-membered heteroalkyl. In embodiments, $R^1$ is —$CH_2$CH(OH)$CH_2NH_3^+$. In embodiments, $R^1$ is hydrogen.

In embodiments, $R^2$ is hydrogen or substituted or unsubstituted alkyl. In embodiments, $R^2$ is hydrogen.

In embodiments, $R^3$ and $R^4$ are independently substituted or unsubstituted alkyl. In embodiments, $R^3$ and $R^4$ are independently unsubstituted alkyl. $R^3$ and $R^4$ are independently unsubstituted $C_1$-$C_{20}$ alkyl. $R^3$ and $R^4$ are independently unsubstituted $C_5$-$C_{20}$ alkyl. $R^3$ and $R^4$ are independently unsubstituted $C_{10}$-$C_{20}$ alkyl. $R^3$ is unsubstituted $C_{14}$ alkyl. $R^4$ is unsubstituted $C_{14}$ alkyl.

In embodiments, $R^5$, $R^6$, $R^7$, $R^8$ and $R^9$ are independently hydrogen or substituted or unsubstituted alkyl. In embodiments, $R^5$, $R^6$, $R^7$, $R^8$ and $R^9$ are hydrogen.

In embodiments, $L^1$ is substituted or unsubstituted alkylene. In embodiments, $L^1$ is unsubstituted alkylene. In embodiments, $L^1$ is unsubstituted $C_1$-$C_{20}$ alkylene. In embodiments, $L^1$ is unsubstituted $C_1$-$C_{15}$ alkylene. In embodiments, $L^1$ is unsubstituted $C_1$-$C_{10}$ alkylene. In embodiments, $L^1$ is unsubstituted butylene.

In embodiments, $L^2$ is substituted or unsubstituted alkylene. In embodiments, $L^2$ is unsubstituted alkylene. In embodiments, $L^2$ is unsubstituted $C_1$-$C_{20}$ alkylene. In embodiments, $L^2$ is unsubstituted $C_1$-$C_{15}$ alkylene. In embodiments, $L^2$ is unsubstituted $C_1$-$C_{10}$ alkylene. In embodiments, $L^1$ is methylene.

In embodiments, 1 is 1, 2, 3, 4, 5, 6, 7 or 8. In embodiments, 1 is 1. In embodiments, 1 is 2. In embodiments, 1 is 3. In embodiments, 1 is 4. In embodiments, 1 is 5. In embodiments, 1 is 6. In embodiments, 1 is 7. In embodiments, 1 is 8.

In embodiments, the lipid aggregate-forming cationic lipid has the structure of formula:

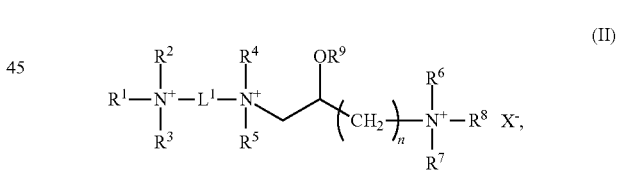

(II)

wherein n is an integer from 1-6.

For the embodiments of formula (II), $R^1$, $R^2$, $R^3$, $R^4$, $R^5$, $R^6$, $R^7$, $R^8$ and $R^9$ are defined as described above. For example, le is unsubstituted 4-membered heteroalkyl; $R^2$ is hydrogen or substituted or unsubstituted alkyl; $R^3$ and $R^4$ are independently substituted or unsubstituted alkyl; $R^5$, $R^6$, $R^7$, $R^8$ and $R^9$ are hydrogen; and $L^1$ is substituted or unsubstituted alkylene. In embodiments, n is 1, 2, 3, 4, 5, or 6. In embodiments, n is 1. In embodiments, n is 2. In embodiments, n is 3. In embodiments, n is 4. In embodiments, n is 5. In embodiments, n is 6.

In embodiments, the lipid aggregate-forming cationic lipid has the structure of formula:

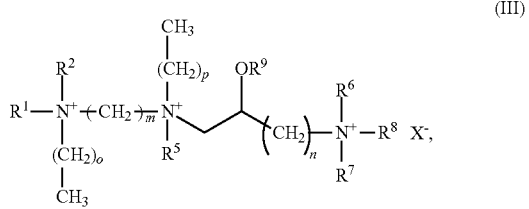

(III)

wherein m is an integer from 1-10; and o and p are independently integers from 8-30. For the embodiments of formula (III), $R^1$, $R^2$, $R^5$, $R^6$, $R^7$, $R^8$ and $R^9$ are defined as described above. For example, $R^1$ is unsubstituted 4-membered heteroalkyl; $R^2$ is hydrogen or substituted or unsubstituted alkyl; and $R^5$, $R^6$, $R^7$, $R^8$ and $R^9$ are hydrogen. In embodiments, m is 1, 2, 3, 4, 5, 6, 7, 8, 9, or10. In embodiments, m is 1. In embodiments, m is 2. In embodiments, m is 3. In embodiments, m is 4. In embodiments, m is 5. In embodiments, m is 6. In embodiments, m is 7. In embodiments, m is 8. In embodiments, m is 9. In embodiments, m is 10. In embodiments, o and p are independently 8, 9, 10, 11, 12, 13, 14, 15, 16, 17, 18, 19, 20, 21, 22, 23, 24, 25, 26, 27, 28, 29, or 30. In embodiments, o and p are independently 8. In embodiments, o and p are independently 9. In embodiments, o and p are independently 10. In embodiments, o and p are independently 11. In embodiments, o and p are independently 12. In embodiments, o and p are independently 13. In embodiments, o and p are independently 14. In embodiments, o and p are independently 15. In embodiments, o and p are independently 16. In embodiments, o and p are independently 17. In embodiments, o and p are independently 18. In embodiments, o and p are independently 19. In embodiments, o and p are independently 20.

The term "enhancer element" as provided herein refers to a peptide which facilitates transfection, thereby increasing transfection efficiency. Therefore, the transfection efficiency of a nucleic acid, polypeptide or complex thereof into a cell is higher in the presence of an enhancer element compared to the transfection efficiency in the absence of said enhancer element. In embodiments, the enhancer element is a peptide including one or more cationic moieties. In embodiments, the enhancer element is a peptide. In embodiments, the one or more cationic moieties are attached to the C-terminus of the enhancer element. In embodiments, the one or more cationic moieties are attached to the N-terminus of the enhancer element. The enhancer element may include a polyamine moiety covalently attached to a nuclear localization signal sequence. A polyamine moiety as provided herein is a monovalent polyamine. In embodiments, the polyamine moiety is a spermine moiety. The term "spermine" as provided herein refers in a customary sense to the compound identified by CAS registry No. 71-44-3. In embodiments, the polyamine moiety is an analog of spermine with one or more substituents covalently bound to a spermine core. In embodiments, the polyamine moiety is a plurality of spermine moieties. In embodiments, the polyamine moiety is 4 or more spermine moieties. In embodiments, the polyamine moiety is six spermine moieties. In embodiments, the polyamine moiety is attached to the N-terminus of the enhancer element. In embodiments, the polyamine moiety is attached to the C-terminus of the enhancer element.

In embodiments, the enhancer element includes one nuclear localization signal (NLS) sequence. In embodiments, the enhancer element includes at least two nuclear localization signal (NLS) sequences. The enhancer element provided herein may be any peptide useful in delivering a nucleic acid, a nucleoprotein or a ribonucleoprotein complex into a cell. For example, an enhancer element useful for the invention provided herein may be any peptide disclosed in U.S. Pat. No. 8,058,068, which is hereby incorporated by reference and for all purposes.

In embodiments, the enhancer element includes the sequence of SEQ ID NO:1-SEQ ID NO:46. In embodiments, the enhancer element is the sequence of SEQ ID NO:1-SEQ ID NO:46 In embodiments, the enhancer element includes the sequence of SEQ ID NO:1. In embodiments, the enhancer element includes the sequence of SEQ ID NO:2. In embodiments, the enhancer element includes the sequence of SEQ ID NO:3. In embodiments, the enhancer element includes the sequence of SEQ ID NO:4. In embodiments, the enhancer element includes the sequence of SEQ ID NO:5. In embodiments, the enhancer element includes the sequence of SEQ ID NO:6. In embodiments, the enhancer element includes the sequence of SEQ ID NO:7. In embodiments, the enhancer element includes the sequence of SEQ ID NO:8. In embodiments, the enhancer element includes the sequence of SEQ ID NO:9. In embodiments, the enhancer element includes the sequence of SEQ ID NO:10. In embodiments, the enhancer element includes the sequence of SEQ ID NO:11. In embodiments, the enhancer element includes the sequence of SEQ ID NO:12. In embodiments, the enhancer element includes the sequence of SEQ ID NO:13. In embodiments, the enhancer element includes the sequence of SEQ ID NO:14. In embodiments, the enhancer element includes the sequence of SEQ ID NO:15. In embodiments, the enhancer element includes the sequence of SEQ ID NO:16. In embodiments, the enhancer element includes the sequence of SEQ ID NO:17. In embodiments, the enhancer element includes the sequence of SEQ ID NO:18. In embodiments, the enhancer element includes the sequence of SEQ ID NO:19. In embodiments, the enhancer element includes the sequence of SEQ ID NO:20.

In embodiments, the enhancer element includes the sequence of SEQ ID NO:21. In embodiments, the enhancer element includes the sequence of SEQ ID NO:22. In embodiments, the enhancer element includes the sequence of SEQ ID NO:23. In embodiments, the enhancer element includes the sequence of SEQ ID NO:24. In embodiments, the enhancer element includes the sequence of SEQ ID NO:25. In embodiments, the enhancer element includes the sequence of SEQ ID NO:26. In embodiments, the enhancer element includes the sequence of SEQ ID NO:27. In embodiments, the enhancer element includes the sequence of SEQ ID NO:28. In embodiments, the enhancer element includes the sequence of SEQ ID NO:29. In embodiments, the enhancer element includes the sequence of SEQ ID NO:30. In embodiments, the enhancer element includes the sequence of SEQ ID NO:31. In embodiments, the enhancer element includes the sequence of SEQ ID NO:32. In embodiments, the enhancer element includes the sequence of SEQ ID NO:33. In embodiments, the enhancer element includes the sequence of SEQ ID NO:34. In embodiments, the enhancer element includes the sequence of SEQ ID NO:35.

In embodiments, the enhancer element includes the sequence of SEQ ID NO:36. In embodiments, the enhancer element includes the sequence of SEQ ID NO:37. In embodiments, the enhancer element includes the sequence of SEQ ID NO:38. In embodiments, the enhancer element includes the sequence of SEQ ID NO:39. In embodiments, the enhancer element includes the sequence of SEQ ID NO:40. In embodiments, the enhancer element includes the sequence of SEQ ID NO:41. In embodiments, the enhancer element includes the sequence of SEQ ID NO:42. In embodiments, the enhancer element includes the sequence of SEQ ID NO:43. In embodiments, the enhancer element includes the sequence of SEQ ID NO:44. In embodiments, the enhancer element includes the sequence of SEQ ID NO:45. In embodiments, the enhancer element includes the sequence of SEQ ID NO:46.

In embodiments, the composition further includes a neutral lipid. A "neutral lipid" as provided herein refers to a lipid capable of further increasing transfection efficiency of the compositions provided herein including embodiments thereof. Therefore, the transfection efficiency of a ribonucleoprotein complex, a lipid aggregate-forming cationic lipid and an enhancer element into a cell is higher in the presence of a neutral peptide compared to the transfection efficiency in the absence of said neutral peptide. Neutral lipids useful in this invention include, without limitation: lecithins; phosphotidylethanolamine; phosphatidylethanolamines, such as DOPE (dioleoylphosphatidylethanolamine), DPhPE (diphytanoylphosphatidylethanolamine), DPPE (dipalmitoylphosphatidylethanolamine), dipalmiteoylphosphatidylethanolamine, POPE (palmitoyloleoyl-phosphatidylethanolamine) and di stearoylphosphatidylethanolamine; phosphotidylcholine; phosphatidylcholines, such as DOPC (dioleoylphosphidylcholine), DPPC (dipalmitoylphosphatidylcholine) POPC (palmitoyloleoyl-phosphatidylcholine) and di stearoylphosphatidylcholine; phosphatidylglycerol; phosphatidylglycerols, such as DOPG (dioleoylphosphatidylglycerol), DPPG (dipalmitoylphosphatidyl-glycerol), and distearoylphosphatidylglycerol; phosphatidylserine; phosphatidylserines, such as dioleoyl- or dipalmitoylphosphatidylserine; diphosphatidylglycerols; fatty acid esters; glycerol esters; sphingolipids; cardolipin; cerebrosides; and ceramides; and mixtures thereof. Neutral lipids also include cholesterol and other 3.beta.OH-sterols.

In embodiments, the composition further includes a donor nucleic acid. A donor nucleic acid as provided herein is a nucleic acid including a sequence having at least 50%, 60%, 70%, 80%, 90%, 95%, 96%, 97%, 98%, or 99% sequence identity to a target nucleic acid sequence. In embodiments, the donor nucleic acid has at least 50%, 60%, 70%, 80%, 90%, 95%, 96%, 97%, 98%, or 99% sequence identity to a target nucleic acid sequence. In embodiments, the complement of the donor nucleic acid has at least 50%, 60%, 70%, 80%, 90%, 95%, 96%, 97%, 98%, or 99% sequence identity to a target nucleic acid sequence. In embodiments, the donor sequence includes a PCR amplified nucleic acid sequence. In embodiments, the donor nucleic acid is derived from a plasmid.

In embodiments, the composition further includes a eukaryotic cell. In embodiments, the eukaryotic cell is a pluripotent cell, a lymphatic cell or a hepatocyte. In embodiments, the eukaryotic cell is a pluripotent cell. In embodiments, the eukaryotic cell is a lymphatic cell. In embodiments, the eukaryotic cell is a hepatocyte. In embodiments, the pluripotent cell is an induced pluripotent cell or an embryonic stem cell. In embodiments, the pluripotent cell is an induced pluripotent cell. In embodiments, the pluripotent cell is an embryonic stem cell. In embodiments, the lymphatic cell is a T cell.

In embodiments, the composition further includes a cell culture. A cell culture as provided herein refers to an environment including appropriate cellular nutrients and capable of maintaining cells in vitro. The environment may be a liquid environment, a solid environment and/or a semisolid environment (e.g. agar, gel etc.) in an appropriate vessel (e.g., cell culture dish). A cell culture medium may be employed. A "cell culture medium" as used herein, is used according to its generally accepted meaning in the art. A cell culture medium (also referred to in the art and herein as a "culture medium") includes liquids (e.g., growth factors, minerals, vitamins etc.) or gels designed to support the growth (e.g. division, differentiation, maintenance etc.) of cells. In embodiments, the compositions provided herein including embodiments, further include a physiologically acceptable solution. A "physiologically acceptable solution" as provided herein refers to any acceptable aqueous solution (e.g., buffer) in which the compositions provided herein may be contained without losing their biological properties. In embodiments, the physiologically acceptable solution is a cell culture medium.

Methods.

The methods provided herein are, inter alfa, useful for the efficient delivery of ribonucleoprotein complexes into cells (e.g., pluripotent cells). The method of forming a cell transfection composition includes contacting a ribonucleic acid, an endonuclease and an enhancer element, thereby forming a ribonucleoprotein-enhancer element complex. The method further includes contacting a lipid aggregate-forming cationic lipid with the ribonucleoprotein-enhancer element complex, thereby forming a cell transfection composition. The cell transfection composition is delivered to cells at an unexpectedly high efficiency.

The ribonucleic acid (e.g., gRNA) may be contacted with the endonuclease (e.g., Cas9), thereby forming a ribonucleoprotein. The ribonucleoprotein may then be contacted with an enhancer element, thereby forming a ribonucleoprotein-enhancer element complex. Thus, in embodiments, the step of contacting a ribonucleic acid, an endonuclease and an enhancer element includes contacting the ribonucleic acid with the endonuclease, thereby forming a ribonucleoprotein. In embodiments, the ribonucleoprotein is contacted with the enhancer element, thereby forming the ribonucleoprotein-enhancer element complex. In embodiments, the step of contacting a ribonucleic acid, an endonuclease and an enhancer element includes the steps of contacting the ribonucleic acid with the endonuclease, thereby forming a ribonucleoprotein; and contacting the ribonucleoprotein with the enhancer element, thereby forming the ribonucleoprotein-enhancer element complex. In embodiments, the ribonucleoprotein-enhancer element complex is in a first vessel and the lipid aggregate-forming cationic lipid is in a second vessel. In embodiments, the ribonucleoprotein-enhancer element complex is contacted with the lipid aggregate-forming cationic lipid in the second vessel. In embodiments, the ribonucleoprotein-enhancer element complex is contacted with the lipid aggregate-forming cationic lipid in the first vessel. In embodiments, the contacting a ribonucleic acid, an endonuclease and an enhancer element further includes contacting a neutral peptide.

Further to any method of forming a cell transfection composition disclosed above, in embodiments, the step of contacting a ribonucleic acid, an endonuclease and an enhancer element is in a physiologically acceptable solution. In embodiments, the step of contacting a lipid aggregate-forming cationic lipid with the ribonucleoprotein-enhancer element complex is in a physiologically acceptable solution. In embodiments, the physiologically acceptable solution is a cell culture medium.

For the methods provided herein any of the compositions (e.g., ribonucleic acid, endonuclease, an enhancer element, lipid aggregate-forming cationic lipid, donor DNA, neutral lipid) described above including embodiments thereof may be used. Thus, in embodiments the endonuclease is CRISPR associated protein 9 (Cas9) and the ribonucleic acid is a guide RNA. In embodiments, the ribonucleic acid is a guide RNA.

In embodiments, the lipid aggregate-forming cationic lipid has the structure of formula:

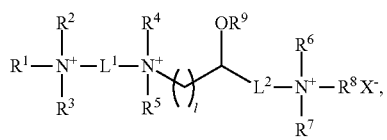

(I)

wherein $R^1$, $R^2$, $R^3$, $R^4$, $R^5$, $R^6$, $R^7$, $R^8$ and $R^9$ are independently hydrogen, halogen, —$CY_3$, —CN, —C(O)OH, —$CH_2C(O)OH$, —$C(O)NH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC═(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $L^1$ and $L^2$ are independently —C(O)—, —C(O)O—, —OC(O)—, —C(O)NH—, —NH—, —NHC(O)—, —O—, —S—, —S(O)—, —S(O)$_2$NH—, —NHS(O)$_2$—, substituted or unsubstituted alkylene or substituted or unsubstituted heteroalkylene. l is an integer from 1-8. $X^-$ is an anion. Y is —F, —Cl, —Br, or —I.

In embodiments, the lipid aggregate-forming cationic lipid has the structure of formula:

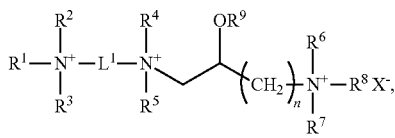

(II)

wherein n is an integer from 1-6.

In embodiments, the lipid aggregate-forming cationic lipid has the structure of formula:

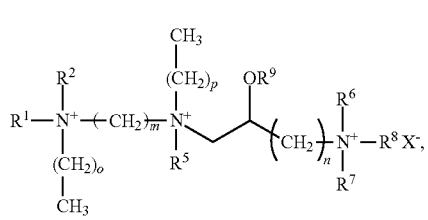

(III)

wherein m is an integer from 1-10; and o and p are independently integers from 8-30.

In embodiments, 1e is substituted or unsubstituted heteroalkyl.

In embodiments, the enhancer element is a peptide. In embodiments, the enhancer element includes a polyamine moiety covalently attached to a nuclear localization signal sequence. In embodiments, the polyamine moiety is a spermine moiety. In embodiments, the polyamine moiety is a plurality of spermine moieties. In embodiments, the polyamine moiety is attached to the N-terminus of the enhancer element. In embodiments, the enhancer element includes the sequence of SEQ ID NO:1-SEQ ID NO:46 In embodiments, the enhancer element includes a nuclear localization signal (NLS) sequence. In embodiments, the enhancer element includes at least two nuclear localization signal (NLS) sequences.

Further to the method disclosed above, in embodiments the method further includes, prior to the step of contacting a lipid aggregate-forming cationic lipid with the ribonucleoprotein-enhancer element complex, the step of contacting the ribonucleoprotein-enhancer element complex with a donor nucleic acid.

In another aspect, there is provided a method of forming a cell transfection composition. The method includes the steps: (i) contacting a lipid aggregate-forming cationic lipid with a cell culture medium in a first reaction vessel, thereby forming a lipid aggregate-forming cationic lipid medium; (ii) contacting a ribonucleic acid, an endonuclease and an enhancer element in a second reaction vessel, thereby forming a ribonucleoprotein-enhancer element complex; and (iii) contacting the lipid aggregate-forming cationic lipid medium with the ribonucleoprotein-enhancer element complex in the second reaction vessel, thereby forming a cell transfection composition.

In embodiments, the method further includes, prior to contacting in step (iii), contacting the ribonucleoprotein-enhancer element complex with a donor nucleic acid.

In another aspect, there is provided a method of forming a cell transfection composition. The method includes the steps: (i) contacting a ribonucleic acid, an endonuclease and an enhancer element in a first reaction vessel, thereby forming a ribonucleoprotein-enhancer element complex; (ii) contacting a lipid aggregate-forming cationic lipid with a cell culture medium in a second reaction vessel, thereby forming a lipid aggregate-forming cationic lipid medium; and (iii) contacting the ribonucleoprotein-enhancer element complex with the lipid aggregate-forming cationic lipid medium in the second reaction vessel, thereby forming a cell transfection composition.

Further to methods of forming a cell transfection composition disclosed above, in embodiments the ribonucleoprotein complex includes an endonuclease and a ribonucleic acid. In embodiments, the endonuclease is CRISPR associated protein 9 (Cas9) and the ribonucleic acid is a guide RNA.

In embodiments, the lipid aggregate-forming cationic lipid has the structure of formula:

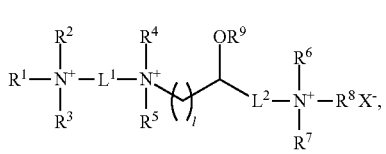

(I)

wherein $R^1$, $R^2$, $R^3$, $R^4$, $R^5$, $R^6$, $R^7$, $R^8$ and $R^9$ are independently hydrogen, halogen, —$CY_3$, —CN, —C(O)OH, —$CH_2C(O)OH$, —$C(O)NH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC═(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $L^1$ and $L^2$ are independently —C(O)—, —C(O)O—, —OC(O)—, —C(O)NH—, —NH—, —NHC(O)—, —O—, —S—, —S(O)—, —S(O)$_2$NH—, —NHS(O)$_2$—, substituted or unsubstituted alkylene or substituted or unsubstituted heteroalkylene. 1 is an integer from 1-8. X$^-$ is an anion. Y is —F, —Cl, —Br, or —I.

In embodiments, the lipid aggregate-forming cationic lipid has the structure of formula:

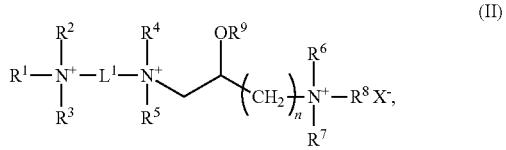

(II)

wherein n is an integer from 1-6.

In embodiments, the lipid aggregate-forming cationic lipid has the structure of formula:

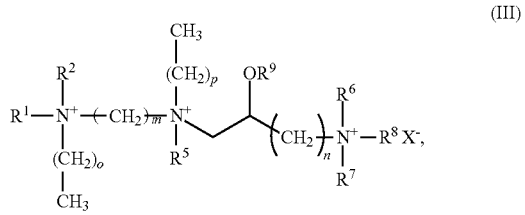

(III)

wherein m is an integer from 1-10; and o and p are independently integers from 8-30.

In embodiments, the enhancer element is a peptide. In embodiments, the enhancer element includes a polyamine moiety covalently attached to a nuclear localization signal sequence. In embodiments, the polyamine moiety is a spermine moiety. In embodiments, the polyamine moiety is a plurality of spermine moieties. In embodiments, the polyamine moiety is attached to the N-terminus of the enhancer element.

Further to methods of forming a cell transfection composition disclosed above, in embodiments the enhancer element comprises the sequence of SEQ ID NO:1-SEQ ID NO:46. In embodiments, the enhancer element includes at least two nuclear localization signal (NLS) sequences.

In another aspect, there is provided an in vitro cell culture including a eukaryotic cell, a ribonucleoprotein complex, a lipid aggregate-forming cationic lipid and an enhancer element.

In embodiments, the eukaryotic cell is a pluripotent cell, a lymphatic cell or a hepatocyte. In embodiments, the pluripotent cell is an induced pluripotent cell or an embryonic stem cell. In embodiments, the lymphatic cell is a T cell. In embodiments, the culture is from about 20% to about 60% confluent, e.g., about 20%, 25%, 30%, 35%, 40%, 45%, 50%, 55%, or even about 60% confluent. In embodiments, the culture is less than about 40% confluent. In embodiments, the culture is about 30% confluent. In embodiments, the culture is about 40% confluent. In embodiments, the viability of the cell culture is at least about 60%, 70%, 80%, 90%, 95% or 99%.

In another aspect, there is provided a method of transfecting a ribonucleoprotein complex into a cell. The method includes contacting a cell with the composition as disclosed above. In embodiments, the method includes, prior to contacting step, forming a cell transfection composition as set forth above.

EXAMPLES

Example 1. Novel Transfection Reagent for the Efficient Delivery of Cas9 Protein/gRNA Complexes Recent advances in CRISPR technology have enabled researchers to engineer cells and circuits efficiently in vivo. However, the potential off-target effects of Cas9 nuclease remain a major concern for therapeutic applications. Recently, the delivery of purified Cas9 protein and gRNA complexes (Cas9 RNPs) has gained increasing attention due to high editing efficiency and reduced off-target effects. Although Cas9 RNPs can be delivered into mammalian cells via electroporation with relatively high efficiency, lipid-mediated transfection remains popular due to ease of use, low cost, and adaptation to high throughput systems. Using a systematic approach, we screened more than 60 transfection reagents using six commonly-used mammalian cell lines and identified a novel reagent (named LIPOFECTAMINE® CRISPRMAX™) that could deliver Cas9 RNPs efficiently. The LIPOFECTAMINE® CRISPRMAX™-mediated transfection conditions were further optimized using a set of 23 adherent and suspension cell lines while electroporation was also carried out in the harder-to-transfect cells. The results indicated that the amount of transfection reagent and Cas9 RNPs as well as cell density were the key factors to achieve high efficiency of genome editing. Furthermore, a donor DNA could be co-delivered with Cas9RNP via LIPOFECTAMINE® CRISPRMAX™. The method described here will further facilitate high throughput genome modifications in various cell types.

A major challenge with efficient delivery of protein into mammalian cells is the poor permeability and high selectivity of the cellular membrane. The use of cell-penetrating peptides (CPPs) has been shown to facilitate the delivery of active proteins into cells [1-3]. Because of the recent advances of the CRISPR system in genome engineering, the delivery of purified Cas9 protein has become attractive due to the potentially lower off-target effect compared with plasmid DNA transfection [4-6]. Although Cas9 RNPs can be efficiently delivered into mammalian cells via electroporation, it requires specialized equipment and is relatively low throughput. Several methods for delivery of Cas9 RNPs have been reported recently such as a method termed iTOP (induced transduction by osmocytosis and propanebetaine). iTOP is based upon NaCl-mediated hyperosmolality in combination with a transduction compound propanebetaine, triggering macropinocytotic uptake and intracellular release of extracellularly applied macromolecules [7]. Also, by fusing to negatively supercharged GFP proteins or binding to anionic nucleic acids, functional proteins could be delivered into mammalian cells via cationic lipid-mediated transfection. As described, Cas9 RNPs delivered into U2OS cells using LIPOFECTAMINE® 2000 resulted in up to 80% modification efficiency at an integrated GFP reporter and into the mouse inner ear in vivo using LIPOFECTAMINE® RNAiMAX™ with 20% loss of GFP expression in auditory sensory cells [5]. However, significant toxicity from LIPOFECTAMINE® 2000 was also reported in U2OS cells. In the present study, we identified a new transfection reagent via screening and then optimized the transfection protocol using a set of 23 different cell lines.

Materials and Methods.

Materials. GIBCO® Human Episomal iPSC, GIBCO® Human Neural Stem Cells (H9-Derived), Human Epidermal Keratinocytes, mouse embryonic fibroblasts (MEF), mouse ESC, 293FT cells, HUVEC, DMEM medium, RPMI 1640 medium, IMDM, DMEM/F-12, KNOCKOUT™ DMEM, Non-essential amino acids solution, recombinant human LIF, KNOCKOUT™ Serum Replacement, McCoy's, Medium 200, EPILIFE® Medium, ESSENTIAL 8™ Medium, Fetal Bovine Serum (FBS), HKGS kit, GLUTAMAX™, LSGS Kit, TRYPLE™ Express Enzyme, GELTREX®, OPTI-MEM® Medium, FLUOROBRITE™ DMEM, LIPOFECTAMINE® 2000, LIPOFECTAMINE® 3000, LIPOFECTAMINE® RNAiMAX™, LIPOFECTAMINE® CRISPRMAX™, collection of 60 transfection reagents, JUMP-IN™ GRIPTITE™ HEK293 cells Retargeting Kit, NEON™ Transfection System 10 μL Kit, pJTI R4 EXP CMV EmGFP pA, pEF1-EmGFP, 2% E-GEL® EX Agarose Gels, TranscriptAid T7 High Yield Transcription Kit, MEGACLEAR™ Transcription Clean-Up Kit, QUBIT® RNA BR Assay Kit, GENEART® Genomic Cleavage Detection Kit, and purified PLATINUM™ Cas9 Nuclease were from Thermo Fisher Scientific. Jurkat T cells, K562 cells, 3T3, COS-7, CHO—S, N2A, A549, HEK293, HeLa, MCF-7, MDA-MB-231, U2OS, HepG2, SC-1, HCT116, NK-92, THP-1, and Raji cell lines were obtained from the American Type Culture Collection (ATCC). Guide RNAs (gRNAs) were synthesized via one-pot PCR assembly of a gRNA template followed by in vitro transcription [6]. CRISPR target sequences and primer sequences for amplification of the genomic locus are described in Table is following.

RPMI medium supplemented with 25% FBS, 1 mM sodium pyruvate, 10 mM HEPES and 0.1 mM β-mercaptoethanol. Mouse ESCs were cultured on MEF feeder layers using KNOCKOUT™ DMEM supplemented with 15% KNOCKOUT™ Serum Replacement, non-essential amino acids, L-glutamine, β-mercaptoethanol and 10 ng/ml recombinant human LIF. The GIBCO® iPSC line was maintained in ESSENTIAL 8™ Medium on GELTREX® matrix-coated culture vessels and passaged using 0.5 mM EDTA prepared in Dulbecco's Phosphate-Buffered Saline (DPBS) without calcium or magnesium. All the cells were incubated at 37° C. in a humidified 5% $CO_2$ incubator.

Systematic Design of Experiment. The screening of transfection reagents was conducted in a 96-well format. One day prior to transfection, six commonly used cell lines, A549, HEK293, Hela, HepG2, MCF-7, and U2OS, were seeded in 96-well plates at a density of 10,000 to 20,000 cells per well. On the day of transfection, a master mix of Cas9 protein and HPRT1 gRNA was prepared in OPTI-MEM® medium and incubated for 5 minutes at room temperature to form the Cas9 RNP complexes. The amount of Cas9 RNP complexes was held constant at 40 ng Cas9 and 8.5 ng gRNA per well. On the other hand, the amount of each transfection reagent, which was also prepared in OPTI-MEM® medium, varied from 0.1, 0.2, 0.4 and 0.6 μl per well. LIPOFECTAMINE® 3000 and LIPOFECTAMINE® RNAiMAX served as controls. The Cas9 RNP complexes in OPTI-MEM® medium were added to the transfection reagents diluted in OPTI-MEM® medium. The mixture was incubated at room temperature for 10 to 15 minutes to form the Cas9 RNP and transfection reagent complexes prior to addition to the cells. Upon incubation for 48 hours, the cells were lysed and percentage of Indel (insertion and deletion) was measured TABLE 1s CRISR target sequence and PCR Primers

| Species | Locus | target Sequence (5'->3') | SEQ ID NO: | Forward primer (5'->3') | SEQ ID NO: | Reverse primer (5'->3') | SEQ ID NO: |
|---|---|---|---|---|---|---|---|
| Human | HPRT1 | GCATTTCTCAGT CCTAAACAGGG | 48 | ACATCAGCAGCTGTTC TG | 49 | GGCTGAAAGGAGAG AACT | 50 |
| Hamster | COSMC | GAATATGTGAGT GTGGATGG | 51 | GGATCCATCGCAGCCT TTCT | 52 | ACTACCTGGTTCGGG TGGTT | 53 |
| Monkey | Nr0b1 | GGCGCTCAAGA GTCCACAGG | 54 | AGCATCCTCTACAGCT TGCTCAC | 55 | GGTACTGATGTTCAG ACTCCAGC | 56 |
| Mouse | Rosa26 | AGATGGGCGGG AGTCTTCTGGG | 57 | GGGCTGAGCGGCTGC GGGGCG | 58 | CTG TAG TAA GGA TCT CAA GCA GGA G | 59 |
| EmGFP | EmGFP gene | CCAGGGCACGG GCAGCTTGCCGG | 60 | ATGGTGAGCAAGGGC GAGGAGCTG | 61 | GTC CTC CTT GAA GTC GAT GCC C | 62 |

Cell culture. HEK293, 3T3, HeLa, MCF-7, MDA-MB-231, HepG2, COS-7, N2A, and A549 were grown in DMEM medium supplemented with 10% FBS. HCT116 and U2OS were cultured in McCoy's medium containing 10% FBS, while CHO cells were maintained in DMEM/F-12 plus 10% FBS. HUVEC cells were propagated in Medium 200 supplemented with LSGS. Human Epidermal Keratinocytes (HEKa) were maintained in EPILIFE® Medium supplemented with HKGS. Jurkat T cells, SC-1, THP-1, and Raji cells were grown in RPMI medium supplemented with 10% FBS, whereas K562 cells were maintained in IMDM medium containing 10% FBS. NK92 cells were grown on by GENEART® Genomic Cleavage Detection Kit. The experimental data was then analyzed using JMP 11 software.

Cell transfection in a 24-well plate. One day prior to transfection, adherent cells were plated onto 24-well plates at a density of 0.4 to 1.5×10^ cells per well in 500 μl of growth medium so that the cells density reached 30-70% confluence at the time of transfection. On the day of transfection, 25 μl of OPTI-MEM® was added to a 1.5 ml sterile Eppendorf tube, followed by addition of 500 ng recombinant Cas9 protein and 125 ng gRNA (approximately a 1:1.2 molar ratio). Upon mixing by briefly vortexing, 1 μl of Cas9 PLUS™ reagent was then added to the solution containing Cas9 protein and gRNA. After briefly vortexing, the mixture was incubated at room temperature for 5 minutes to allow Cas9 RNP complex formation. The Cas9 RNP complexes were stable at room temperature for up to 3 hours. For co-delivery of donor DNA, 500 ng plasmid DNA or linear PCR fragment was added to the Cas9 RNP complexes at this point. Meanwhile, 25 μl of OPTI-MEM® was added to a separate sterile Eppendorf tube, followed by addition of 1.5 μl of LIPOFECTAMINE® CRISPRMAX™. Upon briefly vortexing, the LIPOFECTAMINE® CRISPRMAX™ solution was incubated at room temperature for approximately 5 minutes. Upon incubation, the Cas9 RNP complexes were then added to the LIPOFECTAMINE® CRISPRMAX™ solution. The reverse addition of LIPOFECTAMINE® CRISPRMAX™ solution to Cas9 RNP complexes was found to decrease the editing efficiency in certain cell lines. Upon mixing, the sample was incubated at room temperature for 10 to 15 minutes to form Cas9 RNP and LIPOFECTAMINE® CRISPRMAX™ complexes and then added to the cells. At 48-72 hours post transfection, the cells were harvested for analysis of genome modification efficiency using GENEART® Genomic Cleavage Detection kit. Alternatively, cells were analyzed by flow cytometry to determine the percentage of EmGFP positive cells.

For transfection of the iPS cell line, the cells were treated with TRYPLE™ and plated onto GELTREX®-coated 24-well plates at a density of 40,000 cells per well, leading to approximately 30-40% confluence at the time of transfection. One microgram of Cas9 protein, 250 ng gRNA and 6 μl of Cas9 PLUS™ reagent were used to prepare the Cas9 RNP complexes instead, while the amount of LIPOFECTAMINE® CRISPRMAX™ reagent remained constant at 1.5 μl. At around 6 hours post transfection, the transfection reagent was removed and replaced with fresh ESSENTIAL 8™ Medium. The cells were analyzed at 48 hours post transfection.

A 'reverse' transfection protocol was tested using MCF-7 and HepG2 cells. As described above, the Cas9 RNP complexes and LIPOFECTAMINE® CRISPRMAX™ reagent were prepared in two separate tubes with 500 ng Cas9 protein, 125 ng gRNA, 1 μl Cas9 PLUS™ reagent, and 1.5 μl of LIPOFECTAMINE® CRISPRMAX™ reagent, respectively. The Cas9 RNP solution was then added to LIPOFECTAMINE® CRISPRMAX™ solution. Upon mixing, the mixture was incubated at room temperature for 10-15 minutes to form Cas9 RNP and LIPOFECTAMINE® CRISPRMAX™ complexes. Meanwhile, MCF-7 and HepG2 cells were detached with TrypLE™ and counted, followed by seeding at a density of 2×10^5 and 1.0×10^ cells per well, respectively. The Cas9 RNP/LIPOFECTAMINE® CRISPRMAX™ solution was then added directly to the cell suspension and incubated for 48-72 hours prior to analysis.

For NEON™ electroporation, adherent cells were detached from culture dishes and counted. In general, 1×10^5 adherent cells or 2×10^5 suspension cells were used per 10 μl reaction. For the NEON™ 24 optimization protocols, 24 μg Cas9 protein and 6 μg gRNA were added to 120 μl Resuspension Buffer R, followed by mixing and incubation at room temperature for 5 minutes to form the Cas9 RNP complexes. Meanwhile, 2.4×10^6 adherent cells or 4.8×10^6 suspension cells were harvested and washed with DPBS. After aspiration, the cell pellets were re-suspended in 120 μl Resuspension Buffer R and then mixed with Cas9 RNP complexes. A 10 μl sample was taken for electroporation using one of the NEON™ 24 optimization protocols. The electroporated cells were transferred immediately to a 24 well containing 0.5 ml of the corresponding growth medium and incubated for 48 hours prior to analysis. Upon optimization, the use of a higher dose of Cas9 RNP (for example, 2 μg Cas9 protein and 500 ng gRNA per reaction) could further increase the cleavage efficiency [6].

Generation of a disrupted EmGFP stable cell line. GRIPTITE™ HEK293 stable cells expressing EmGFP were prepared via the Jump-In™ system as described in the manual (Thermo Fisher Scientific). To generate a disrupted EmGFP mutant stable cell line, 1.5 μg of Cas9 protein was associated with 300 μg of gRNA targeting the 5'-ctcgtgaccaccttcactacgg-3' (SEQ ID NO: 63) sequence in the EmGFP reporter gene and were then transfected into wild type EmGFP cells via electroporation, followed by limiting dilution to isolate clonal cell lines. A stable disrupted EmGFP cell line with deletion of 5'-CTTCAC-3' was selected for homologous recombination assay using a 400 bp wild type PCR fragment amplified using a forward primer 5'-atggtgagcaagggcgaggagctg-3' (SEQ ID NO: 61) and a reverse primer 5'-GTCCTCCTTGAAGTCGATGCCC-3' (Table 2s) (SEQ ID NO: 62). The restoration of EmGFP function was determined by flow cytometric analysis with an ATTUNE® NxT Acoustic Focusing Cytometer (Thermo Fisher Scientific).

TABLE 2s

EmGFP sequence.

atggtgagcaagggcgaggagctgttcaccggggtggtgcccatcctggt
cgagctggacggcgacgtaaacggccacaagttcagcgtgtccggcgagg
gcgagggcgatgccacctacggcaagctgaccctgaagttcatctgcacc
accggcaagctgcccgtgccctggcccacccgtgaccaccttcaccta
cggcgtgcagtgcttcgcccgctaccccgaccacatgaagcagcacgact
tcttcaagtccgccatgcccgaaggctacgtccaggagcgcaccatcttc
ttcaaggacgacggcaactacaagacccgcgcgaggtgaagttcgaggg
cgacaccctggtgaaccgcatcgagctgaagggcatcgacttcaaggagg
acggcaacatcctggggcacaagctggagtacaactacaacagccacaag
gtctatatcaccgccgacaagcagaagaacggcatcaaggtgaacttcaa
gacccgccacaacatcgaggacggcagcgtgcagctcgccgaccactacc
agcagaacacccccatcggcgacggccccgtgctgctgcccgacaaccac
tacctgagcacccagtccgccctgagcaaagaccccaacgagaagcgcga
tcacatggtcctgctggagttcgtgaccgccgccgggatcactctcggca
        tggacgagctgtacaagtaa (SEQ ID NO: 64)

Note: oligonucleotide "cttcac" (strikethrough type) is deleted in mutant cell line.

Results

Figure 2:
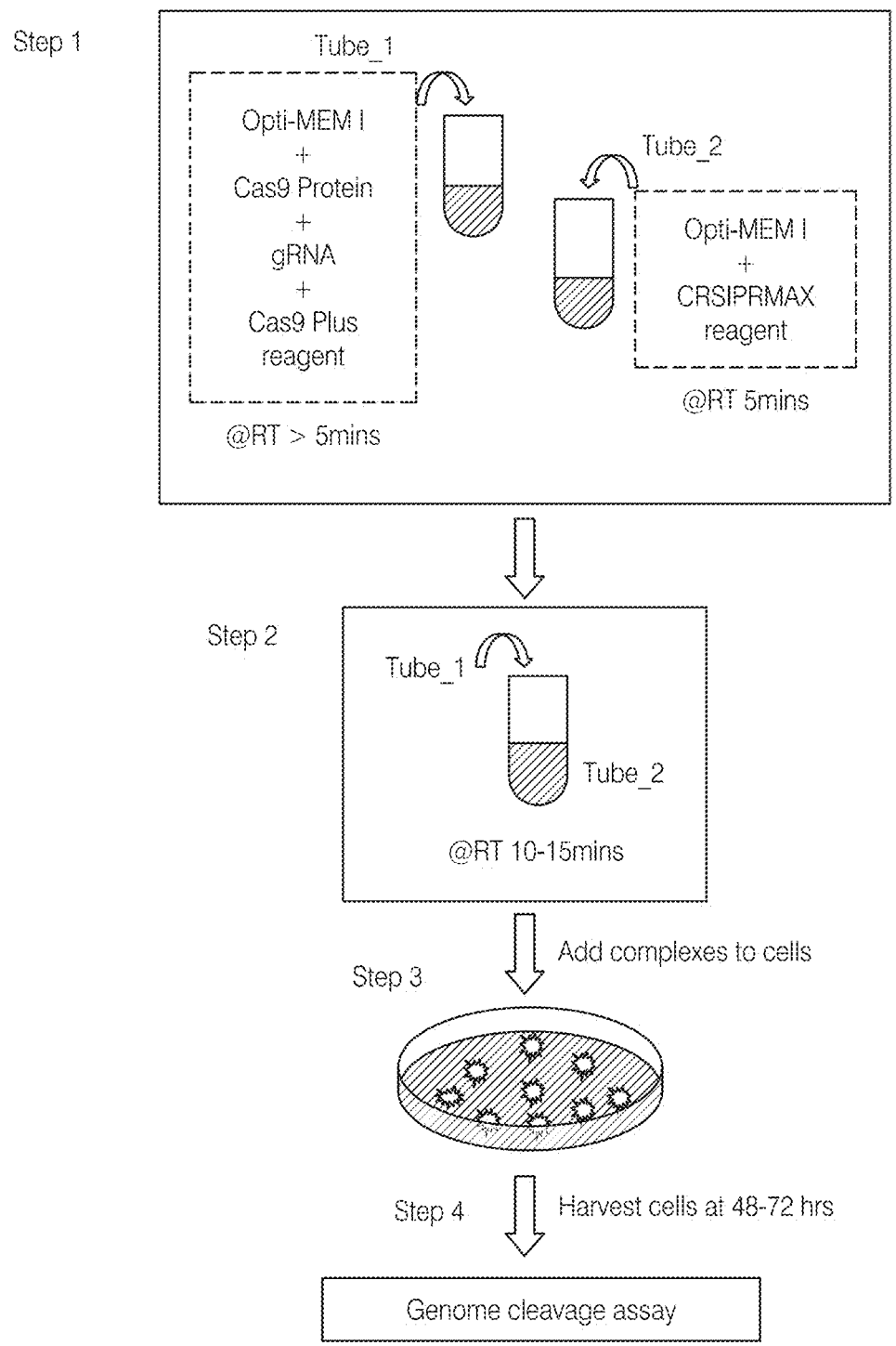
FIG. 2. Schematic depicting general protocol for cell transfection using LIPOFECTAMINE® CRISPRMAX™.
Figure 3A:
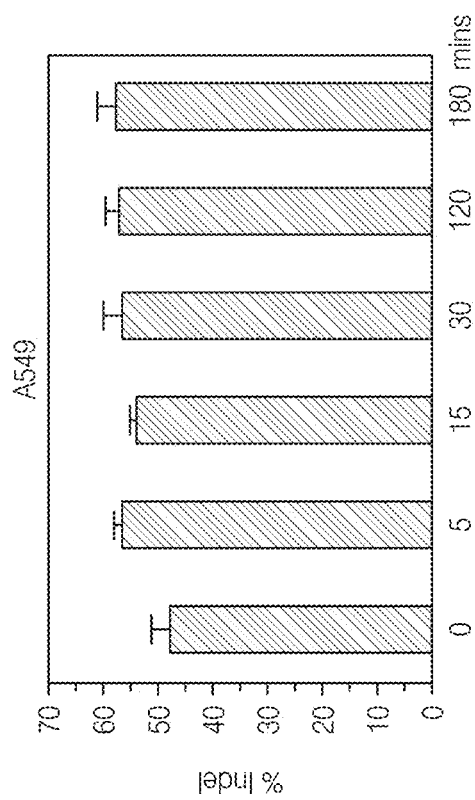
FIGS. 3A-3I. Stabilities of Cas9 RNP complexes and Cas9 RNP/LIPOFECTAMINE® CRISPRMAX™ complexes. A master mix of Cas9 RNP complexes and LIPOFECTAMINE® CRISPRMAX™ were prepared in OPTI-MEM® medium. The incubation times of Cas9 RNP, LIPOFECTAMINE® CRISPRMAX™, and Cas9 RNP/LIPOFECTAMINE® CRISPRMAX™ complexes were dependent variables. At indicated time point, aliquots of Cas9 RNP complexes in OPTI-MEM® were added to aliquots of LIPOFECTAMINE® CRISPRMAX™ and incubated for indicated time prior to addition to A549, HEK293, and Hela cells, respectively. Upon 48 hours post transfection, the genome cleavage efficiencies were determined.
Figure 3B:
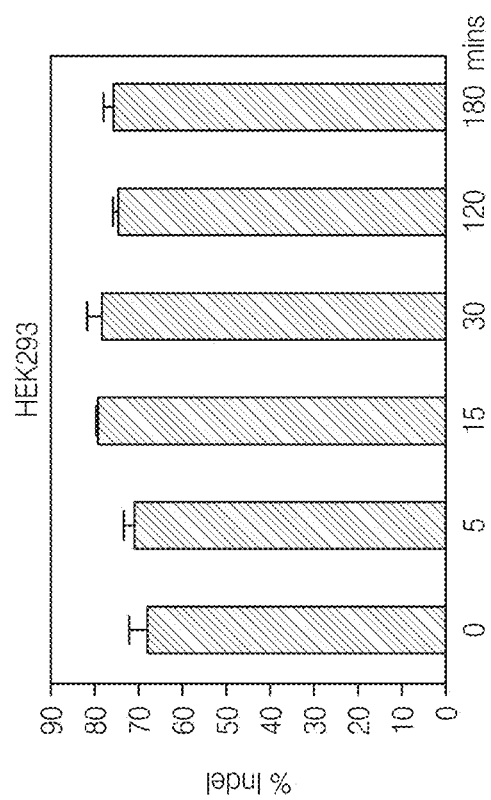
Figure 3C:
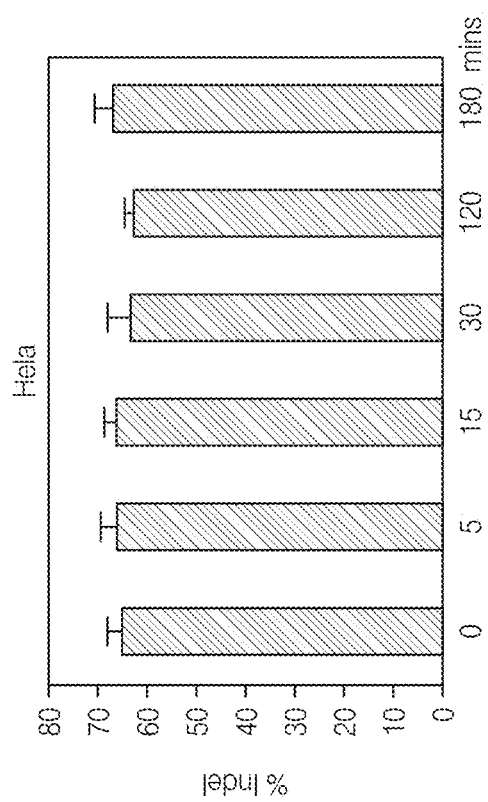
Figure 3D:
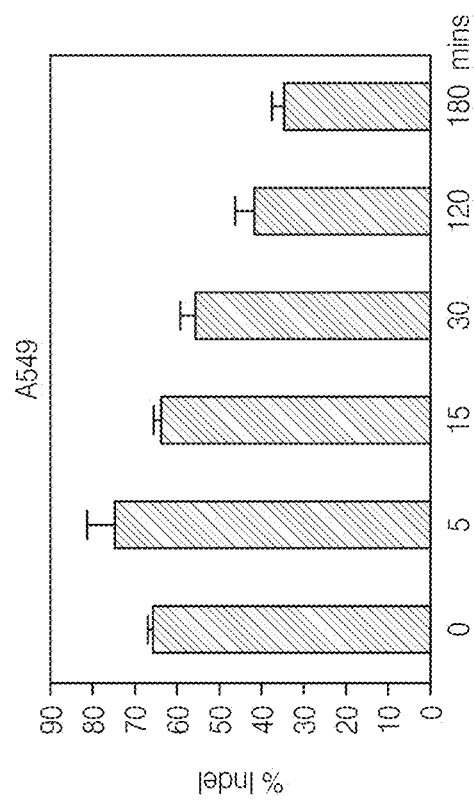
Figure 3E:
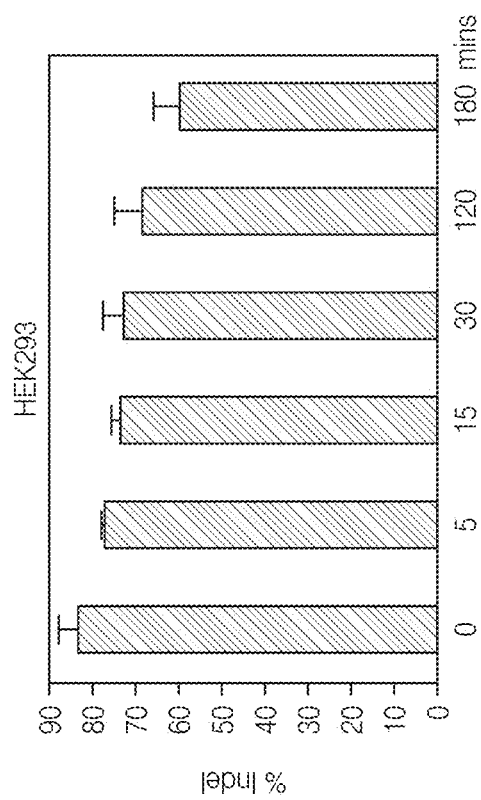
Figure 3F:
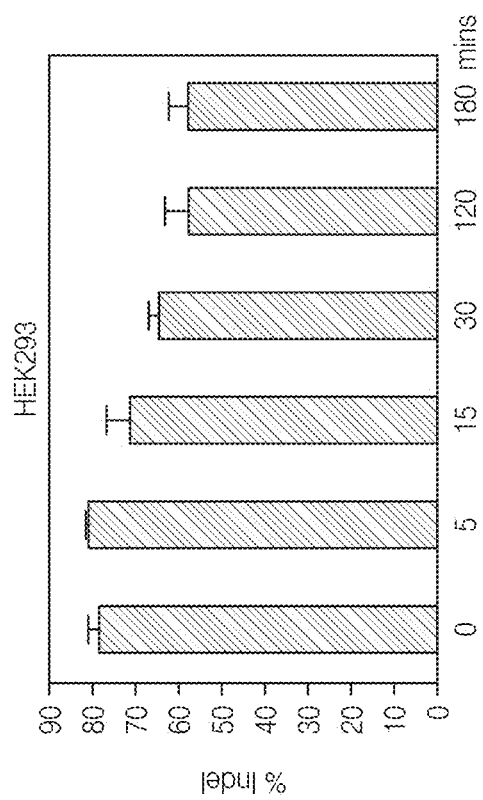
Figure 3G:
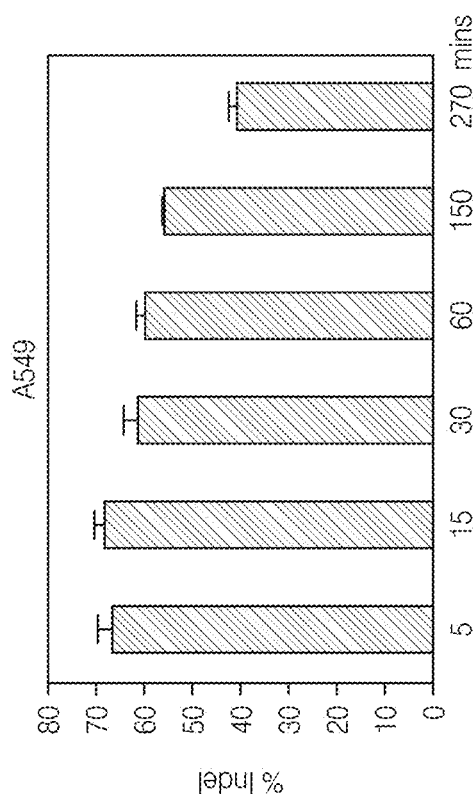
Figure 3H:
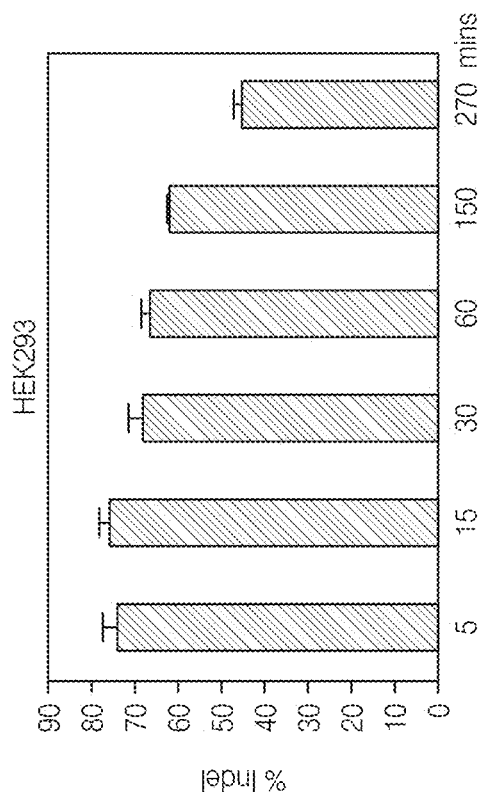
Figure 3I:
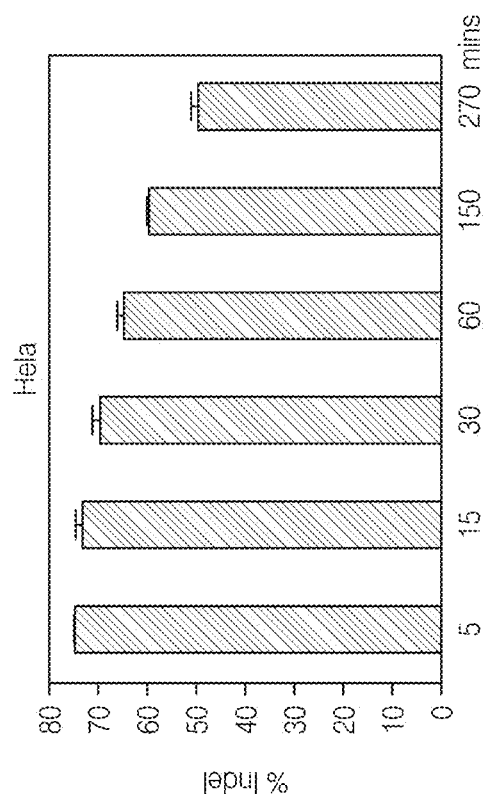

In order to identify the best transfection reagents for delivery of Cas9 RNP, we used a systematic Design of Experiment (DOE) approach to screen more than 60 transfection reagents, including LIPOFECTAMINE® 3000, LIPOFECTAMINE® RNAiMAX™ and LIPOFECTAMINE® MESSENGERMAX™-like reagents. For initial screening, three easy-to-transfect cell lines (HEK293, HeLa, and U2OS) and three hard-to-transfect cell lines (HepG2, A549, and MCF-7) were selected with a fixed amount of Cas9 RNP and four different doses of transfection reagents. Genome cleavage assays were carried out at 48 hours post transfection. Among all the formulations, only a few worked equally well or better than the current transfection reagents on the market with one formulation (LIPOFECTAMINE® CRISPRMAX™) stood out. Selected examples were shown in FIGS. 1A-1D. Upon identification of LIPOFECTAMINE® CRISPRMAX™, we examined the times for complexation of Cas9 protein with gRNA (Cas9 RNP) and Cas9 RNP with LIPOFECTAMINE® CRISPRMAX™, and also determined the orders of addition and mixing of each component. The final protocol was described in FIG. 2. The Cas9 protein, gRNA, and Cas9 PLUS™ reagent were added in orders to Tube_1 containing OPTI-MEM® medium. Briefly mixing by vortexing was conducted between each addition. As shown in FIG. 3A-3C, the Cas9 RNP complexes remained stable at room temperature for up to 3 hours based on the genome cleavage assay. Meanwhile, the LIPOFECTAMINE® CRISPRMAX™ was diluted in OPTI-MEM® medium in Tube_2. The diluted LIPOFECTAMINE® CRISPRMAX™ was only stable at room temperature for approximately 15 minutes as a longer incubation time decreased the cleavage efficiency (FIG. 3D-3F). In step 2 of FIG. 2, the Cas9 RNP complexes in Tube_1 were added to Tube_2 containing LIPOFECTAMINE® CRISPRMAX™. The reverse addition of Tube_2 to Tube_1 was found to decrease the genome editing efficiency in certain cell lines (data not shown). The Cas9 RNP and LIPOFECTAMINE® CRISPRMAX™ complexes were then incubated at room temperature for 10 to 15 minutes prior to addition to cells. A longer incubation time decreased the cleavage efficiency (FIG. 3G-3I). Upon cell transfection with Cas9 RNP and LIPOFECTAMINE® CRISPRMAX™ complexes, genome cleavage assays were performed at 48-72 hours post transfection.

Figure 4A:
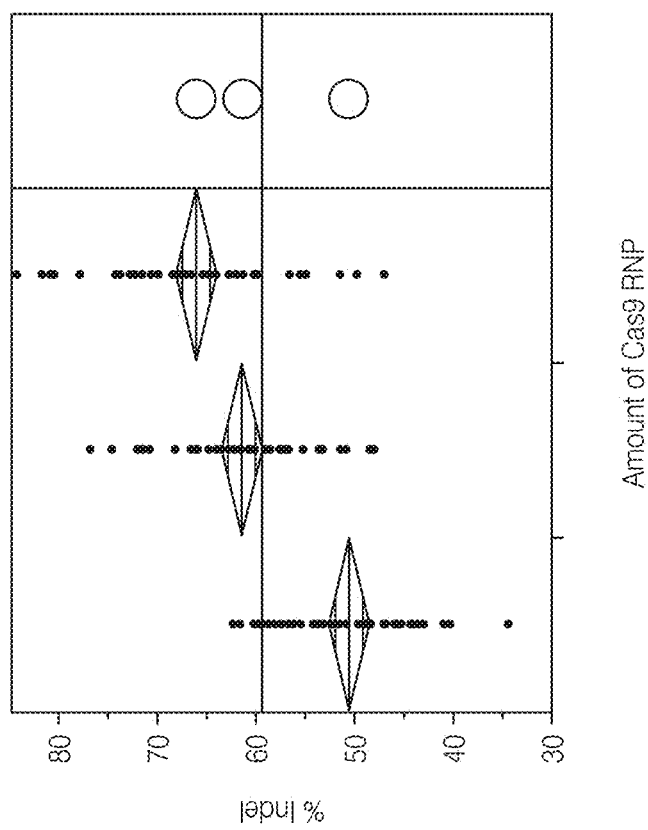
FIGS. 4A-4C. Factors regulating transfection efficiencies. Delivery of Cas9 RNP via LIPOFECTAMINE® CRISPRMAX™. A549, HEK293, HepG2, Hela, MCF-7 and U2OS were seeded on 96-well plates at two cell densities and then transfected with either 40 ng Cas9 protein and 8.5 ng gRNA (1×), 80 ng Cas9 protein and 17 ng gRNA (2×) or 120 ng Cas9 protein and 25.5 ng gRNA (3×) using either 0.2 or 0.4 µl of LIPOFECTAMINE® CRISPRMAX™. The editing efficiency was determined at 48 hours post transfection. The indel percentage was determined using an Alpha Imager and the resulting data was processed using JMP11 software. ANOVA (Analysis of variance) analysis of % Indel by dose of Cas9 RNP (FIG. 4A), cell density (FIG. 4B), and amount of transfection reagent (FIG. 4C) were carried out across six different cell lines.
Figure 4B:
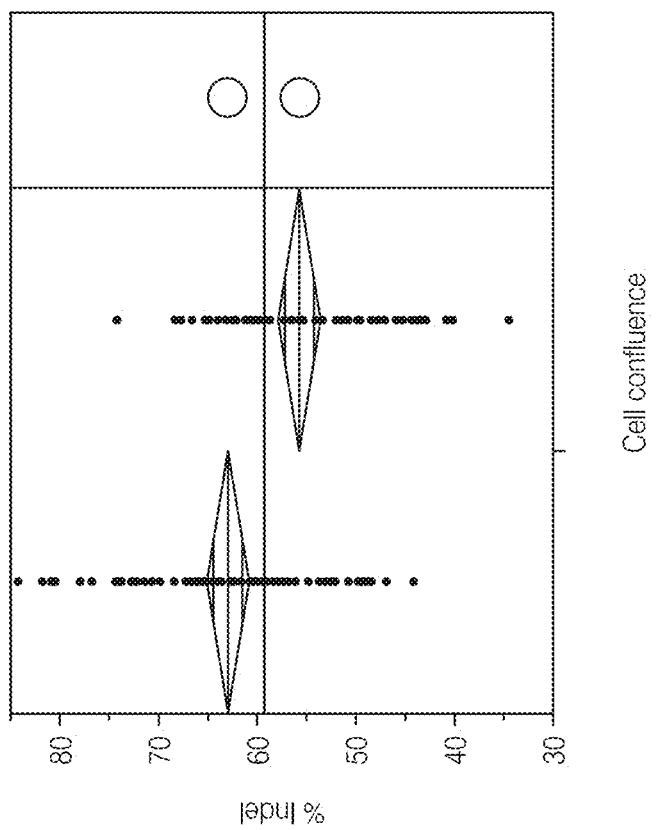
Figure 4C:
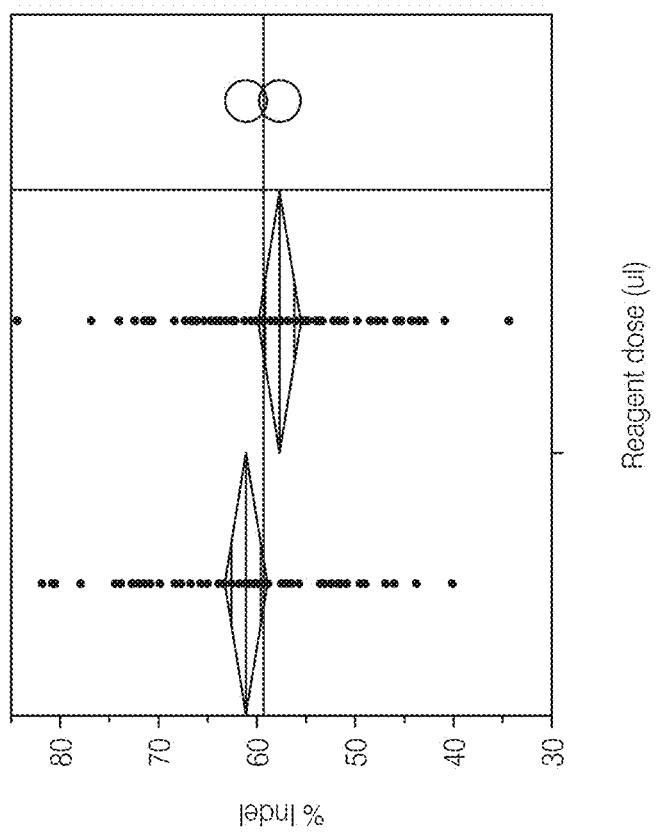

Next, we examined the key factors that governed the transfection efficiency by varying the dose of transfection reagent, the amount of Cas9 RNP, and cell density. Six commonly used cell lines were transfected with increasing amount of Cas9 RNPs, followed by genome cleavage assay. Analysis of Variance (ANOVA) indicated that the efficiency of indel production in transfected cells increased with an increase of Cas9 RNP complexes (FIG. 4A). To transfect cells in a 96-well plate, the optimal amounts of Cas9 protein and gRNA were approximately 120 ng and 28 ng respectively with the molar ratio of 1:1.2. Cell seeding density plays an important role in regulating the transfection efficiency. As depicted in FIG. 4B, the average genome modification efficiency across six different cell lines was significantly higher at 60% cell confluence than at 80% cell confluence on the day of transfection. Moreover, the efficiency is slightly higher at lower lipid dose than at higher lipid dose, although the difference is not significant (FIG. 4C). Other factors, such as cell passage and dissociation, also contributed to daily variation in cell transfection and indel efficiency.

Figure 5A:
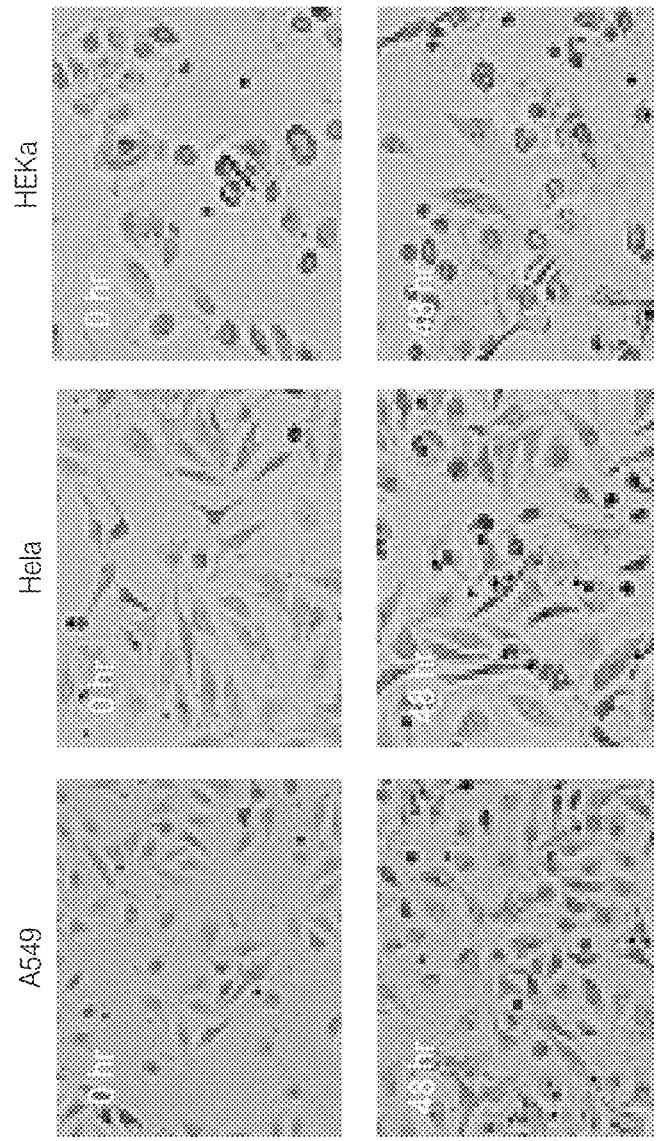
FIGS. 5A-5C. Cell toxicity using LIPOFECTAMINE® CRISPRMAX™.
Figure 5B:
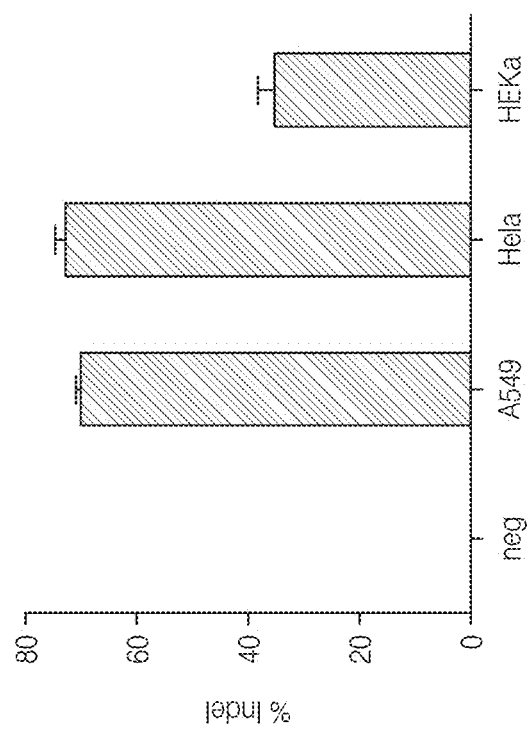
Figure 5C:
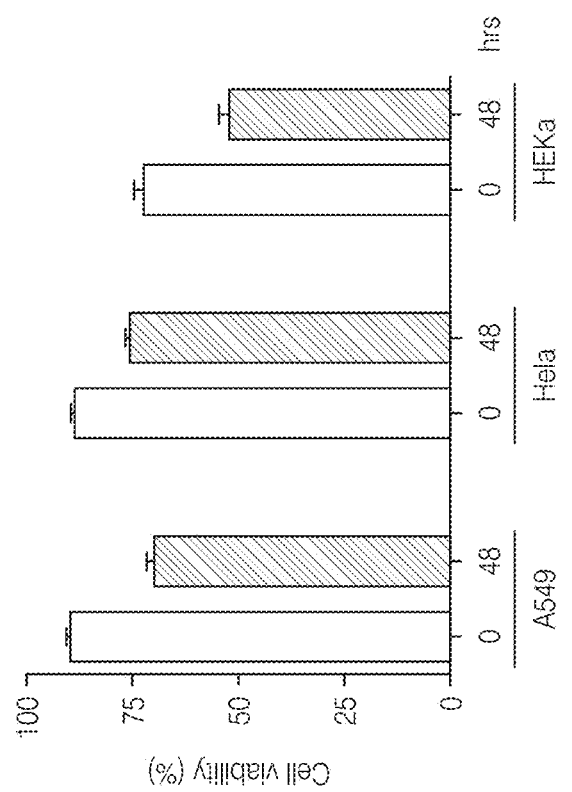

We then scaled up to 24 wells to test a set of 23 cell lines, including a variety of adherent and suspension cells from different species. The morphologies of adherent cells were recorded prior to transfection and at 48 hours post transfection. Most of the cells looked healthy under the microscopes with examples shown in FIG. 5A, very little floating dead cells were observed upon 48 hours post transfection for A549, Hela and epidermal keratinocytes (HEKa). Meanwhile, we observed good genome cleavage efficiencies in these cell lines (FIG. 5B). Cell viability assay with trypan blue indicated that the viable cells only decreased moderately after transfection compared to control cells, suggesting that the cell toxicity induced by CRISPRmax was relatively low (FIG. 5C). The low cell toxicity of CRISPRmax prompted us to transfect cells at much lower cell density so as to increase the transfection efficiency (Table I and Table 3s). For example, N2A, mouse ESC and iPSC were grown to 35%, 25% and 30% confluence at the time of transfection (Table 3s) and achieved 70%, 75% and 55% genome editing efficiencies at mouse Rosa26 and human HPRT1 loci, respectively (Table 1). The improved efficiencies were probably due to the high accessibility of transfection reagents at low cell density. However, the optimal cell density was highly dependent on cell type and needed to be determined experimentally.

TABLE 1

Genome editing efficiency in a variety of celllines.

| | Cell line | Source | LIPOFECTAMINE® CRISPRMAX™ (% Indel) | NEON™ Electroporation % Indel |
|---|---|---|---|---|
| 1 | mESC | Mouse embryonic stem cell | 75 ± 3 | 74 ± 4 |
| 2 | N2A | Mouse liver carcinoma | 70 ± 5 | 81 ± 2 |
| 3 | 3T3 | Mouse embryonic fibroblast | 57 ± 4 | 50 ± 2 |
| 4 | CHO | Hamster ovary | 57 ± 1 | — |
| 5 | COS-7 | Monkey kidney | 44 ± 3 | — |
| 6 | A549 | Human lung carcinoma | 48 ± 3 | 66 ± 3 |
| 7 | 293FT | Human kidney | 85 ± 5 | 88 ± 3 |
| 8 | HEK293 | Human kidney | 75 ± 5 | — |
| 9 | HCT116 | Human colon carcinoma | 85 ± 5 | — |
| 10 | HEKa | Human primary epidermal keratinocytes | 14 ± 2 | 32 ± 2 |
| 11 | HeLa | Human cervical cancer | 50 ± 7 | — |
| 12 | HepG2 | Human liver cancer | 30 ± 3 | 52 ± 3 |
| 13 | HUVEC | Human umbilical vein endothelium | 9 ± 3 | 26 ± 2 |
| 14 | iPSC | Human episomal induced pluripotent stem cell | 55 ± 3 | 85 ± 2 |
| 15 | MCF-7 | Human mammary gland | 8 ± 4 | 22 ± 5 |
| 16 | MDA-MB-231 | Human breast cancer | 39 ± 5 | — |
| 17 | U2OS | Human osteosarcoma | 55 ± 4 | 70 ± 3 |
| 18 | Jurkat | Human T cell leukemia | 19 ± 3 | 94 ± 2 |
| 19 | K562 | Human lymphoblastoid | 20 ± 2 | 91 ± 1 |
| 20 | THP-1 | Human monocytes | 12 ± 3 | 31 ± 3 |
| 21 | SC-1 | Human B lymphoblasts | 0 | 44 ± 2 |
| 22 | Raji | Human B lymphocyte | 0 | 50 ± 5 |
| 23 | NK-92 | Human peripheral blood | 0 | 31 ± 5 |

Mouse Rosa26, human HPRT1, monkey Nr0b1, and hamster COSMC loci were selected for genome editing. The average and standard deviation from NEON™ electroporation were calculated based on the top three protocols. Detailed electroporation protocol was described in Table 4s. (—) not tested.

TABLE 3s

Genome editing efficiency in a variety of cell lines (24-well Format)

| | Cell line | Cell Seeding Numbers/well (×10^3) | Confluence prior to transfection (%) | Cas9/ gRNA (ng/ng) | Cas9 PLUS ™ Reagent (μl) | LIPOFECTAMINE ® CRISPRMAX ™ (μl) | LIPOFECTAMINE ® CRISPRMAX ™ (% Indel) |
|---|---|---|---|---|---|---|---|
| 1 | mouse ESC | 100 | 25 | 500/125 | 1 | 2 | 75 ± 3 |
| 2 | N2A | 42 | 35 | 500/125 | 1 | 1.5 | 70 ± 5 |
| 3 | 3T3 | 45 | 43 | 500/125 | 1 | 1.5 | 57 ± 4 |
| 4 | CHO | 60 | 30 | 500/125 | 1 | 1.5 | 57 ± 1 |
| 5 | COS-7 | 90 | 75 | 500/125 | 1 | 1.5 | 44 ± 3 |
| 6 | A549 | 60 | 65 | 500/125 | 1 | 1.5 | 48 ± 3 |
| 7 | 293FT | 90 | 50 | 500/125 | 1 | 2 | 85 ± 5 |
| 8 | HEK293 | 120 | 45 | 500/125 | 1 | 1.5 | 75 ± 5 |
| 9 | HCT116 | 90 | 49 | 500/125 | 1 | 1.5 | 85 ± 5 |
| 10 | HEKa | 90 | 60 | 500/125 | 1 | 1.5 | 14 ± 2 |
| 11 | HeLa | 60 | 55 | 500/125 | 1 | 1.5 | 50 ± 7 |
| 12 | HepG2 | 90 | 40 | 500/125 | 1 | 1.5 | 30 ± 3 |
| 13 | HUVEC | 90 | 70 | 500/125 | 1 | 1.5 | 9 ± 3 |
| 14 | iPSC | 40 | 30 | 1000/250 | 6 | 1.5 | 55 ± 3 |
| 15 | MCF-7 | 144 | 55 | 500/125 | 1 | 1.5 | 8 ± 4 |
| 16 | MDA-MB-231 | 90 | 45 | 500/125 | 1 | 1.5 | 39 ± 5 |
| 17 | U2OS | 90 | 80 | 500/125 | 1 | 1.5 | 55 ± 4 |
| 18 | Jurkat | 100 | n/a | 500/125 | 1 | 1.5 | 19 ± 3 |
| 19 | K562 | 100 | n/a | 500/125 | 1 | 1.5 | 20 ± 2 |
| 20 | THP-1 | 100 | n/a | 500/125 | 1 | 1.5 | 12 ± 3 |
| 21 | SC-1 | 100 | n/a | 500/125 | 1 | 1.5 | 0 |
| 22 | Raji | 100 | n/a | 500/125 | 1 | 1.5 | 0 |
| 23 | NK-92 | 100 | n/a | 500/125 | 1 | 1.5 | 0 |

| | | NEON ™ Electroporation (10 ul tips) | | |
|---|---|---|---|---|
| | Protocol (Program #) | Cell Numbers (×10^3) | Cas9/ gRNA (ng/ng) | % Indel |
| 1 | 1600 v/10 ms/3pulses(#24) | 150 | 1000/250 | 74 ± 4 |
| 2 | 1400 v/30 ms/1pulse(#9) | 100 | 1000/250 | 81 ± 2 |
| 3 | 1600 v/10 ms/3pulses(#24) | 120 | 1000/250 | 50 ± 2 |
| 4 | — | — | — | — |
| 5 | — | — | — | — |
| 6 | 1200 v/20 ms/4pulses(*) | 120 | 1000/250 | 66 ± 3 |
| 7 | 1150 v/20 ms/2pulses(*) | 150 | 1000/250 | 88 ± 3 |
| 8 | — | — | — | — |
| 9 | — | — | — | — |
| 10 | 1400 v/20 ms/2pulses(#16) | 100 | 2000/500 | 32 ± 2 |
| 11 | — | — | — | — |
| 12 | 1300 v/30 ms/1pulse(#8) | 120 | 1000/250 | 52 ± 3 |
| 13 | 1600 v/10 ms/3pulses(#24) | 100 | 2000/500 | 26 ± 2 |
| 14 | 1200 v/20 ms/2pulses(#14) | 80 | 2000/500 | 85 ± 2 |
| 15 | 1150 v/30 ms/2pulses(#20) | 120 | 1000/250 | 22 ± 5 |
| 16 | — | — | — | — |
| 17 | 1400 v/15 ms/4pulses(*) | 150 | 1000/250 | 70 ± 3 |
| 18 | 1700 v/20 ms/1pulse(#5) | 200 | 1500/350 | 94 ± 2 |
| 19 | 1400 v/10 ms/3pulses(#22) | 200 | 1000/250 | 91 ± 1 |
| 20 | 1600 v/10 ms/3pulses(#24) | 200 | 1000/250 | 31 ± 3 |
| 21 | 950 v/30 ms/2pulses(#18) | 200 | 1000/250 | 44 ± 2 |
| 22 | 1600 v/10 ms/3pulses(#24) | 200 | 1000/250 | 50 ± 5 |
| 23 | 1400 v/10 ms/3pulses(#22) | 200 | 2000/500 | 31 ± 5 |

Mouse Rosa26, human HPRT1, monkey Nr0b1, and hamster COSMC loci were selected for genome editing.
The average and standard deviation from NEON ™ electroporation were calculated based on the top three protocols.
(—) not tested.
n/a: non-applicable.
(*)special program, not included in NEON ™ 24 conditions.

TABLE 4s

NEON ™ optimization protocols

| Protocol | 1 | 2 | 3 | 4 | 5 | 6 | 7 | 8 | 9 | 10 | 11 | 12 |
|---|---|---|---|---|---|---|---|---|---|---|---|---|
| Pulse Voltage (V) | 0 | 1400 | 1500 | 1600 | 1700 | 1100 | 1200 | 1300 | 1400 | 1000 | 1100 | 1200 |
| Pulse Width (ms) | 0 | 20 | 20 | 20 | 20 | 30 | 30 | 30 | 30 | 40 | 40 | 40 |
| # of Pulse | 0 | 1 | 1 | 1 | 1 | 1 | 1 | 1 | 1 | 1 | 1 | 1 |

TABLE 4s-continued

| NEON™ optimization protocols | | | | | | | | | | | | |
|---|---|---|---|---|---|---|---|---|---|---|---|---|
| Protocol | 13 | 14 | 15 | 16 | 17 | 18 | 19 | 20 | 21 | 22 | 23 | 24 |
| Pulse Voltage (V) | 1100 | 1200 | 1300 | 1400 | 850 | 950 | 1050 | 1150 | 1300 | 1400 | 1500 | 1600 |
| Pulse Width (ms) | 20 | 20 | 20 | 20 | 30 | 30 | 30 | 30 | 10 | 10 | 10 | 10 |
| # of Pulse | 2 | 2 | 2 | 2 | 2 | 2 | 2 | 2 | 3 | 3 | 3 | 3 |

Suspension cells, especially hematopoietic cells, are known to be difficult to transfect by conventional lipid reagents, including LIPOFECTAMINE® 3000 and LIPOFECTAMINE® CRISPRMAX™. For each hard-to-transfect cell line, we tested the delivery of Cas9 RNP using NEON™ 24 optimization protocols (Table 4s). For example, using electroporation we achieved 95%, 90% and 56% indel production efficiencies in Jurkat T cells, K562 and SC-1 cells respectively at the HPRT1 locus, whereas relatively low genome modification efficiencies were observed using LIPOFECTAMINE® CRISPRMAX™ in these suspension cell lines.

Figure 6B:
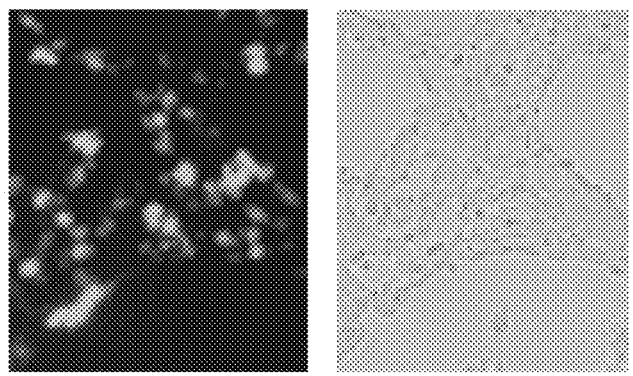
FIGS. 6A-6F. Co-delivery of Cas9 RNP and donor DNA. Plasmid DNA expressing EmGFP was co-transfected with Cas9 RNP into either HCT116 or HEK293 cells (FIGS. 6A,6B). Alternatively, a 400 bp PCR fragment was co-delivered with Cas9 RNP into a stable GripTite HEK293 (HEK293*) cell line with a disrupted EmGFP gene (Cas9 RNP/D) (FIGS. 6C,6D). Delivery of Cas9 RNP or Cas9 plus donor DNA (Cas9/D) served as controls. Upon 48 hrs post transfection, the cells were subjected to Flow Cytometric analysis and genomic modification assay. The experiments were performed in triplicate.
Figure 6A:
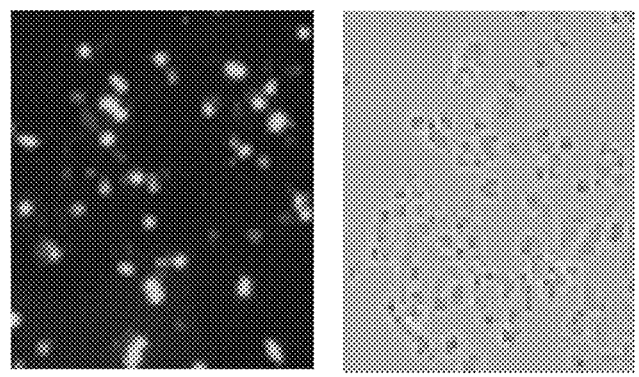
Figure 6D:
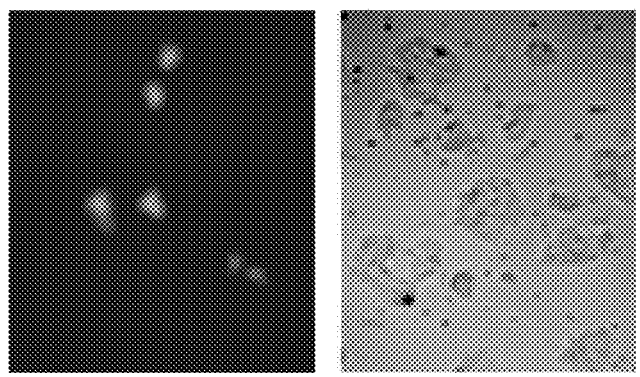
Figure 6C:
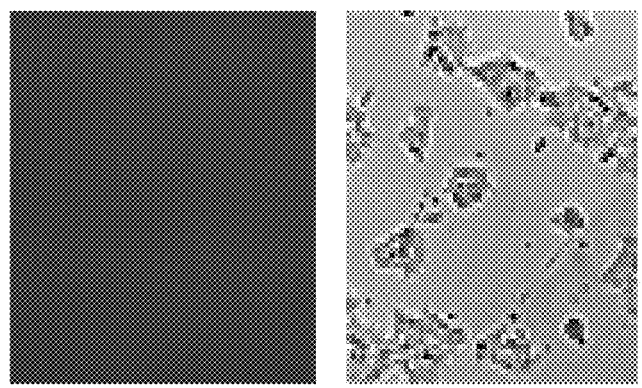
Figure 6E:
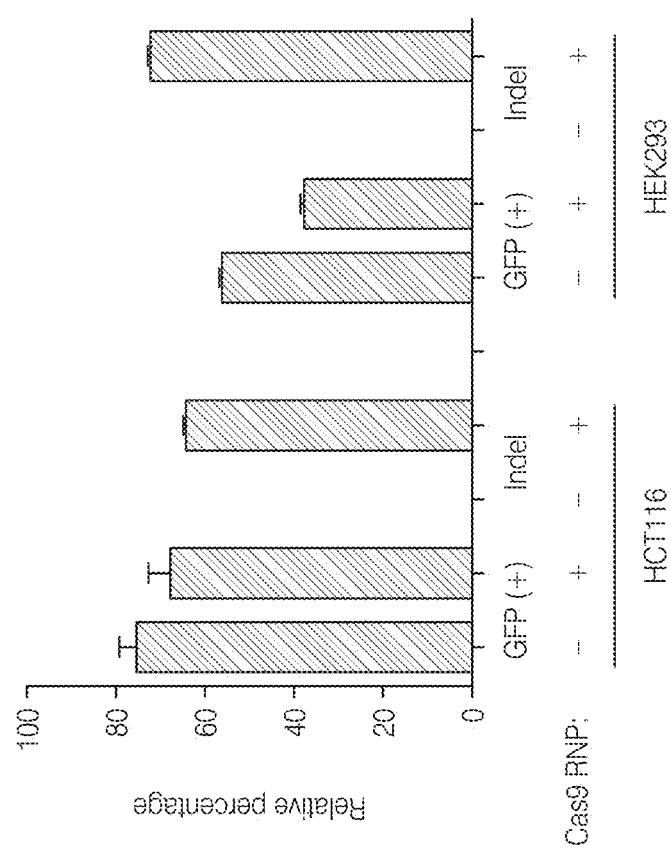
Figure 6F:
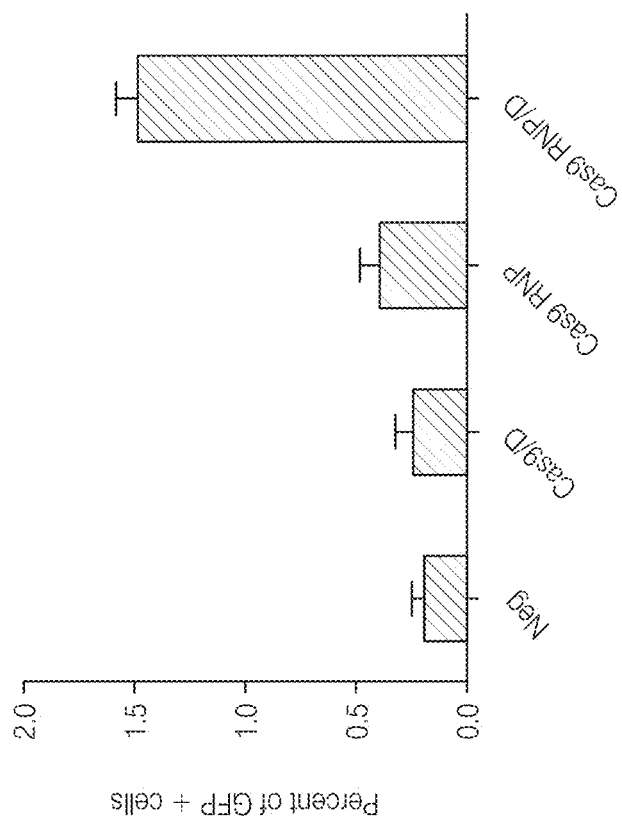

Precise gene modification, such as SNP (Single-Nucleotide Polymorphism) correction in cancer cells, is an important aspect in biomedical and clinical applications. For a proof of concept, we tested the co-delivery of plasmid DNA expressing EmGFP with Cas9 RNP into HCT116 and HEK293 cells using LIPOFECTAMINE® CRISPRMAX™. Based on flow cytometric analysis, the plasmid DNA was able to co-deliver into HCT116 and HEK293 cells with approximately 70% and 40% efficiencies respectively (FIGS. 6A-6B), which were slightly lower than the controls transfected with EmGFP plasmid alone. However, approximately 65% and 72% genome modification efficiencies were observed in HCT116 and HEK293 cells respectively transfected with both Cas9 RNP and plasmid DNA. To examine the precise replacement of gene segment in the genome, we co-delivered a 400 bp donor DNA fragment along with Cas9 RNP into a stable GRIPTITE™ HEK293 cell line harboring a disrupted EmGFP gene and approximately 1% of the cells restored the function of EmGFP (FIGS. 6C-6D). The low efficiency of homologous recombination remains the major obstacle and needs to be fully explored.

In summary, we demonstrated that LIPOFECTAMINE® CRISPRMAX™ was more robust than LIPOFECTAMINE® RNAiMAX™ in delivery of Cas9 protein and gRNA complexes into a variety of cell lines. Because of ease of use and low toxicity, LIPOFECTAMINE® CRISPRMAX™ will further facilitate high throughput drug screening and genome editing where electroporation is less applicable.

REFERENCES

Example 1

[1] Copolovici, D. M., Langel, K., Eriste, E., and Langel, Ü. (2014) Cell-Penetrating Peptides: Design, Synthesis, and Applications. ACS Nano, 8(3), 1972-1994; [2] Erazo-Oliveras, A., Najjar, K., Dayani, L., Wang, T. Y., Johnson, G. A., and Pellois, J. P. (2014) Protein delivery into live cells by incubation with an endosomolytic agent. Nat Methods. 11(8):861-867; [3] Jo, J., Hong, S., Choi, W. Y., and Lee, D. R. (2014) Cell-penetrating peptide (CPP)-conjugated proteins is an efficient tool for manipulation of human mesenchymal stromal cells. Sci Rep. 4:4378; [4] Kim, S., Kim, D., Cho, S. W., Kim, J., and Kim, J. S. (2014) Highly efficient RNA-guided genome editing in human cells via delivery of purified Cas9 ribonucleoproteins. Genom Res. 24, 1012-1019; [5] Zuris, J. A., Thompson, D. B., Shu, Y., Guilinger, J. P., Bessen, J. L., Hu, J. H., Maeder, M. L., Joung, J. K., Chen, Z. Y. and Liu, D. R. (2015) Cationic lipid-mediated delivery of proteins enables efficient protein-based genome editing in vitro and in vivo. Nat Biotechnol. 33:73-80; [6] Liang, X., Potter, J., Kumar, S., Zou, Y., Quintanilla, R., Sridharan, M., Jason Carte, J., Chen, W., Roark, N., Ranganathan, S., Ravinder, N., and Chesnut, J. D. (2015) Rapid and Highly Efficient Cell Engineering via Cas9 Protein Transfection. J. of Biotechnol. 208:44-53; [7] D'Astolfo, D. S., Pagliero, R. J., Pras, A., Karthaus, W. R., Clevers, H., Prasad, V., Lebbink, R. J., Rehmann, H., Geijsen, N. (2015) Efficient intracellular delivery of native proteins. Cell. 161 (3):674-690.

Example 2. Representative CRISPRMAX™ Transfection Protocol-iPSC (E8 Culture System, 24-Well Plate Format CRISPRMAX™ transfection kit: CRISPRMAX™ A and B.

Transfection Protocol

Day-0: the day before transfection. Seed the cells in GELTREX® coated 24-well plate at 30% confluent at the time of transfection.

Day-1 (Morning): the day of transfection. Don't change cell media at this point. Prepare Cas9-gRNA/lipid complex as in the table following.

| Culture vessel | Tube-1 | | Tube-2 | | | |
|---|---|---|---|---|---|---|
| | Vol. OPTI-MEM | CrisprMax-A | Vol. Opti-MEM | Cas9 Protein | gRNA | CrisprMax-B |
| 24-well | 25 ul | 2 ul | 25 ul | 500 ng | 125 ng | 2 ul |

Incubate Tube-1 at RT for 3-5 mins. Make complex by adding Tube-1 mixture to Tube-2 (the order of addition is important). Vortex mix. Incubate 15 min at RT After 15 minutes incubation, add 50 µl complex to cells.
Day-1 (Afternoon): Post-transfection 6 hrs, change cell medium by replacing 1 ml of fresh iPSC culture Medium
Day-2: Incubating the cells in 37C incubator.
Day-3: Post-transfection 48 hrs, harvest the cells by washing the cells once with 500 µl PBS and adding 100 µl lysis buffer prior to GCD (genomic cleavage detection) assay.

Example 3. CRISPR Technology-Cell Engineering

Figure 7:
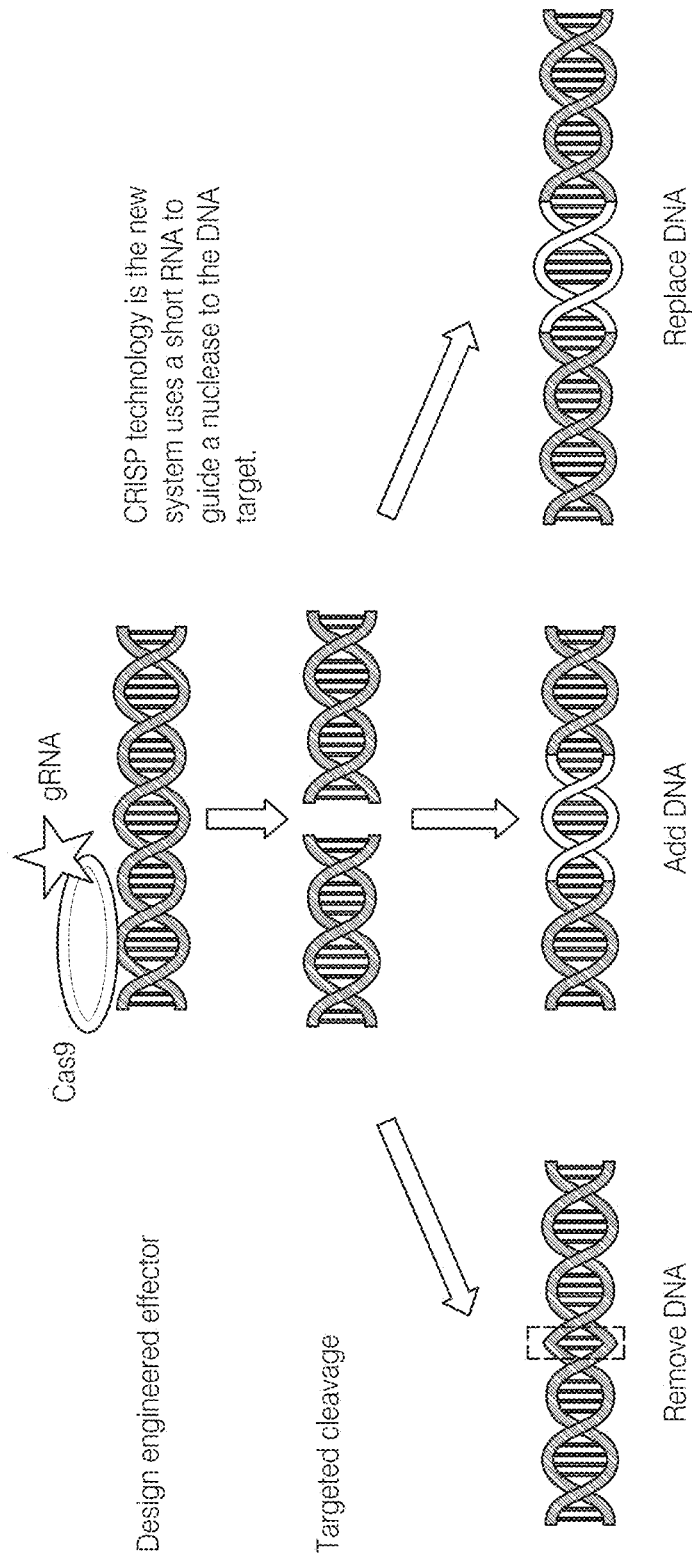
FIG. 7. Schematic depicting CRISPR technology in cell engineering.

FIG. 7 depicts a schematic representation of CRISPR technology directed toward cell engineering. CRISPR technology uses a short RNA fragment to guide a nuclease to the target DNA. After targeted cleavage, options available to the user include removal of DNA, replacement of DNA, and addition of DNA.

Example 4. CRISPR Cas9 Delivery Formats

Figure 8:
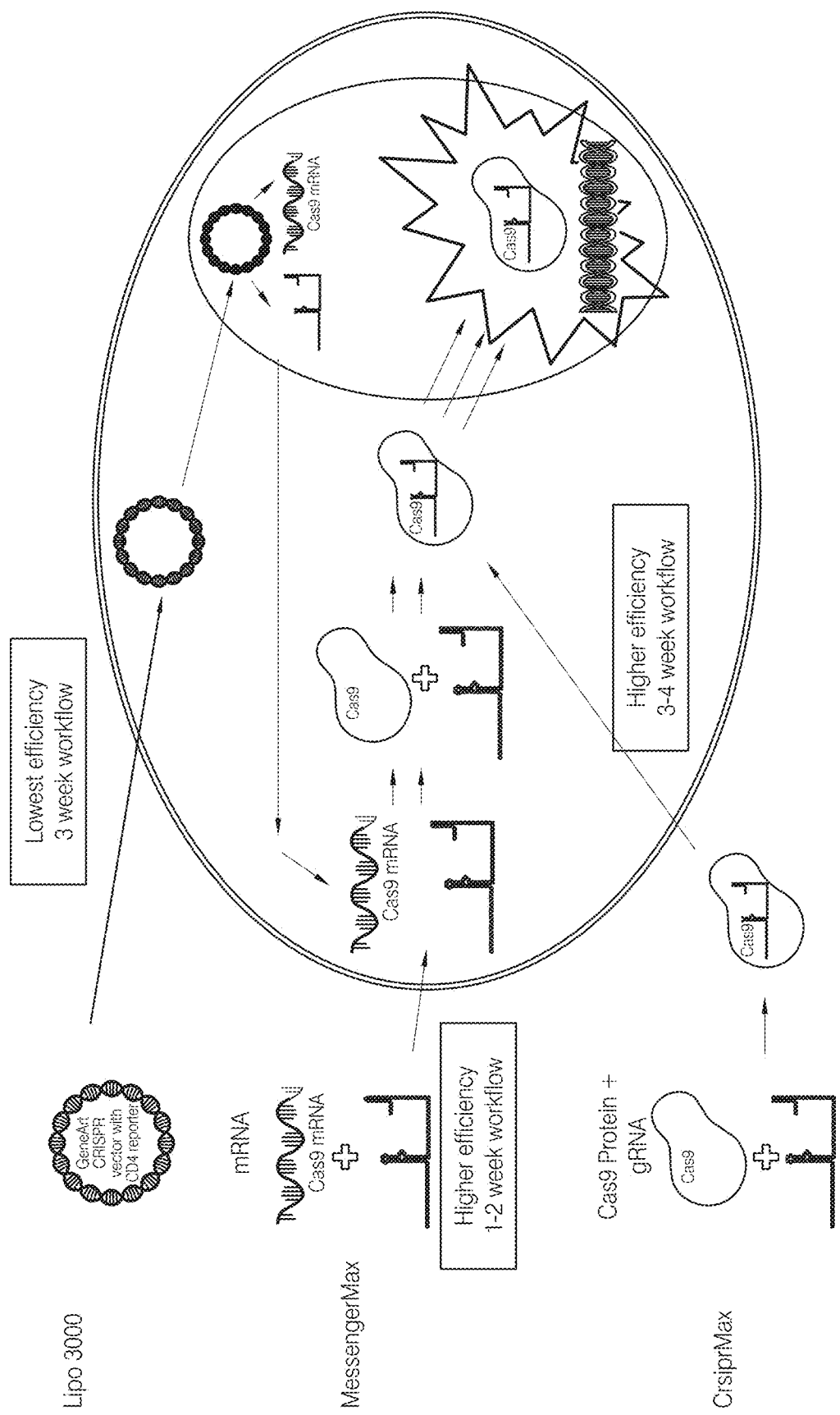
FIG. 8. Schematic depicting delivery formats available for Cas9.

FIG. 8 depicts a schematic representation of various Cas9 delivery format. It is observed that direct plasmid incorporation, using e.g., vector with reporter, has the lowest efficiency, typically resulting in about 3-week workflow. Employing MESSENGERMAX™ methodology can result in higher throughput efficiency, typically requiring 1-2 weeks workflow. Alternatively, CRISPRMAX™ can result in high efficiency, typical requiring 3-4 day workflow.

Example 5. Lipid Screening Experimental Design

Figure 9:
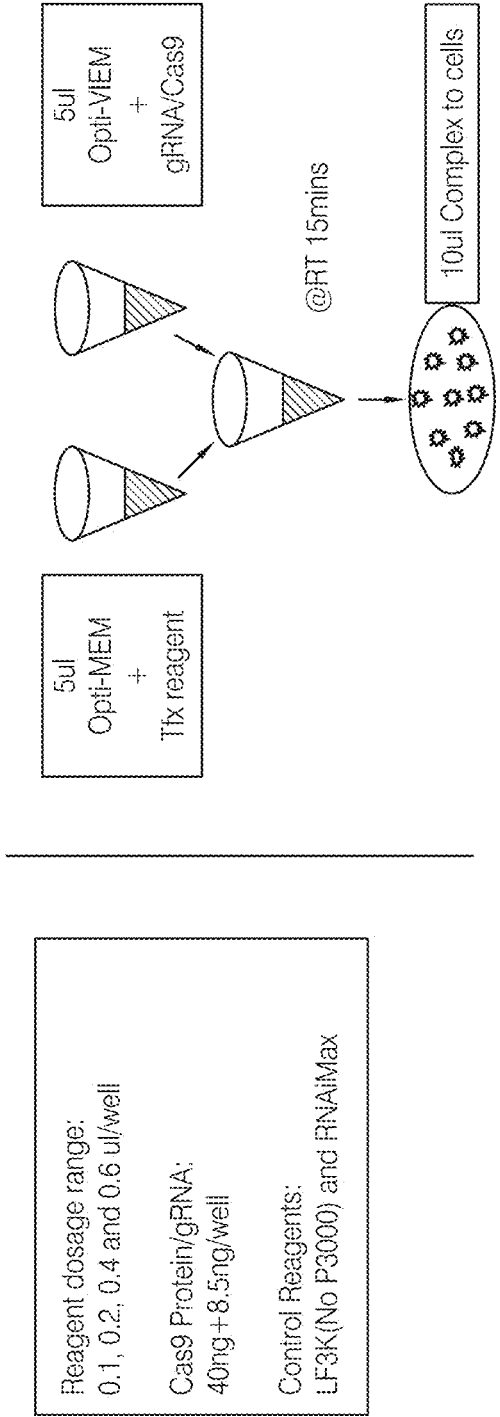
FIG. 9. Schematic depicting lipid screening experimental design.

FIG. 9 depicts a schematic representation of experimental design for lipid screening. A typical screening experiment can employ 96-well plates and a variety of common cell lines (e.g., HEK293, HeLa, HepG2, MCF-7,k A549 and U20). Reagent dosage range can be 0.1, 0.2, 0.4 and 0.6 µL/well. Cas9 prote8n/gRNA can be 40 ng+8.5 ng/well. Control reagents can be LF3K and RNAiMax. Transfection can be achieved as depicts in FIG. 9. GCD assay can be conducted 48-hr post-transfection.

Example 6. Lipid Library-DOE Formulation

Xa serial reagents can be based on LF3K reagent core compounds, resulting a variety of different reagent formulations.

Xb serial reagents are based on RNAiMAX reagent core compounds, resulting a variety of different reagent formulations.

N serial reagents are MESSENGERMAX™-like, resulting a variety of different reagent formulations.

Example 7. Lipid Screening-Hela, A549 Cells

Figure 10A:
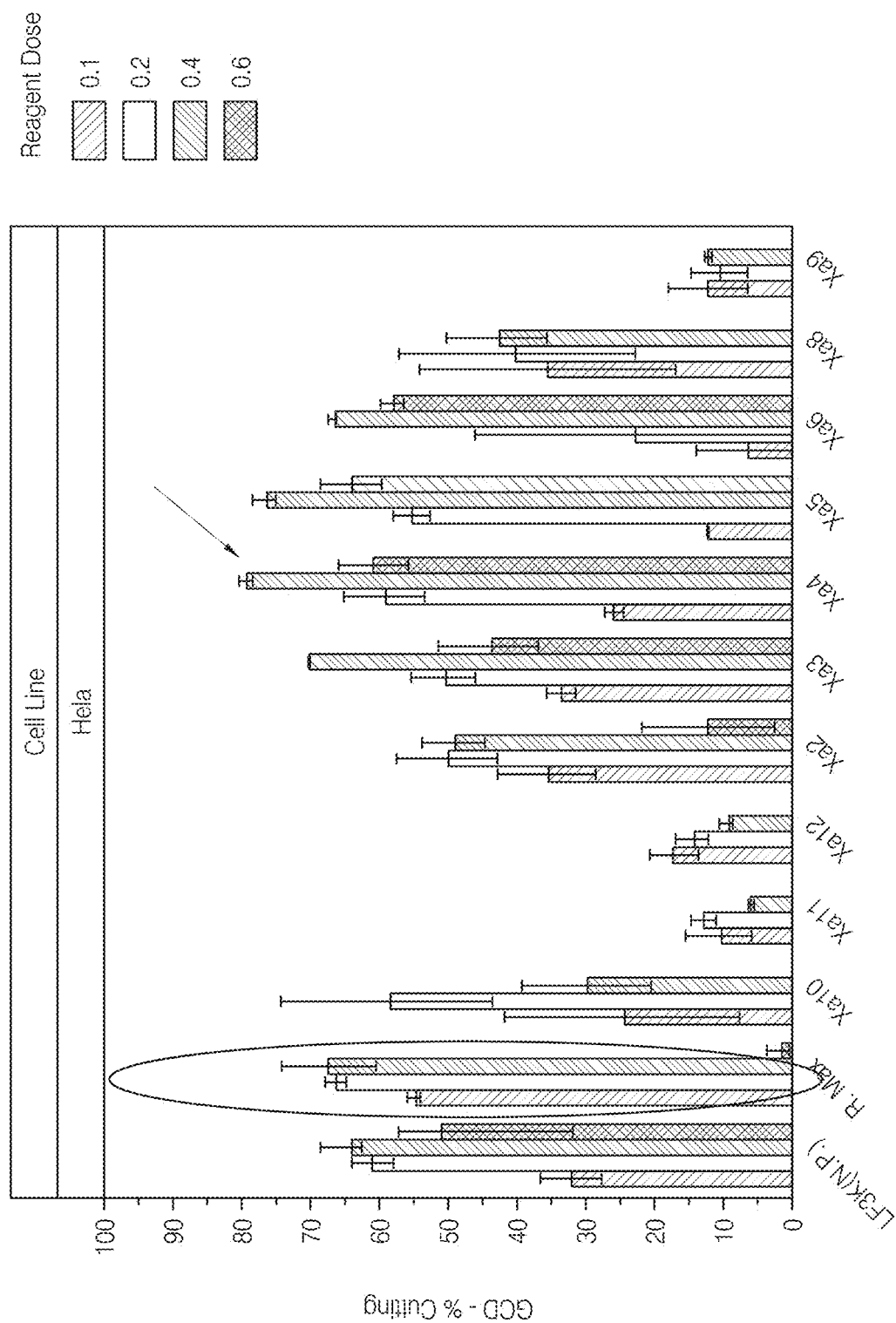
FIGS. 10A-10F. Histograms of results of lipid screening for Hela cells (upper row) and A549 cells (lower row) employing Xa serial, Xb serial and N serial. Within each histogram bin, reagent dose was (in order left to right) 0.1, 0.2, 0.4 and 0.6 uL/well.
Figure 10B:
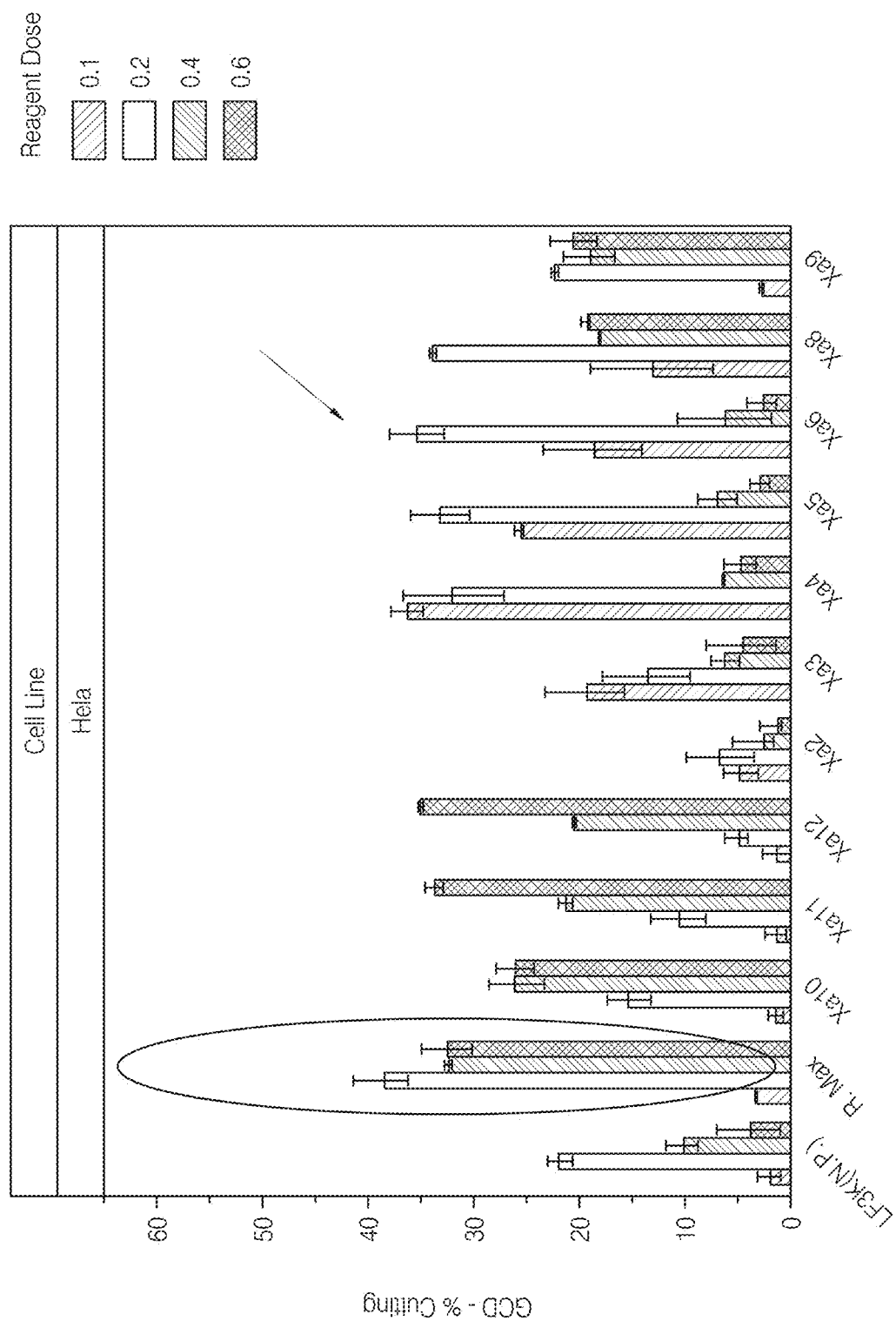
Figure 10C:
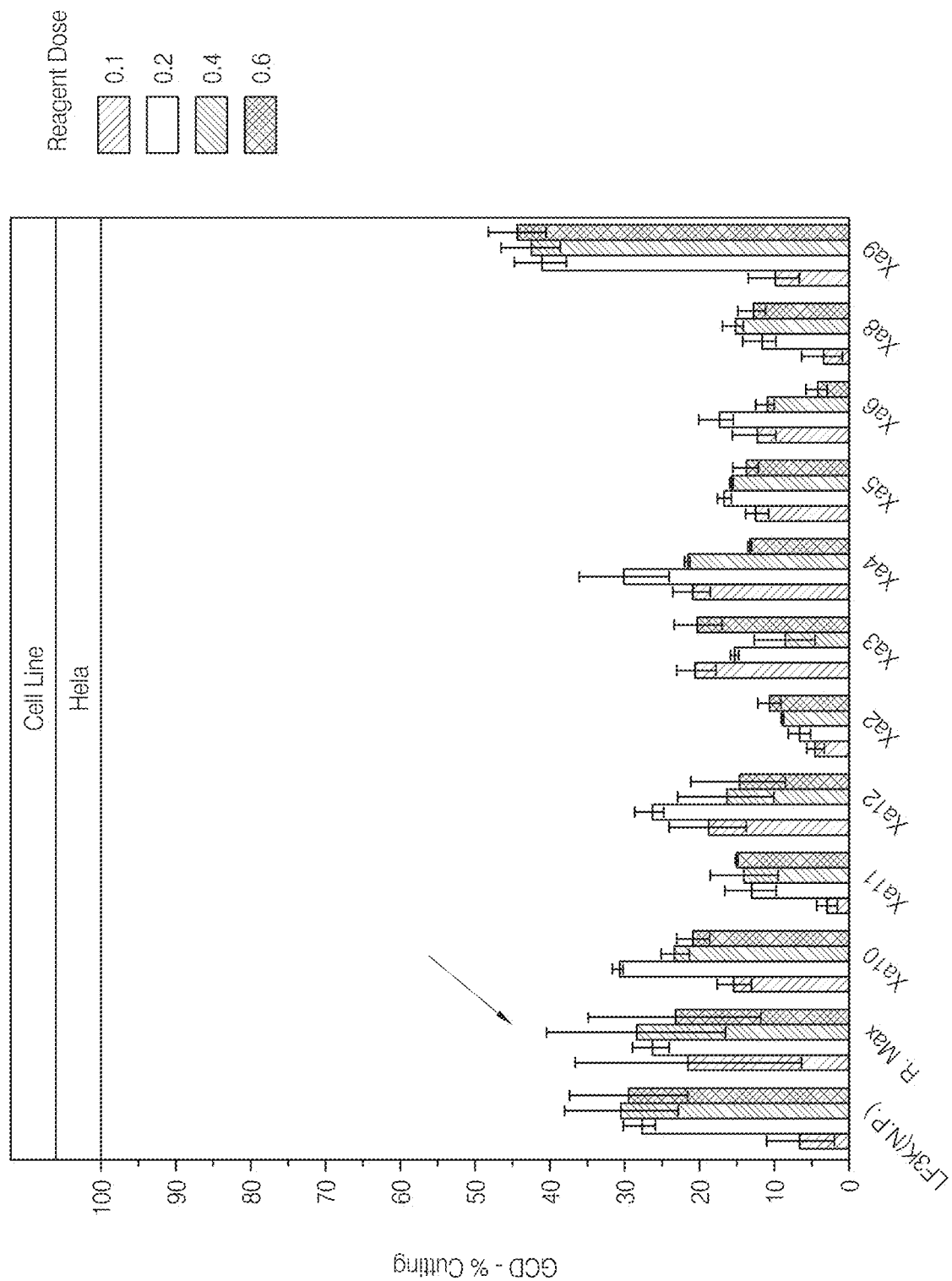
Figure 10D:
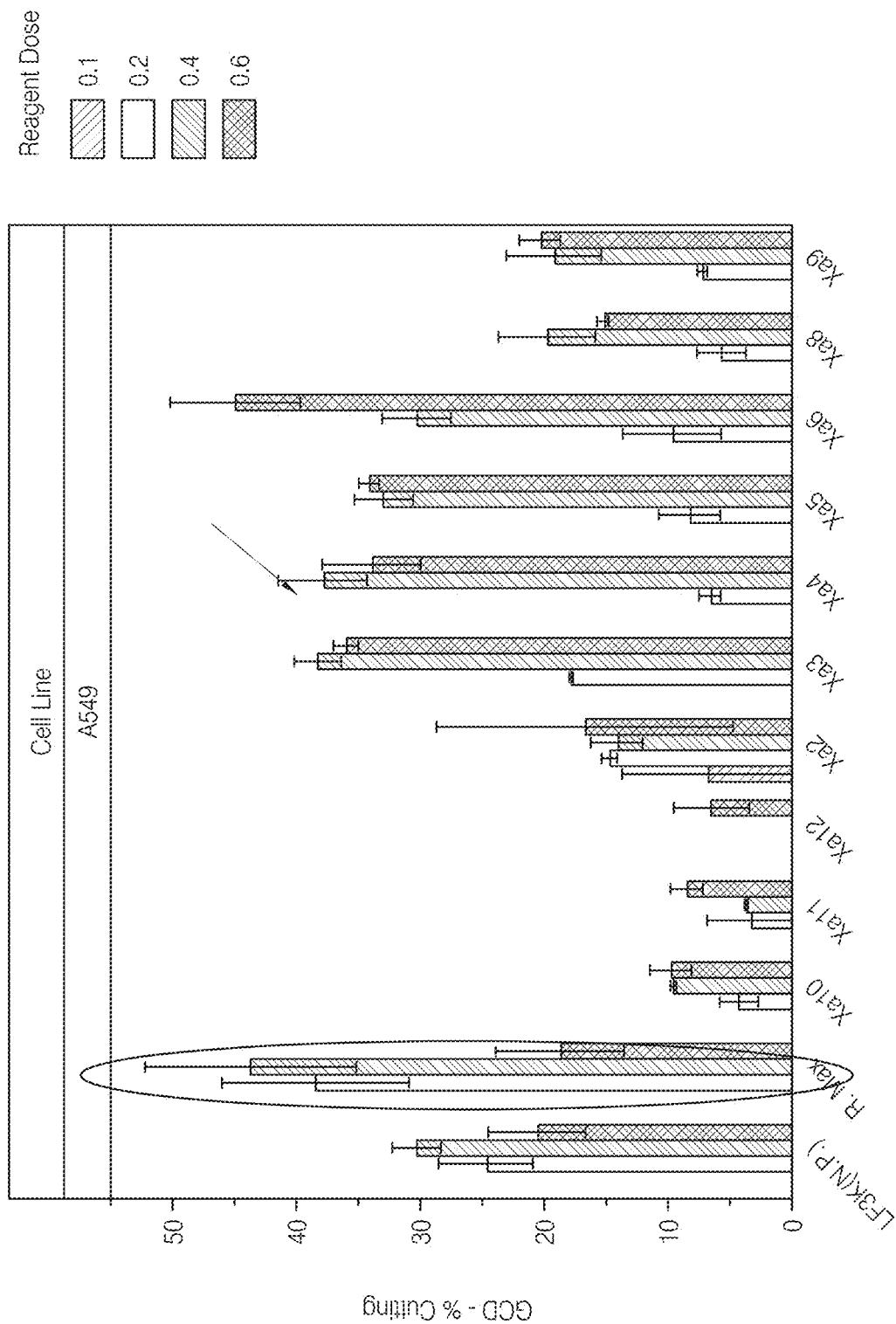
Figure 10E:
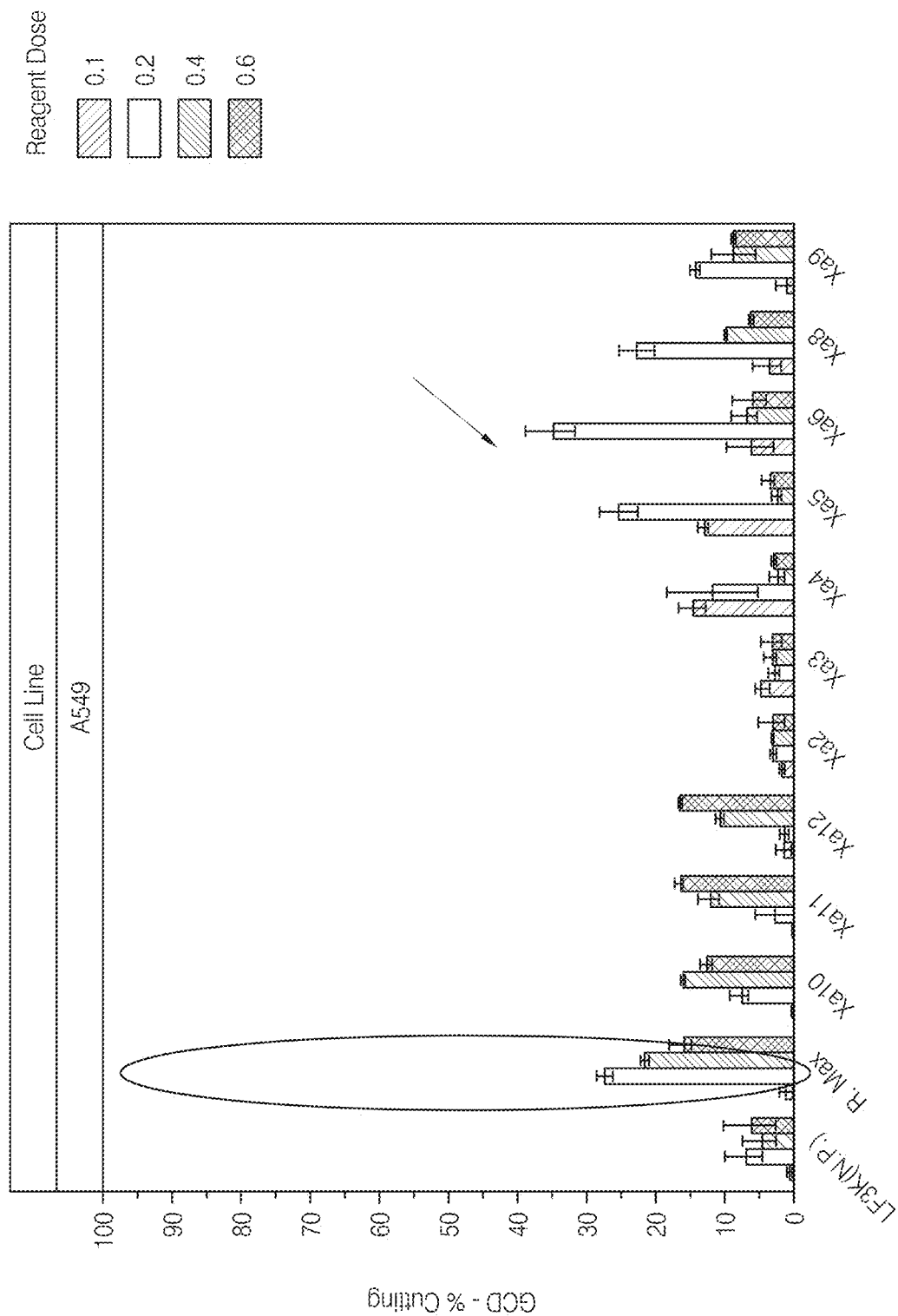
Figure 10F:
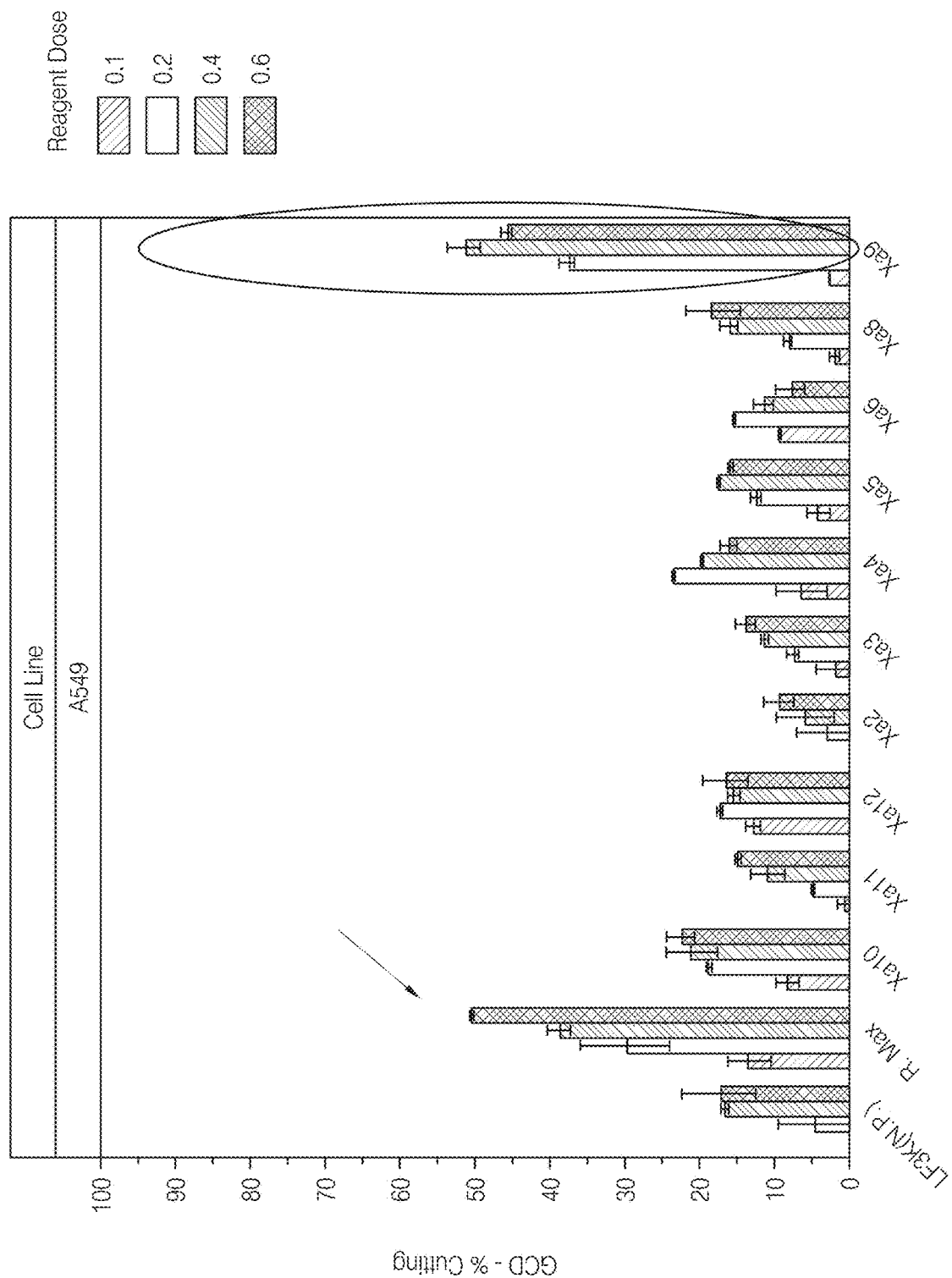

FIG. 10A-10F depicts results of lipid screening experiments using Xa serial, Xb serial, and N serial formulations in Hela cells (FIGS. 10A-10C) and A549 cells (FIGS. 10D-10F). Within each bin of each histogram, the reagent dose is (in order left to right) 0.1, 0.2, 0.4 and 0.6 µL/well.

Example 8. Transfection Enhancer-Peptides in Cas9/gRNA Transfection

Figure 11A:
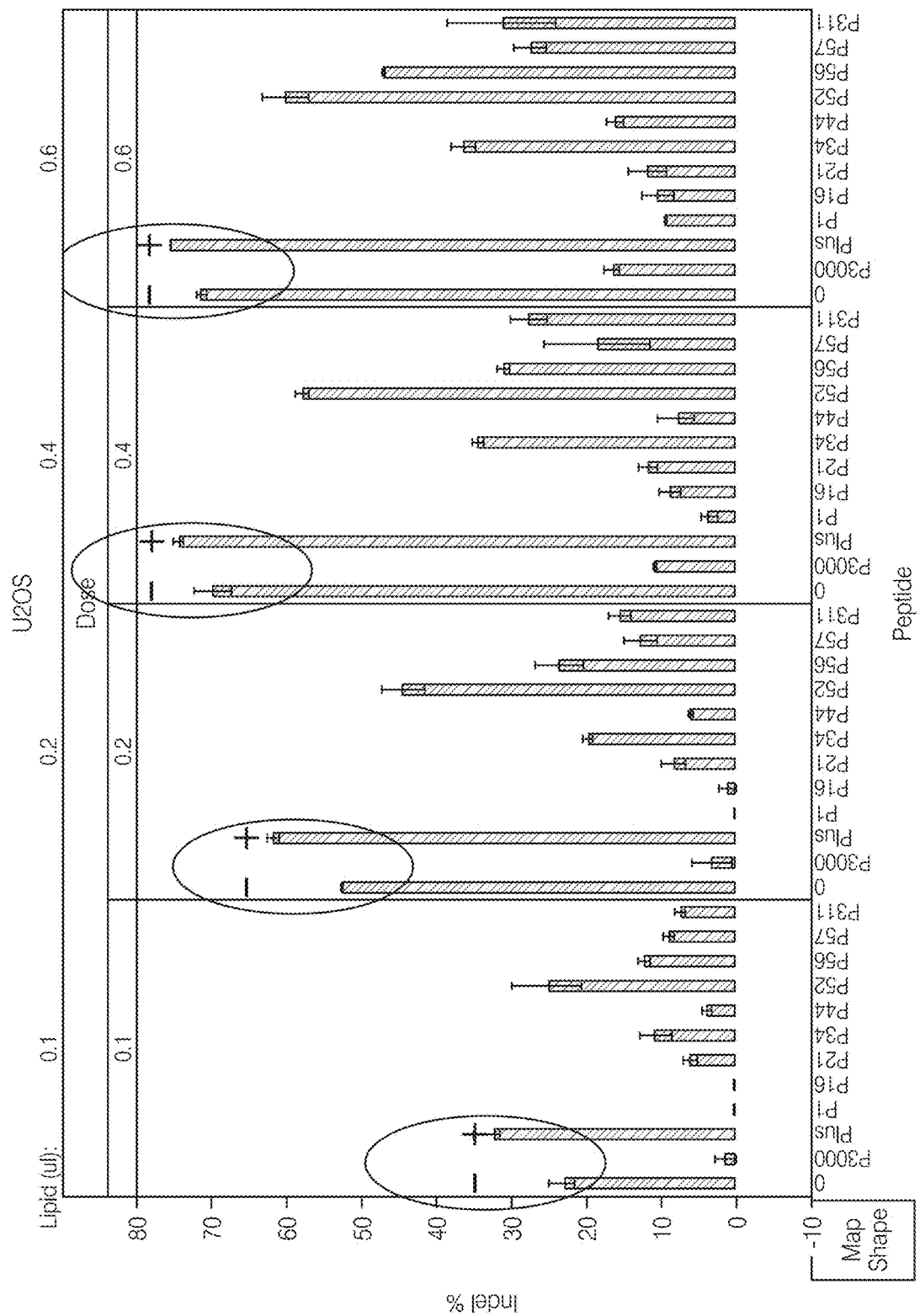
FIGS. 11A-11F. Histograms of results of transfection enhancer experiments for peptides in Cas9/gRNA transfection. Cell lines (left to right, top to bottom): U205, HEK293, Hela, HepG2, A549, MCF7. Y-axis for all histogram is %-indel. Lipid was added as indicated.
Figure 11B:
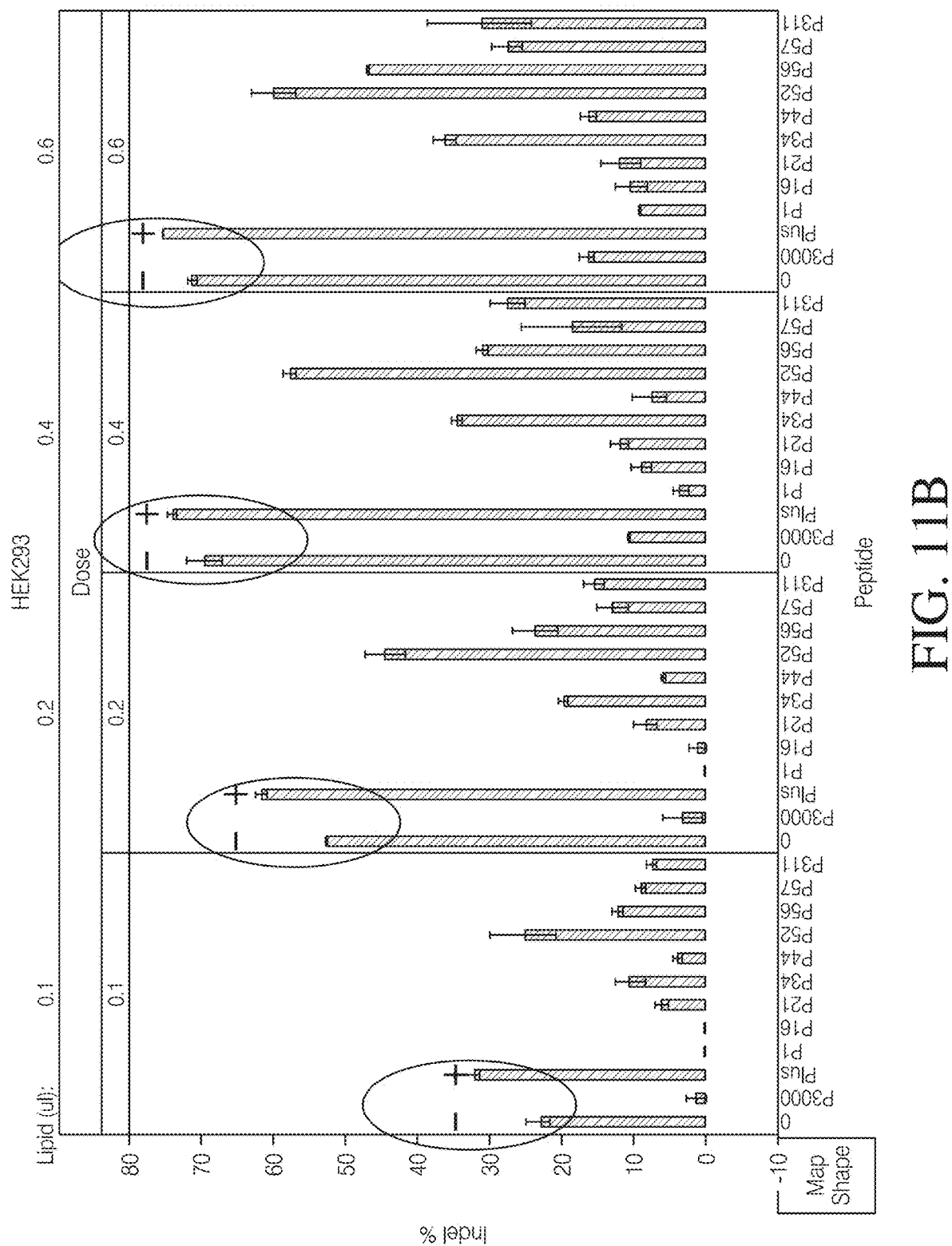
Figure 11C:
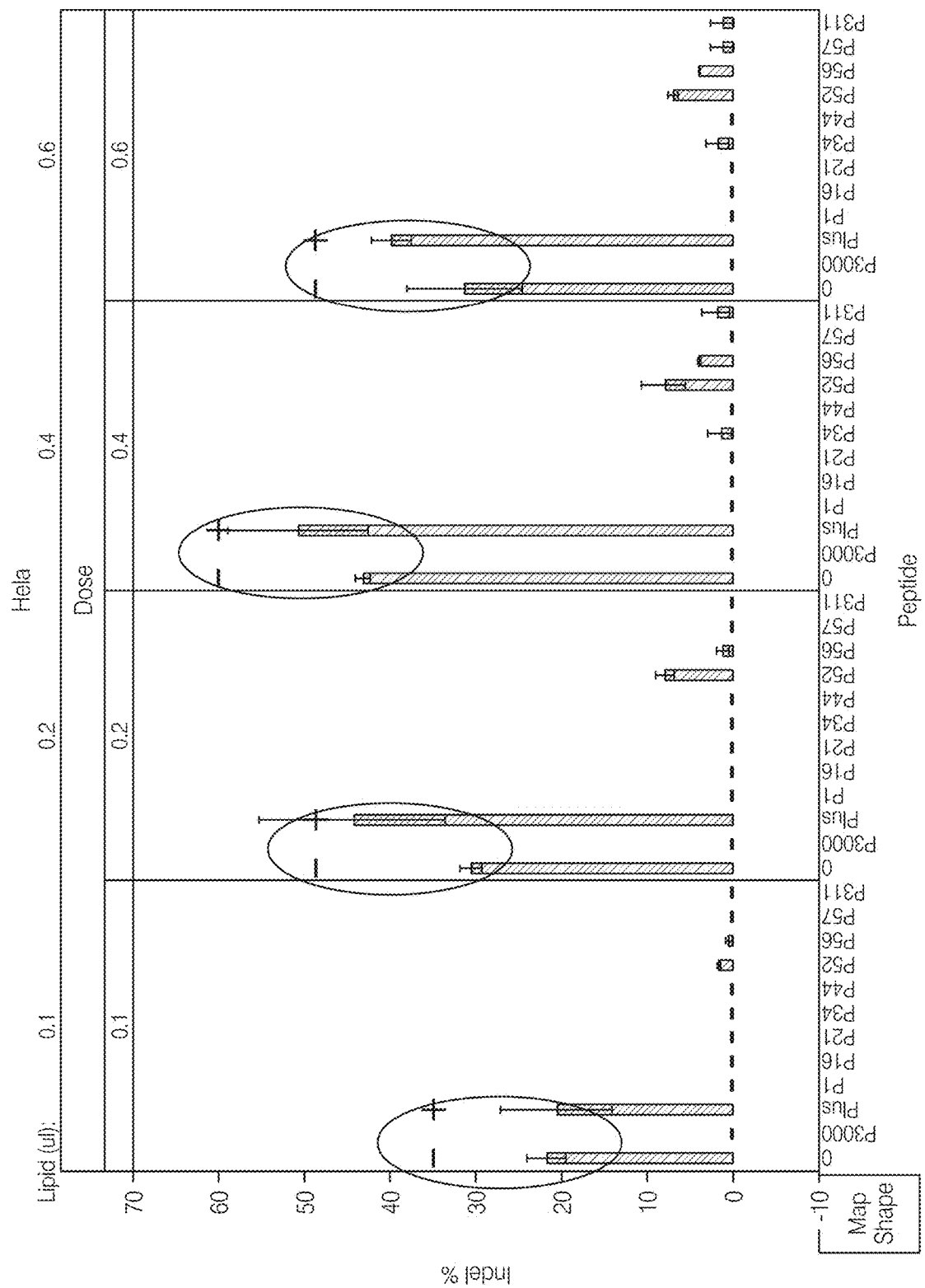
Figure 11D:
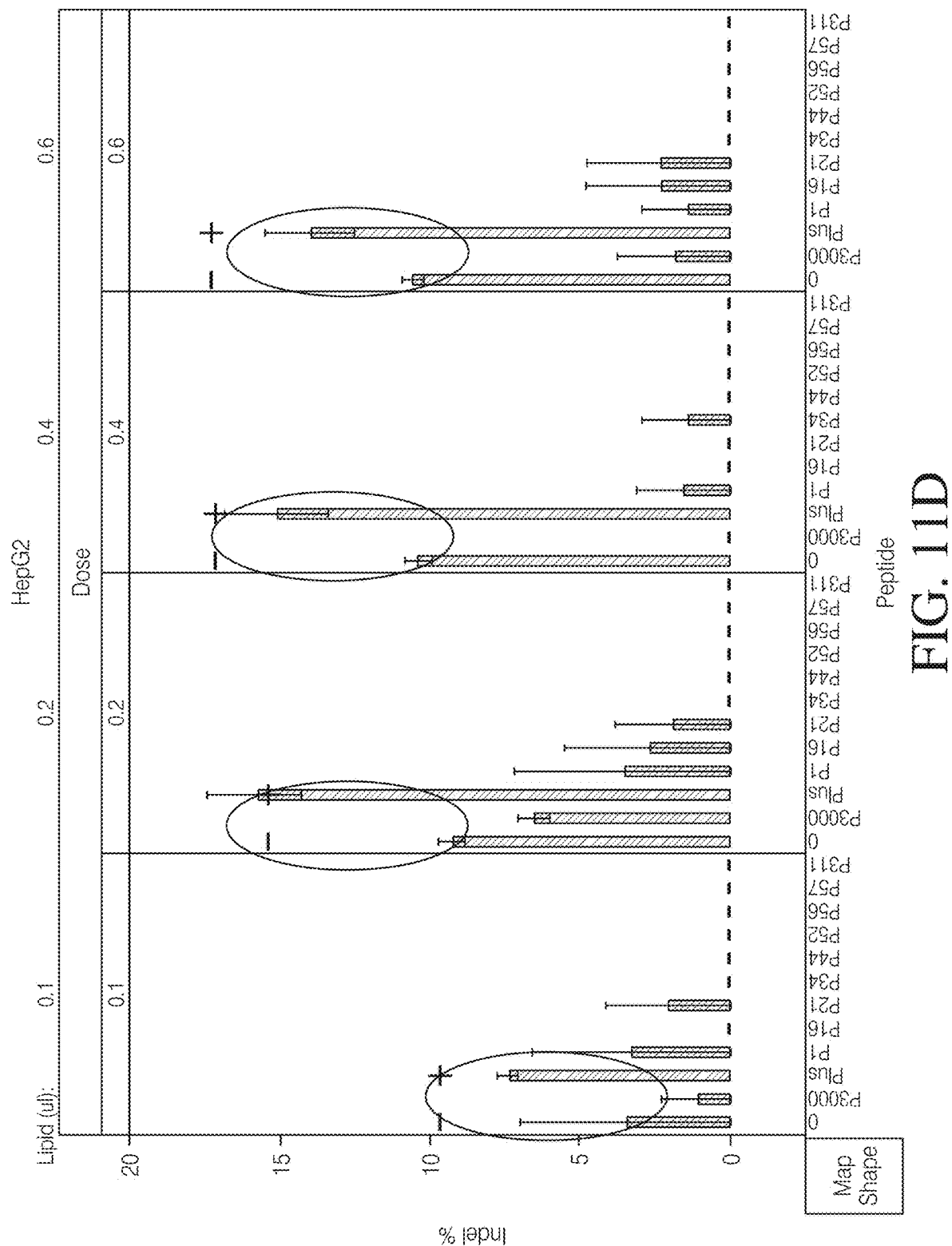
Figure 11E:
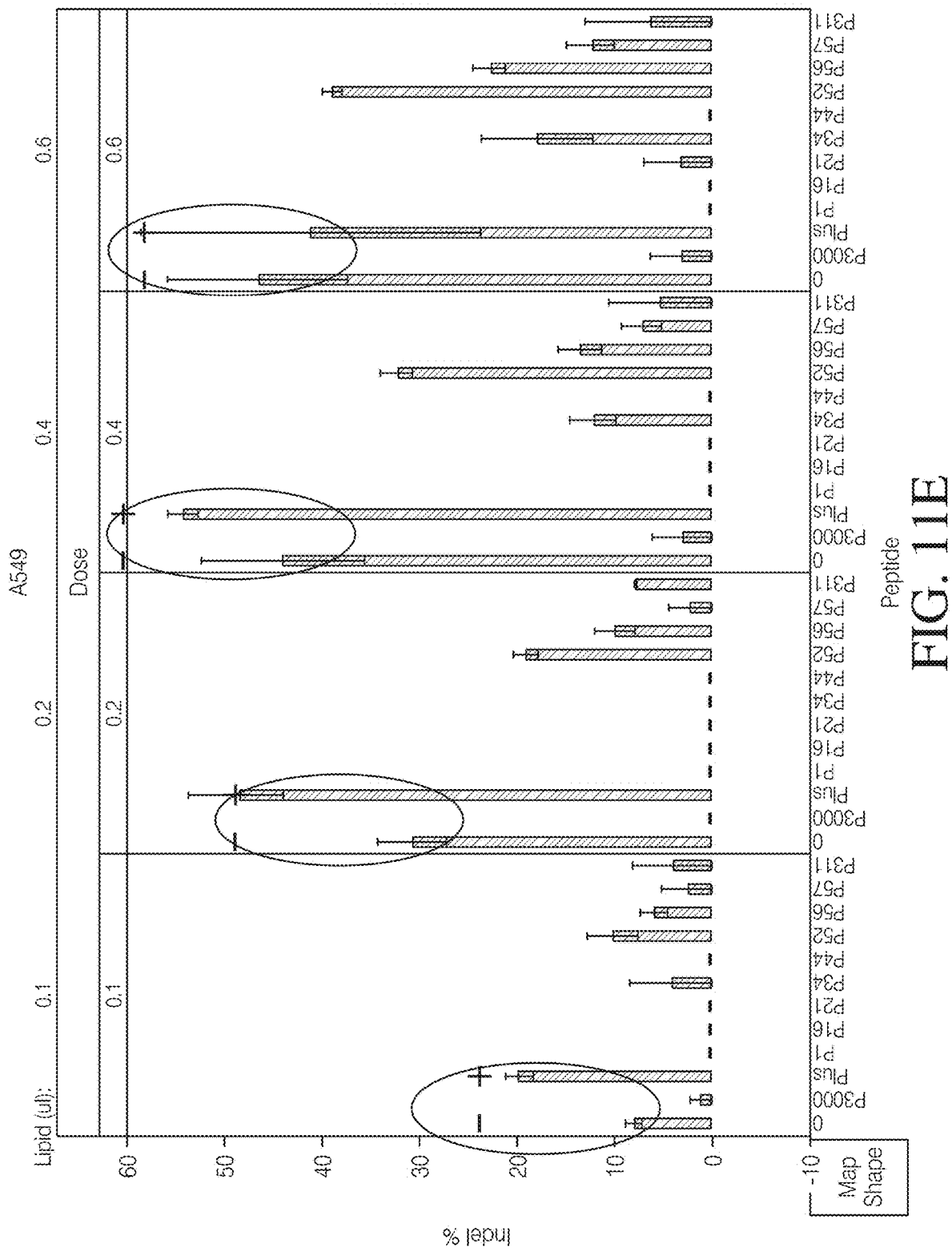
Figure 11F:
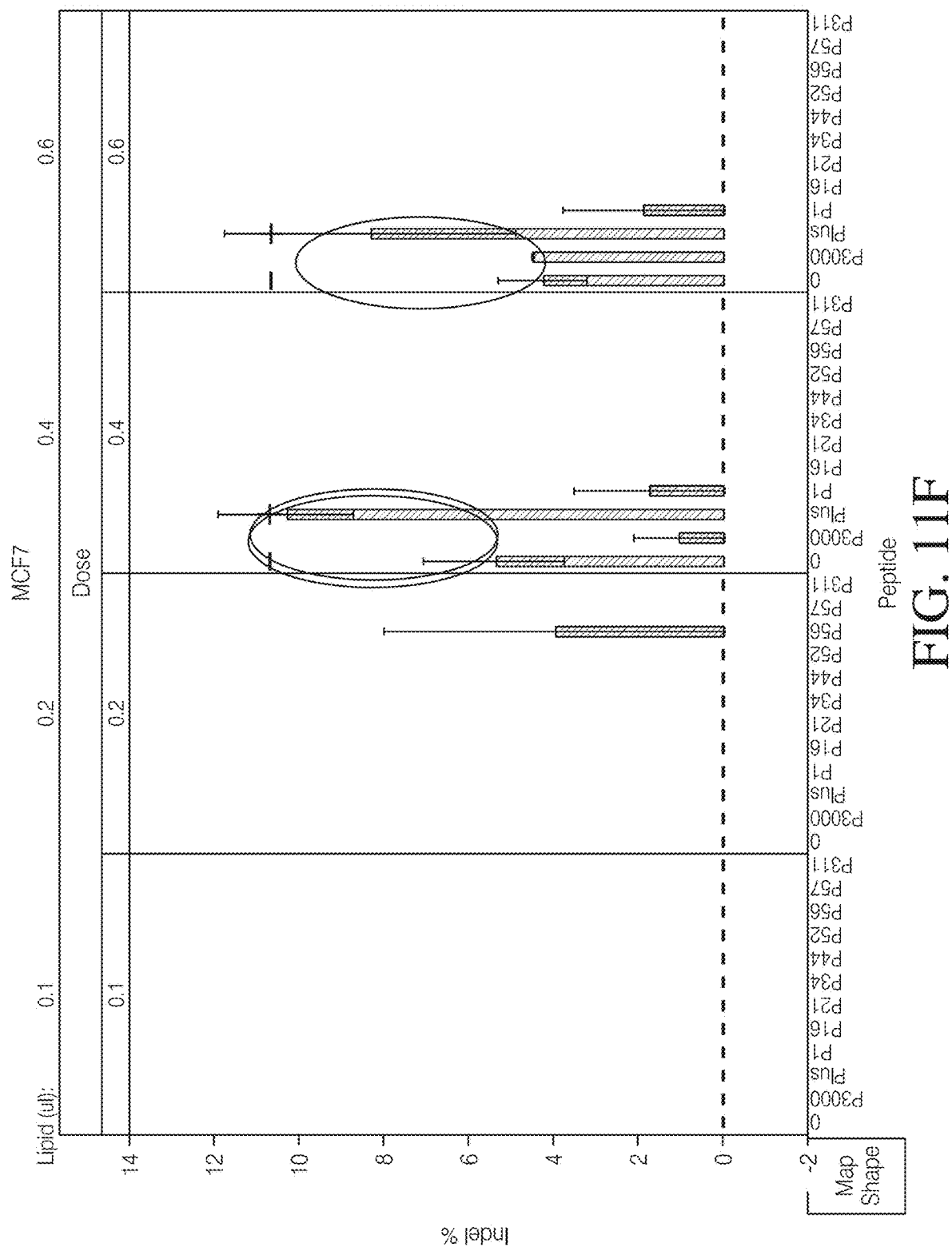

FIGS. 11A-11F depicts histograms of results of transfection enhancer experiments for peptides in Cas9/gRNA transfection. Cell lines: U20S (FIG. 11A), HEK293 (FIG. 11B), HeLa (FIG. 11C), HepG2 (FIG. 11D), A549 (FIG. 11E), MCF7 (FIG. 11F). Y-axis for all histogram is %-indel. Lipid was added as indicated. The "+" symbol indicates addition of Cas9 PLUS™ reagent. It is observed that addition of Cas9 PLUS™ reagent significantly enhanced %-indel in all cell types.

Example 9. Cas9 PLUS™ Reagent Enhanced Cas9/gRNA Delivery

Figure 12:
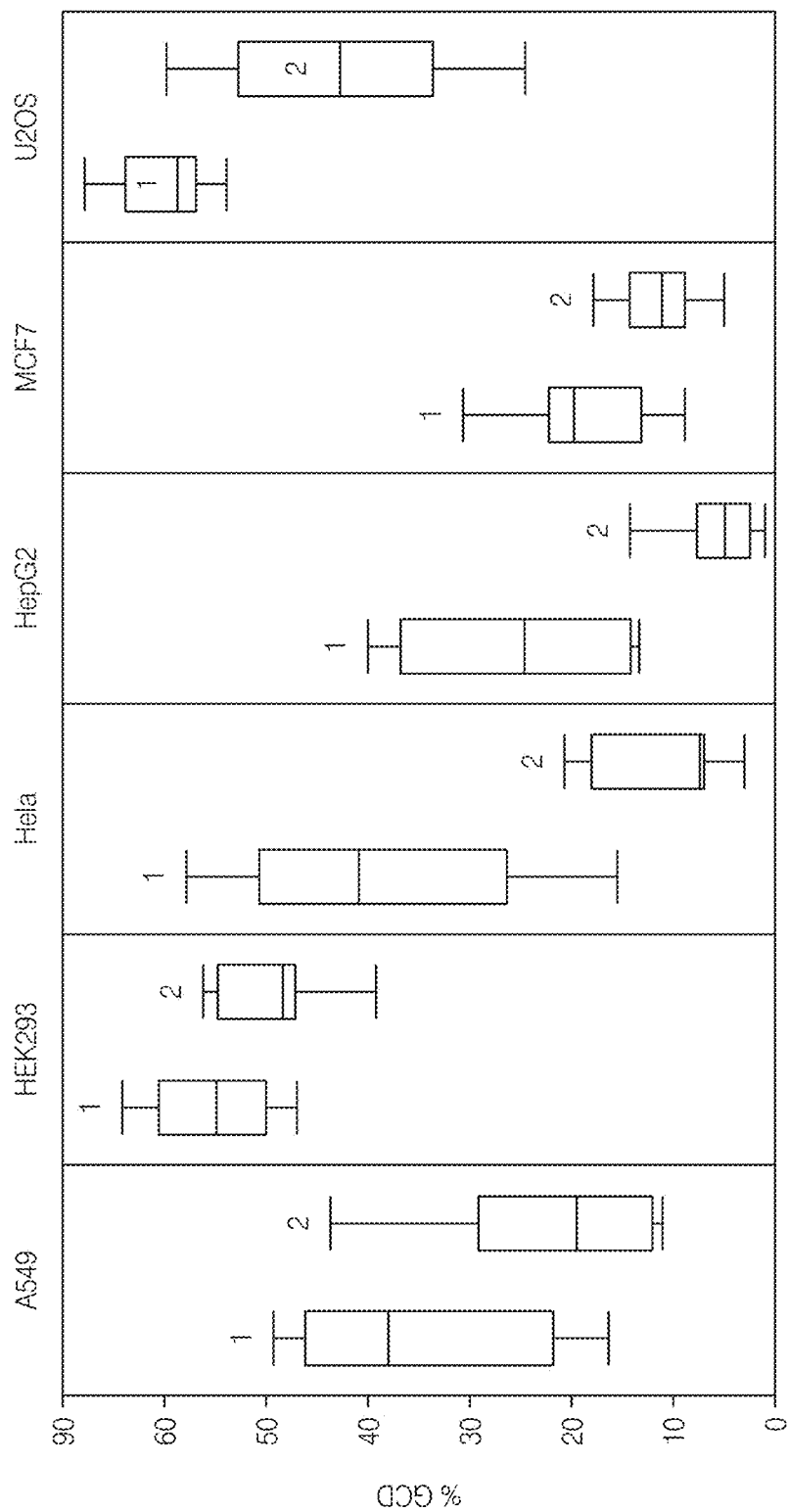
FIG. 12. Figure depicts results demonstrating Cas9 PLUS™ reagent enhanced Cas9/gRNA delivery. Columns (in order left to right) of cell types: A549, HEK293, Hela, HEpG2, MCF7, U205. Y-axis: %-GCD. For each cell type, results are depicted (left to right): Lipofectamine® CRISPRMAX™ Reagent in combination with Cas9 PLUS™ Reagent, and Lipofectamine® RNAiMAX.

FIG. 12 depicts results of experiment in A549, HEK293, Hela, HepG2, MCF7 and U20S cells of Lipofectamine® CRISPRMAX™ Reagent in combination with Cas9 PLUS™ Reagent, and RNAiMAX. The figure depicts significant enhancement of transfection in the combination experiments.

Example 10. CRISPRMAX™ in Additional Cell Lines

The CRISPRMAX™ methodology can be employed in a wide variety of cell lines, including those listed in Tables 5A and 5B following.

TABLE 5A

First set of cell types

| Cell line | Organism | Origin Tissue |
| --- | --- | --- |
| 3T3 cells | Mouse | Embryonic fibroblast |
| A-549 | Human | Lung carcinoma |
| COS-7 | Monkey | Kidney |
| HEK293 | Human | Kidney |
| HeLa | Human | Cervical cancer |
| Jurkat | Human | T cell leukemia |
| MCF-7 | Human | Mammary gland |
| THP-1 | Human | Monocytes |
| K562 cells | Human | Lymphoblastoid |
| U2OS | Human | Osteosarcoma cell line |
| HepG2 | Human | liver cancer cell line |
| HCT116 | Human | colon carcinoma |

TABLE 5B

Second set of cell types.

| Cell line | Organism | Origin Tissue |
| --- | --- | --- |
| mouse ESC | Mouse | Embryonic Stem Cell |
| N2A | Mouse | Liver cancer cell line |
| CHO-K1 | Hamster | Ovary |
| MDA-MB-231 | Human | Breast |
| BJAB | Human | B cell |
| iPSC | Human | Episomal |
| HUVEC | Human | Umbilical vein endothelium |
| CD34+ HPC | Human | umbilical cord blood |
| SC-1 | Human | B Lymphoblasts |
| NSC | Human | Derived from H9 hESC |
| HEKa | Human | Primary epidermal keratinocytes |
| NK-92 | Human | peripheral blood |

Example 11. Comparison Results-CRISPRMAX™ and RNAiMAX

Table 6 following tabulates comparison data for CRISPRMAX™ and RNAiMAX methodologies with respect to cell GCD. Cell lines: HEK293, HCT116, U20S, HELA, A549, HepG2,MCF7, THP1 (suspension), K562 (suspension), Jurkat (suspension), iPSC (E8 culture system), and mESC.

TABLE 6

Comparison of CRISPRMAX ™ with RNAiMAX

| Cell lines | Cell Confluence | GCD (CrisprMax) | GCD (RNAiMax) |
| --- | --- | --- | --- |
| HEK293 | 50% | 70-85% | 85% |
| HCT116 | 50% | 75-85% | No data |
| U2OS | 60% | 60-70% | 18% |
| HeLa | 60% | 40-60% | 10% |
| A549 | 65% | 30-55% | 20% |

TABLE 6-continued

Comparison of CRISPRMAX ™ with RNAiMAX

| Cell lines | Cell Confluence | GCD (CrisprMax) | GCD (RNAiMax) |
|---|---|---|---|
| HepG2 | 70% | 20-35% | 10% |
| MCF7 | 70% | 15-20% | 20% |
| THP1 (suspension) | 100k/well | 15-20% | No data |
| K562 (suspension) | 100k/well | 20-30% | 0 |
| Jurkat (suspension) | 100k/well | 25% | 0 |
| iPSC (E8 Culture System) | 30% | 30-50% | 5% |
| mESC | 25% | 60-65% | 25% |

Informal sequence listing.

CGYGGGGGGPKKKRKVGGGLFEAIAEFIEGGWEGLIEG [SEQ ID NO: 1].

CGYGPKKKRKVGGGGRGDSPCG [SEQ ID NO: 2].

CGYGPKKKRKVGGKFTIVF [SEQ ID NO: 3].

GCGYGPKKKRKVG, wherein N-terminal is modified with Sp-5-CO- (i.e., spermine connected through an amide linkage) [SEQ ID NO: 4].

GGGGGYGPKKKRKVGG, wherein N-terminal is modified with Sp-5-CO- [SEQ ID NO: 5].

GGRGDMFGG, wherein N-terminal is modified with Sp-5-CO- [SEQ ID NO: 6].

GGVKRKKKPGYGGGGVKRKKKPGYGG [SEQ ID NO: 7].

GGYGPKKKRKVG, wherein N-terminal is modified with Sp-5-CO- [SEQ ID NO: 8].

GGYGPKKKRKVGGGGYGPKKKRKVGG, wherein N-terminal is modified with Sp-5-CO- [SEQ ID NO: 9].

GGYGPKKKRKVGGGGYGPKKKRKVGG, wherein N-terminal is modified with Sp-5-CO-NH-CH((CH$_2$)$_4$-NH-5-CO-Sp)-CO- [SEQ ID NO: 10].

GKFTIVFDDDDDD [SEQ ID NO: 11].

GKFTIVFDDDDDDG [SEQ ID NO: 12].

GLFEAIAEFIEGGWEGLIEG [SEQ ID NO: 13].

GLFEAIAEFIEGGWEGLIEGCKFTIVF [SEQ ID NO: 14].

GLFEAIAEFIEGGWEGLIEGGGYGGGGGGPKKKRKVGG [SEQ ID NO: 15].

GLFEAIAIEFIEGGWEGLIEG [SEQ ID NO: 16].

GLFGAIAGFIENGWEGMIDG [SEQ ID NO: 17].

GLFKAIAKFIKGGWKGLIKG [SEQ ID NO: 18].

GRGDSPCGGKKKKKKKKKKKKKKK [SEQ ID NO: 19].

GYGPKKKRKVGG [SEQ ID NO: 20].

GYGPKKKRKVGGGGRGDMFGG, wherein N-terminal is modified with Sp-5-CO- [SEQ ID NO: 21].

KFTIVF [SEQ ID NO: 22].

KFTIVFGGGLFEAIAEFIEGGWEGLIEG [SEQ ID NO: 23].

KFTTIVFCGYGPKKKRKVGG [SEQ ID NO: 24].

KKKKKKKKKKKKKKK [SEQ ID NO: 25].

KKKKKKKKKKKKKKKCGYGPKKKRKVGGGRGDSP [SEQ ID NO: 26].

KKKKKKKKKKKKKKKGGCGYGGGGGGPKKKRKVGGGLFEAIAEFIEGGWEGLIEG [SEQ ID NO: 27].

KKKKKKKKKKKKKKKGGCGYGGGPKKKRKVGGKFTIVF [SEQ ID NO: 28].

| Informal sequence listing. |
|---|
| KKKKKKKKKKKKKKKKGGCGYGPKKKRKVGG [SEQ ID NO: 29]. |
| KKKKKKKKKKKKKKKKGGRGDSPCG [SEQ ID NO: 30]. |
| KKKKKKKKKKKKKKKKGKFTIVFDDDDDD [SEQ ID NO: 31]. |
| KKKKKKKKKKKKKKKKGKFTIVFDDDDDDG [SEQ ID NO: 32]. |
| KKKKKKKKKKKKKKKKGLFEAIAEFIEGGWEGLIEGCKFTIVF [SEQ ID NO: 33]. |
| KKKKKKKKKKKKKKKKGLFEAIAEFIEGGWEGLIEGGGYGGGGG PKKKRKVGG [SEQ ID NO: 34]. |
| KKKKKKKKKKKKKKKKKFTIVFGGGLFEAIAEFIEGGWEGLIEG [SEQ ID NO: 35]. |
| KKKKKKKKKKKKKKKKKFTTIVFCGYGPKKKRKVGG [SEQ ID NO: 36]. |
| KKKKKKKKKKKKKKKKSSDDEATADSQHSTPPKKKRKVGG [SEQ ID NO: 37]. |
| MSYYHHHHHHDYDIPTTENLYFQGSGLFEAIAEFIEGGWEGLIEG [SEQ ID NO: 38]. |
| MSYYHHHHHHDYDIPTTENLYFQGSGYGPKKKRKVGG [SEQ ID NO: 39]. |
| MSYYHHHHHHDYDIPTTENLYFQGSKFTIVF [SEQ ID NO: 40]. |
| MSYYHHHHHHDYDIPTTENLYFQGSRGDSPC [SEQ ID NO: 41]. |
| MSYYHHHHHHGLFEAIAEFIEGGWEGLIEG [SEQ ID NO: 42]. |
| MSYYHHHHHHGYGPKKKRKVGG [SEQ ID NO:43]. |
| MSYYHHHHHHKFTIVF [SEQ ID NO: 44]. |
| MSYYHHHHHHRGDSPC [SEQ ID NO: 45]. |
| SSDDEATADSQHSTPPKKKRKVGG [SEQ ID NO: 46]. |

What is claimed is:

1. A composition comprising a ribonucleoprotein complex, a lipid aggregate-forming cationic lipid and an enhancer element;
wherein said lipid aggregate-forming cationic lipid has the structure of formula:

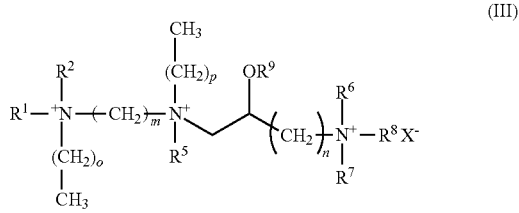

(III)

wherein
$R^1$ and $R^2$ are independently hydrogen, substituted or unsubstituted heteroalkyl, or substituted or unsubstituted alkyl,
$R^5$, $R^6$, $R^7$, $R^8$ and $R^9$ are independently hydrogen or unsubstituted alkyl;
X is an anion; and
m is an integer from 1-10;
n is an integer from 1-6; and
o and p are independently integers from 8-30,
and wherein said enhancer element comprises a polyamine moiety covalently attached to a nuclear localization signal sequence.

2. The composition of claim 1, wherein said ribonucleoprotein complex comprises an endonuclease and a ribonucleic acid.

3. The composition of claim 2, wherein said endonuclease comprises CRISPR associated protein 9 (Cas9) and said ribonucleic acid comprises a guide RNA.

4. The composition of claim 1, wherein $R^1$ is substituted or unsubstituted heteroalkyl.

5. The composition of claim 1, wherein said polyamine moiety is a spermine moiety.

6. The composition of claim 1, wherein said polyamine moiety is a plurality of spermine moieties.

7. The composition of claim 1, wherein said polyamine moiety is covalently attached to the N-terminus of said nuclear localization signal sequence.

8. The composition of claim 1, wherein said enhancer element comprises a peptide comprising the sequence of SEQ ID NO:1-SEQ ID NO:46.

9. The composition of claim 1, wherein said enhancer element comprises a peptide comprising at least two nuclear localization signal (NLS) sequences.

10. The composition of claim 1, further comprising a donor nucleic acid.

11. The composition of claim 1, further comprising a eukaryotic cell.

12. The composition of claim 11, wherein said eukaryotic cell is a pluripotent cell, a lymphatic cell, a T cell, or a hepatocyte.

13. The composition of claim 12, wherein said pluripotent cell is an induced pluripotent cell or an embryonic stem cell.

14. The composition of claim 1, wherein $R^5$, $R^6$, $R^7$, $R^8$ and $R^9$ are hydrogen.

15. The composition of claim 1, wherein $R^2$ is hydrogen or substituted or unsubstituted alkyl.

* * * * *